United States Patent
Herrmann et al.

(10) Patent No.: US 10,967,070 B2
(45) Date of Patent: Apr. 6, 2021

(54) CELL PENETRATING CONJUGATES AND METHODS OF USE THEREOF

(71) Applicant: City of Hope, Duarte, CA (US)

(72) Inventors: Andreas Herrmann, Pasadena, CA (US); Hua Yu, Glendora, CA (US); Piotr Marek Swiderski, San Dimas, CA (US); John Ernest Shively, Arcadia, CA (US); Lin Li, Monrovia, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 15/056,777

(22) Filed: Feb. 29, 2016

(65) Prior Publication Data

US 2016/0317671 A1    Nov. 3, 2016

Related U.S. Application Data

(63) Continuation of application No. PCT/US2014/053549, filed on Aug. 29, 2014.

(60) Provisional application No. 61/871,729, filed on Aug. 29, 2013, provisional application No. 61/939,993, filed on Feb. 14, 2014.

(51) Int. Cl.
| | |
|---|---|
| *A61K 47/50* | (2017.01) |
| *C07K 16/08* | (2006.01) |
| *C07K 16/40* | (2006.01) |
| *C07K 16/18* | (2006.01) |
| *A61K 39/44* | (2006.01) |
| *A61K 47/68* | (2017.01) |
| *A61K 47/54* | (2017.01) |
| *A61K 39/00* | (2006.01) |
| *A61K 38/00* | (2006.01) |
| *C12N 15/11* | (2006.01) |

(52) U.S. Cl.
CPC .......... *A61K 47/6843* (2017.08); *A61K 39/44* (2013.01); *A61K 47/549* (2017.08); *A61K 47/6807* (2017.08); *C07K 16/084* (2013.01); *C07K 16/18* (2013.01); *C07K 16/40* (2013.01); *A61K 38/00* (2013.01); *A61K 2039/505* (2013.01); *A61K 2039/507* (2013.01); *C07K 2317/73* (2013.01); *C07K 2317/76* (2013.01); *C07K 2319/10* (2013.01); *C12N 15/11* (2013.01); *C12N 2310/315* (2013.01); *C12N 2310/3513* (2013.01)

(58) Field of Classification Search
None
See application file for complete search history.

(56) References Cited

U.S. PATENT DOCUMENTS

| | | | |
|---|---|---|---|
| 5,965,371 A | 10/1999 | Marasco et al. | |
| 6,004,940 A | 12/1999 | Marasco et al. | |
| 6,903,077 B1 | 6/2005 | Heintz | |
| 7,186,697 B2 | 3/2007 | Marasco et al. | |
| 7,867,500 B2 | 1/2011 | Simons, Jr. et al. | |
| 8,252,902 B2 | 8/2012 | Barbas et al. | |
| 2003/0158109 A1 | 8/2003 | Giese | |
| 2004/0052762 A1* | 3/2004 | Yu | A61K 38/1709 424/85.2 |
| 2004/0147027 A1 | 7/2004 | Troy et al. | |
| 2005/0042632 A1 | 2/2005 | Radka | |
| 2006/0222657 A1 | 10/2006 | Dowdy et al. | |
| 2007/0167388 A1* | 7/2007 | Sczakiel | C12N 15/117 514/44 A |
| 2007/0225213 A1 | 9/2007 | Kosak | |
| 2009/0123467 A1* | 5/2009 | Bedi | A61K 47/484 424/134.1 |
| 2009/0186802 A1 | 7/2009 | Allius et al. | |
| 2010/0190691 A1 | 7/2010 | Epenetos et al. | |
| 2011/0065779 A1 | 3/2011 | Fang et al. | |
| 2011/0129421 A1 | 6/2011 | Liu et al. | |
| 2011/0159039 A1 | 6/2011 | Houghton et al. | |
| 2011/0212028 A1 | 9/2011 | Ahmed et al. | |
| 2011/0218334 A1 | 9/2011 | Maier et al. | |
| 2012/0122795 A1 | 5/2012 | Butler et al. | |
| 2012/0190732 A1* | 7/2012 | Chang | C12N 15/115 514/44 R |
| 2013/0137644 A1 | 5/2013 | Alluis et al. | |
| 2014/0050723 A1* | 2/2014 | Hansen | C07K 16/44 424/133.1 |

FOREIGN PATENT DOCUMENTS

| | | |
|---|---|---|
| CN | 102448494 A | 5/2012 |
| WO | WO-94/01131 A1 | 1/1994 |

(Continued)

OTHER PUBLICATIONS

Song et al., JAK1 Activates STAT3 Activity in Non-Small-Cell Lung Cancer Cells and IL-6 Neutralizing Antibodies Can Suppress JAK1-STAT3 Signaling; Molecular Cancer Therapeutics; vol. 10, No. 3, pp. 481-494, 2011.*

Chu et al., Aptamer:Toxin Conjugates that Specifically Target Prostate Tumor Cells; Cancer Res, vol. 66, No. 12, pp. 5989-5992, 2006 (Year: 2006).*

Antopolsky, M. et al. (Jul.-Aug. 1999). "Peptide-oligonucleotide phosphorothioate conjugates with membrane translocation and nuclear localization properties," *Bioconjug Chem* 10(4):598-606.

Gupta, B. et al. (Feb. 28, 2005, e-published Dec. 22, 2004). "Intracellular delivery of large molecules and small particles by cell-penetrating proteins and peptides," *Adv Drug Deliv Rev* 57(4):637-651.

(Continued)

*Primary Examiner* — Antonio Galisteo Gonzalez
(74) *Attorney, Agent, or Firm* — Mintz, Levin, Cohn, Ferris, Glovsky and Popeo, P.C.

(57) ABSTRACT

Provided herein are cell penetrating conjugates. The conjugates include a non-cell penetrating protein attached to a phosphorothioate nucleic acid or phosphorothioate polymer backbone, wherein the phosphorothioate nucleic acid or phosphorothioate polymer backbone enhances intracellular delivery of the non-cell penetrating protein. Also provided are compositions and kits comprising the cojugates.

8 Claims, 61 Drawing Sheets

Specification includes a Sequence Listing.

(56) References Cited

FOREIGN PATENT DOCUMENTS

| WO | WO-95/02422 A1 | 1/1995 |
|---|---|---|
| WO | WO-2010/093395 A1 | 8/2010 |
| WO | WO-2011/155853 A1 | 12/2011 |
| WO | WO-2013/033230 A1 | 3/2013 |

OTHER PUBLICATIONS

Herrmann, A. et al. (Sep. 15, 2007, e-published Aug. 28, 2007). "Nucleocytoplasmic shuttling of persistently activated STAT3," *J Cell Science* 120(Pt. 18):3249-3261.

Herrmann, A. et al. (Oct. 1, 2010, e-published Sep. 14, 2010). "Targeting Stat3 in the myeloid compartment drastically improves the in vivo antitumor functions of adoptively transferred T cells," *Cancer Res.* 70(19):7455-7464.

International Preliminary Report on Patentability dated Mar. 1, 2016, for PCT Application No. PCT/US2014/053549, filed Aug. 29, 2014, 7 pages.

International Search Report dated Dec. 18, 2014, for PCT Application No. PCT/US2014/053549, filed Aug. 29, 2014, 3 pages.

Kujawski, M. et al. (Oct. 2008). "Stat3 mediates myeloid cell-dependent tumor angiogenesis in mice," *J Clin Invest* 118(10):3367-3377.

Liu, B. et al. (Oct. 2007, e-published Jun. 7, 2007). "Recombinant full-length human IgG1s targeting hormone-refractory prostate cancer," *J Mol Med* 85(10):1113-1123.

Temsamani, J. et al. (1994). "Cellular uptake of oligodeoxynucleotide phosphorothioates and their analogs," *Antisense Res Dev* 4(1):35-42.

Torchilin, V.P. et al. (2006). "Recent approaches to intracellular delivery of drugs and DNA and organelle targeting," *Annu Rev Biomed Eng* 8:343-375.

Uckun, F.M. et al. (Jan. 2013). "Rational design of an immunoconjugate for selective knock-down of leukemia-specific E2A-PBX1 fusion gene expression in human Pre-B leukemia," *Integr Biol* 5(1):122-132.

Winkler, J. (Jul. 2013). "Oligonucleotide conjugates for therapeutic applications," *Ther Deliv* 4(7):791-809.

Zhang, K. et al. (Oct. 10, 2012, e-published Sep. 28, 2012). "Antibody-linked spherical nucleic acids for cellular targeting," *J Am Chem Soc* 134(40):16488-16491.

Du, X. et al. (Aug. 1, 2000). "Differential Cellular Internalization of Anti-CD19 and CD22 Immunotoxins Results in Different Cytotoxic Activity," *Cancer Res* 68(15):6300-6305.

Oehlke, J. et al. (Aug. 2002). "Cellular uptake of antisense oligonucleotides after complexing or conjugation with cell-penetrating model peptides," *Eur J Biochem* 269(16):4025-4032.

Munyendo, W.L. et al. (Mar. 30, 2012). "Cell penetrating peptides in the delivery of biopharmaceuticals," *Biomolecules* 2(2):187-202.

Stein, C.A. et al. (Jan. 2010, e-published Oct. 23, 2009). "Efficient gene silencing by delivery of locked nucleic acid antisense oligonucleotides, unassisted by transfection reagents," Nucleic Acids Res 38(1):e3.

* cited by examiner

BG - Background-ROI

B - Bleach-ROI

1 – detection ROI 1 – nucleus bleached cell

2 – detection ROI 2 – nucleus unbleached cell

SEQUENCE LISTING

```
<160> NUMBER OF SEQ ID NOS: 7

<210> SEQ ID NO 1
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 1
agcttcattt cccgtaaatc cctaagct                                            28

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: Oligo has phosphorothioated backbone

<400> SEQUENCE: 2
tccatgagct tcctgatgct                                                    20
```

```
<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
tccatgagct tcctgatgct                                                     20

<210> SEQ ID NO 4
<211> LENGTH: 19
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Oligo has phosphorothioated backbone

<400> SEQUENCE: 4
ctgtagtcct ctgagtacc                                                      19

<210> SEQ ID NO 5
<211> LENGTH: 19
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Oligo has phosphorothioated backbone

<400> SEQUENCE: 5
cccaggagtc tcctgattt                                                      19

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Oligo has phosphorothioated backbone

<400> SEQUENCE: 6
tcgtagtcct tcgagtacct                                                     20

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: Oligo has phosphorothioated backbone

<400> SEQUENCE: 7
tagatgacct tcctgctgct                                                     20
```

US 10,967,070 B2

CELL PENETRATING CONJUGATES AND METHODS OF USE THEREOF

CROSS REFERENCE TO RELATED APPLICATIONS

This application is a continuation of PCT Application No. PCT/US2014/053549, filed Aug. 29, 2014 which claims priority U.S. Provisional Application No. 61/871,729, filed Aug. 29, 2013, and U.S. Provisional Application No. 61/939,993, filed Feb. 14, 2014, which are incorporated by reference herein in their entireties.

REFERENCE TO A "SEQUENCE LISTING," A TABLE, OR A COMPUTER PROGRAM LISTING APPENDIX SUBMITTED AS AN ASCII FILE

The Sequence Listing written in file 48440-528N01US ST25, created on Feb. 23, 2016, 2,270 bytes, machine format IBM-PC, MS-Windows operating system, is hereby incorporated by reference.

STATEMENT AS TO RIGHTS TO INVENTIONS MADE UNDER FEDERALLY SPONSORED RESEARCH AND DEVELOPMENT

This invention was made using support under Grant Number CA122976 awarded by the National Institutes of Health. The government has certain rights to this invention.

BACKGROUND OF THE INVENTION

Antibodies have proven to be an efficacious drug modality for its easy generation, specificity and bio-durability relative to other types of drugs such as small molecule drugs. Current antibody therapy can only target extracellular molecules. However, numerous important targets for disease treatment and disease diagnosis are intracellular. For example, a number of transcriptional factors, such as STAT3, are among the most crucial yet challenging targets for cancer therapy. Provided herein are solutions for these and other needs in the art.

BRIEF SUMMARY OF THE INVENTION

There is a need to use peptides and proteins (e.g. antibodies) to target intracellular molecules. However, the ability of peptides and proteins (e.g. antibodies) to target intracellular molecules in an effective manner has proven difficult. As described throughout and demonstrated in the examples below, provided herein, inter alia, is a methodology to modify peptides and proteins (e.g. antibodies) to allow them to be cell penetrating, enabling them to target intracellular molecules effectively even with systemic administration. Further, it is shown that two different proteins in a complex can be targeted with the provided modified antibodies. The provided cell-penetrating peptide (protein) technology can be broadly used to target various intracellular proteins (e.g., oncogenic proteins, intracellularly residing viral proteins, and others).

Provided herein, inter alia, are cell penetrating conjugates. In one aspect, the conjugates include a non-cell penetrating protein attached to a phosphorothioate nucleic acid or phosphorothioate polymer backbone, wherein the phosphorothioate nucleic acid or phosphorothioate polymer backbone enhances intracellular delivery of the non-cell penetrating protein. In other aspects, compositions and kits comprising the conjugates are provided.

In another aspect, a method of delivering a non-cell penetrating protein into a cell is provided. The method includes contacting the cell with a cell penetrating conjugate including a non-cell penetrating protein attached to a phosphorothioate nucleic acid or phosphorothioate polymer backbone, wherein the phosphorothioate nucleic acid or phosphorothioate polymer backbone enhances intracellular delivery of the non-cell penetrating protein.

In another aspect, a method of treating a disease in a subject is provided. The method includes administering to the subject an effective amount of a cell penetrating conjugate including a non-cell penetrating protein attached to a phosphorothioate nucleic acid or phosphorothioate polymer backbone, wherein the phosphorothioate nucleic acid or phosphorothioate polymer backbone enhances intracellular delivery of the non-cell penetrating protein and wherein administration of the conjugate treats the disease in the subject.

BRIEF DESCRIPTION OF THE DRAWINGS

FIG. 1A are images showing STAT3-GFP is confined in the cytoplasm by intracellular delivery of STAT3 and GFP antibodies to STAT3-GFP in mouse 3T3/v-Src cells. Hoechst 33342 was added to stain nucleic acids. Scale bar 10 μm. FIG. 1B are images of Western blot analysis following either STAT3 or exportin 7 immunoprecipitation of tumor lysates showing STAT3 interacts with exportin 7. PIS: pre-immunoserum. FIG. 1C are images of in situ localization of interacting STAT3 and exportin 7 in U251 cells using the Duolink® (Uppsala, Sweden) technique. Interaction events are shown as dot-like structures. A STAT3 blocking peptide preventing STAT3 recognition by the detecting antibody has been used as control. Selected areas (dashed line) are shown magnified in the lower right corner. Scale bar 10 μm (left panel). FIG. 1D are graphs of quantitative analysis of STAT3 interaction with exportin 7, n=4 (total signals, left); nuclear vs. cytoplasmic signal events, n=26 (right). Student's T-test *, $P<0.001$; , $P<0.01$; *$P<0.05$. FIG. 1E are images showing intracellular delivery of STAT3 and exportin 7 antibodies trap STAT3 in cytoplasm. Live cell confocal imaging demonstrates the effects of the duo-antibody approach on STAT3 cellular redistribution. Scale bar 10 μm.

FIG. 2A are images of iFLAP live cell confocal imaging showing lysine 685 is crucial for STAT3 nucleocytoplasmic shuttling. Intracellular mobility of STAT3 or STAT3K685R fused to CFP and YFP were tracked as a function of time by rounds of cytoplasmic YFP bleaching. Scale bar, 10 μm. FIG. 2B are images showing STAT3K685R undergoes nuclear retention and is not retained in the cell cytoplasm by STAT3 and GFP antibodies. Scale bar, 10 μm. FIG. 2C are images of Western blots showing STAT3 lysine acetylation but not tyrosine phosphorylation is crucial for interaction with exportin 7. FIG. 2D are images showing mutating K685 in constitutively-active STAT3 abolishes interaction between STAT3 and exportin 7. STAT3 and STAT3K685R were overexpressed in U251 human tumor cells and co-precipitation experiments were performed from whole cell lysates. FIG.

2E are images showing mutating K685 decreases STAT3 interactions with exportin 7, nuclear export check-points nucleoporin 50 and nucleoporin 153 in vivo. Shown are Western blot analyses following immunoprecipitation of lysates prepared from tumors grown by engrafting STAT3 deficient MEF cells reconstituted with STAT3 wt-YFP or STAT3K685R-YFP in athymic nude mice. FIG. 2F are images showing acetylation deficient STAT3K685R restricts nuclear egress of exportin 7 in vivo. Shown are confocal micrographs. Nucleic acids were stained with Hoechst 33342. Scale bar, 50 µm. FIG. 2G are graphs showing quantification of nuclear exportin 7, n=6 (left panel) and nuclear diameters, n=6 (right panel) in STAT3 wt and STAT3K685R tumors. *, P<0.001; , P<0.01.

FIG. 3A is a graph showing tumor growth kinetics of the mouse B16 melanoma in C57BL/6 mice upon indicated antibody treatments. Each point represents a treatment. Student's T-test *, P<0.001; , P<0.01; *P<0.05. FIG. 3B are images of the duo-antibody treatment disrupting STAT3 shuttling in tumors, as shown by Western blot analysis following co-immunoprecipitation of STAT3 and nucleoporin 50 or 153 of tumors. FIG. 3C are images for hematoxylin and eosin (H&E) stain and confocal images of tumor microsections to show the effects of the duo-antibody treatments on tumor, tumor vasculature and proliferative activity in vivo. Scale bar, 100 µm. FIG. 3D is a bar graph showing quantification of CD31+ tumor vasculature (n=4) and Ki67+ proliferative activity (n=3). Student's T-test *, P<0.001; , P<0.01; *P<0.05. FIG. 3E are images of Western blots showing protein expression of STAT3 target genes, Bcl-2 and cyclin D1, in tumors treated with indicated antibodies. FIG. 3F is a graph of tumor growth kinetics of human U87 brain tumor engrafted in athymic nu/nu mice locally treated by indicated antibodies. Student's T-test *, P<0.001; , P<0.01; *P<0.05. FIG. 3G are images of oligo-pull-down assay using a Sis-inducible element (SIE) oligonucleotide followed by Western blot analysis indicating diminished STAT3 DNA-binding activity in tumors treated with the duo-antibody approach. Precipitates were first separated by SDS-PAGE. FIG. 3H are images of the duo-antibody trapping approach effectively inducing tumor cell apoptosis and tumor blood vasculature collapse in vivo. Upper panels: intravital-multiphoton imaging to detect annexin V signals. Annexin V was injected systemically right before tumor imaging. Confocal images of CD31+ tumor vasculature are shown in the lower panels. Scale bar, 100 µm. FIG. 3I is a bar graph showing quantification of annexin V+ tumor cell apoptosis (n=4) and CD31+ tumor vasculature (n=7) in tumors treated by indicated antibodies. Student's T-test *, P<0.001; , P<0.01; *P<0.05.

FIG. 4A are graphs of flowcytometric analyses of cellular internalization at indicated time and doses using fluorescently labeled modified antibodies. FIG. 4B are images of confocal microscopic analyses of subcellular localization of the phosphorothioated nucleic acid modified antibodies. Antibodies (anti-Stat3-oligo-FAM and anti-exportin 7-oligo-TAMRA) were incubated at 10 µg/ml for 2 h. Scale bar, 20 µm. FIG. 4C is a graph showing tumor volume of mice bearing B16 melanoma tumors treated locally every other day with 10 µg total dose of phosphorothioated nucleic acid-modified antibodies as indicated. Standard deviation (SD) shown. Student's T-test *, P<0.001; , P<0.01; *P<0.05. FIG. 4D is a graph showing tumor volume of mice bearing B16 melanoma tumors treated locally or systemically every other day with 10 µg total dose of oligo-modified antibodies or left untreated. SD shown. Student's T-test *, P<0.001; , P<0.01; *P<0.05. FIG. 4E is a graph showing tumor volume of mice bearing B16 melanoma tumors treated systemically three times every other day (arrows) with descending doses of antibody-combination as indicated or left untreated. SD shown. Student's T-test *, P<0.001; , P<0.01; *P<0.05. FIG. 4F is a graph of flow cytometry analyses of Stat3 activity. FIG. 4G is a graph of flow cytometry analyses of cell apoptosis. FIGS. 4F and 4G used single-cell suspensions prepared from tumors treated locally by the modified antibodies. FIG. 4H are images showing tumor homogenates prepared from the experiment described above for FIG. 4E subjected to immunoprecipitation of nucleoporin 50 (upper panel) or nucleoporin 153 (lower panel), followed by STAT3 Western blot to assess protein interaction. FIG. 4I is an image of an electrophoretic mobility shift assay (EMSA) showing effective STAT3 activity blockade by the phosphorothioated nucleic acid modified duo antibodies. Nuclear extracts were isolated from the same tumors as in FIG. 4E.

FIG. 5A are images of interaction between STAT3 and Exportin 7 as shown by Western blotting following co-immunoprecipitation using whole cell lysates from U251 human brain tumor cells. STAT3 protein precipitates were separated by SDS-PAGE and analyzed by Western blotting analysis to identify its interaction with various exportins as indicated. Whole cell lysates were included as control (right lane). FIG. 5B are images of confocal microscopy of STAT3-GFP fusion protein (upper panel) or NFkB subunit p65-GFP (lower panels) expressed in MEF cells and treated with an exportin 1/Crm1-specific inhibitor, leptomycin B, at the indicated concentrations and time points. Protein localization upon LMB treatment was assessed using confocal microscopy. Scale bar 10 mm.

FIG. 6A is an image depicting a couple of 3T3/v-Src cells expressing STAT3-YFP, one of which serves as a control while iFLAP is carried out in its neighboring cell using confocal microscopy. Scale 10 µm. FIG. 6B is a graph showing emission signal decoy of nuclear STAT3-YFP or STAT3-K685R-YFP expressed in 3T3/v-Src cells determined upon continuous cytoplasmic bleaching and recording nuclear YFP emission. Acquired YFP intensities were corrected and normalized using FLIP parameters.

FIG. 7A are images of confocal microscopy of Stat3-deficient MEFs transiently transfected with Stat3-WT-YFP and Stat3-K685R-YFP and stimulated with 10 ng/ml oncostatin M at the indicated time points. Nuclear retention of STAT3-WT-YFP and STAT3-K685RYFP was assessed using confocal microscopy. Scale bar 10 µm. FIG. 7B is a schematic showing nuclear egress kinetics of STAT3-WT-YFP and STAT3-K685R-YFP was analyzed by a digitonin-based fluorescence protease protection (FPP) assay, designed as shown in the scheme. FIG. 7C are images showing STAT3-WT-YFP (upper panel) or STAT3-K685R-YFP (lower panel) expressed in 3T3/v-Src transformed fibroblasts. Images of live cells were acquired upon digitonin administration at the indicated time points. Decoy of nuclear YFP emission is shown in intensity coded wrong color mode (black, high intensity; white, low intensity). Scale bar 10 μm.

FIG. 8A is a graph of tumor volume of MEF cell lines stably expressing STAT3-WT or STAT3-K685R engrafted in athymic nu/nu mice. FIG. 8B is a schematic representation of the NPC highlighting the location of nucleoporins 50 (Nup50) and 153 (Nup153) in the nuclear basket as indicated (left panel). Exportin 7 facilitates nuclear egress of STAT3 once it is recognized as a cargo by mediating physical interaction with nucleoporins of the inner basket (right panel). FIG. 8C are images of confocal microscopy of the interaction of STAT3-WT and STAT3-K685R with Nup50 (upper panel) and Nup153 (lower panel) in vivo assessed through indirect immunofluorescence STAT3 and nucleoporins. STAT3 and nucleoporin double-positive pixels were generated using the crosshair function giving an image mask of double-positive pixels. Scale bar 10 μm. FIG. 8D is a graph of the quantification of double-positive pixel comparing STAT3-WT (black) and STAT3-K685R (grey) in colocalization with Nup50, n=3 (left panel) and Nup153, n=3 (right panel).

FIG. 10A are confocal images showing efficient cytoplasmic delivery of targeting antibodies compared to non-targeting IgG control antibodies. Confocal images are of microsections of STAT3-GFP overexpressing MEF tumors showing antibody load and localization. Cytoplasmic localization of targeting antibodies is shown magnified (lower right corner) from a selected area (dashed line). Scale bar, 100 μm. Confocal microscopic images of tissue microsections showing renal clearance and systemic distribution of locally delivered antibodies. Scale bar, 100 μm. FIG. 10B is an image of a Western blot analysis following co-immunoprecipitation of STAT3 and nucleoporin 50 of tumor lysates show interrupted STAT3 nucleo-cytoplasmic shuttling upon intracellular delivery of targeting antibodies in vivo. FIG. 10C are images showing in vivo delivered targeting antibodies are stable at least 24 hours after administration. Western blotting following protein separation on SDSPAGE under non-reducing conditions show injected antibodies, which are rabbit immunoglobulins.

FIG. 11A is a graph showing tumor growth kinetics. FIG. 11B are images of Western blotting showing protein expression levels of angiogenic factors in tumors treated with control and anti-STAT3 and anti-exportin 7 antibodies. FIG. 11C are confocal images of tumor vasculatures as a result of antibody treatment as indicated. CD31+ cells are shown (left panels) and quantified (right panel); n=6. Student's T-test *, P<0.001; , P<0.01; *P<0.05. Scale bar 10 μm. FIG. 11D are images showing Western blotting reveals an increase in pro-apoptotic gene expression due to duo-antibody treatment. Lysates for Western blot were prepared from tumors treated as indicated. These experiments were repeated at least twice with similar results.

FIG. 12A are confocal microscopy images showing the localization of in vivo administered antibodies was assessed from the B16 tumor microsections stained for rabbit immunoglobulins. Scale bar 100 μm (left panel). FIG. 12B is a graph showing quantitation of antibodies retained in tumor tissues by mean fluorescence intensity per field of view in tumor microsections; non-targeting immunoglobulins (IgG, black), targeting STAT3/exportin 7 antibody combination (grey); n=3. FIG. 12C is a graph showing melanoma B16 tumors were grown in C57BL/6 mice and treated every other day with a combination of anti-STAT3/antiexportin 7 immunoglobulins, non-targeting IgG control, or left untreated as indicated, and tumor growth kinetics was monitored. Student's T-test *, P<0.001; , P<0.01; *P<0.05.

FIG. 15A are images of intravital-multiphoton microscopy performed to assess the intratumoral distribution of fluorescently labeled, phosphorothioated nucleic acid-modified antibodies upon local (s.c., upper middle and right panels) or systemic (i.v., lower panel) injections, respectively. The dot-like loci of accumulated oligo-modified antibodies are similar to those seen in in vitro studies (FIG. 1B). Phosphorothioated nucleic acid-modified antibodies homing to tumor tissue upon systemic delivery via retro-orbital route (i.v.) was assessed 2 hours after administration. Detection of dot-like foci of accumulated oligomodified antibodies (lower panel) in tumors. White dotted circles indicate cell nuclei. Scale bar, 50 μm. FIG. 15B are images showing Western blot analysis of tumor homing capacity and biostability of phosphorothioated nucleic acid-modified antibodies determined 8 days after final systemic administration. Different doses of phosphorothioated nucleic acid-modified antibodies were injected as indicated, every other day for three times. Tumors were harvested for analyses 8 days after last treatment. Tumor homogenates were subjected to non-reducing SDS-PAGE, followed by Western blot detection to assess the tumoral IgG load.

FIG. 16A are graphs of flow cytometry analysis of splenocytes treated for 2 hours at various concentrations of fluorescently labeled oligo-modified αStat3 antibody (αStat3oligoFITC) as indicated and dose-dependent internalization by immune cell populations, CD3+, CD11b+, and B220+, was determined. FIG. 16B are confocal laser scanning microscopy images of cellular internalization of 10 µg/ml oligo-modified antibodies (green) into indicated splenic immune cell populations. Nucleic acids were stained with Hoechst 33342. Differential interference contrast (DIC) shown. Scale bar, 10 µm.

FIG. 17A are graphs showing glioma cells treated with antibody conjugated with phosphorothioated oligonucleotide backbone (upper panels) compared to cells treated with antibody conjugated to oligonucleotide lacking thioation of the backbone (lower panels). Varying sequences of the conjugated oligonucleotides has negligible effects on cellular internalization of the antibodies. Two randomized oligonucleotide sequences were tested. FIG. 17B is an image showing varying phosphorothioated oligonucleotide sequences does not alter antigen recognition by the modified antibodies. U251 cells were treated with 10 µg of αStat3 antibody with indicated modifications. Whole cell lysates were prepared and agarose beads were added to induce immunoprecipitation. Precipitates were subjected to western blot analysis to determine antibody target recognition.

FIG. 23A is an image of a Western blot showing cell-penetration and target recognition by modified antibodies validated by an alternative immunoprecipitation. Whole cell lysates prepared from live cells incubated with modified STAT3 antibodies were analyzed by Western blotting probing for STAT3. FIG. 23B are graphs of flow cytometric analyses showing phosphorothioation of oligos (PS) facilitates cellular uptake of modified STAT3 antibody (top panel) independent of the nucleic acid sequence (second panel) or IgG species (third panel) or cell types (bottom panel). FIG. 23C is an image of a Western blot showing alternative IP followed by Western blotting confirms the flow cytometric data in FIG. 23B. STAT3 antibodies modified with phosphorothioated parental oligo (lane 2), non-phosphorothioated oligos (lane 3), and phosphorothioated sequence-scrambled versions of the parental oligo (lanes 4-6). FIG. 23D are confocal microscopic images of intracellular distribution of fluorescently labeled phosphorothioated-oligo-modified antibody. Scale bar, 20 µm and 10 µm, respectively. FIG. 23E is a flow cytometry graph showing intracellular uptake of modified and unmodified p-Src antibodies by murine 3T3/vSrc cells. FIG. 23F are confocal microscopy images indicating modified p-Src antibody colocalizes with its intracellular target protein p-Src. Lower panels show magnifications of indicated areas (dashed line boxes). Intracellular distribution of modified p-Src antibody along cell membrane is shown in intensity-coded wrong color mode. Scale bar, 10 µm. FIG. 23G is an image of a Western blot showing alternative immunoprecipitation followed by Western blotting to detect modified antibody-p-Src complex in 3T3/vSrc cells incubated with modified p-Src antibody or modified IgG antibody. Oligos and antibodies attached to oligos through vinylsulfone were used in the experiments for these figures.

FIG. 25A is a graph showing growth kinetics of tumors formed by transformed murine 3T3/vSrc cells treated locally every other day with indicated modified antibodies. SD shown, significance ) P≤0.01, P≤0.001. FIG. 25B are images of Western blots showing loss of p-Src and its downstream proteins in homogenates of 3T3/vSrc tumors treated as indicated were subjected to Western blotting and probed for activated pY416-Src, activated pY705-Stat3, as well as expression of several Src downstream genes, as indicated. Tubulin was probed as protein loading control. FIG. 25C is a graph showing modified p-Src antibodies effectively inhibit human A2058 melanoma growth in athymic nude mice. Tumor growth kinetics was assessed and tumors were treated locally every other day. SD shown, significance *) P≤0.001. FIG. 25D is an image of a Western blot showing homogenates of A2058 melanoma tumors treated as indicated were subjected to Western blotting under non-reducing conditions and probed for rabbit IgGs. Tubulin was included as a protein loading control. FIG. 25E are confocal microscopy images showing modified p-Src antibody treatment caused tumor vasculature disruption and tumor cell apoptosis in vivo as shown by immunohistochemistry combined with confocal microscopy. Tumor tissue sections of A2058 melanoma tumors treated as indicated were stained for fluoresceine (FITC), CD31+ tumor vasculature (upper panel) and cleaved caspase 3 (lower panel). Scale bar, 100 μm. FIG. 25F are graphs showing the quantification of the fluorescent signals. SD shown, significance ***) P≤0.001. A mixture of antibodies complexed/attached with oligos containing a S—S-hexanol group were used for the experiments in these figures.

FIGS. 26A and 26B are graphs showing human cervical cancer growth kinetics. Human CaSki cancer cells were engrafted in athymic nude mice and treated locally (FIG. 26A) or systemically (FIG. 26B) every other day with nothing, or modified IgG control or HPV16/18 E6 antibodies as indicated. SD shown, significance *) P≤0.05, ) P≤0.01, *) P≤0.001. FIG. 26C are microscopic images showing destruction of the CaSki tumors by the modified E6 antibodies. Shown are images stained by H&E and analyzed by brightfield microscopy. Scale bar, 100 μm. FIG. 26D is an images of a Western blot showing an increase of FADD protein level in the homogenates of CaSki cervical tumors treated with the modified E6 antibodies. Actin was probed as protein loading control. FIG. 26E is a graph showing RT-PCR indicating elevated expression of Caspase 8 mRNA in the CaSki tumors treated by the modified E6 antibodies. SD shown, significance ) P≤0.01. FIG. 26F are images showing immunostaining followed by confocal microscopy showing in vivo retention of the modified E6 antibody but not the control IgG antibody, resulting in loss of tumor vasculature and an increase in cleaved caspase 3. Tumor tissue sections of CaSki cervical tumors treated as indicated were stained for fluoresceine (FITC), CD31+ tumor vasculature and cleaved caspase 3. Scale bar, 100 μm. FIG. 26G are graphs showing quantitation of fluorescent signals. SD shown, significance ) P≤0.01, ***) P≤0.001. A mixture of antibodies with attached oligos containing a S—S-hexanol group were used for the experiments in these figures.

FIG. 27A are images showing modified antibodies to induce cytoplasmic relocation of nuclear accumulated Stat3 in vitro. Murine 3T3/vSrc cells expressing Stat3-mCherry fusion protein were treated with indicated antibodies. Stat3 compartmental localization was analyzed in living cells by confocal microscopy. Scale bar, 10 μm. FIG. 27B are graphs showing modified STAT3 and exportin 7 antibody treatment induces potent antitumor effects. B16 melanoma tumor growth kinetics in mice with indicated antibody treatments. Left panel: local injection; middle panel: local vs. systemic treatments, right panel: with three systemic treatments (arrows) in descending doses. SD shown, significance ) P≤0.01, *) P≤0.001. FIG. 27C is an image of a Western blot showing systemically treatment with modified STAT3/ exportin 7 antibodies abrogated Stat3 DNA-binding in tumors, as assessed by EMSA using nuclear extracts from the tumor homogenates in right panel of FIG. 27B. FIG. 27D is an image of a Western blotshowing prolonged in vivo stability of targeting antibodies administered systemically. Tumor homogenates from right panel of FIG. 27C were subjected to Western blotting under non-reducing conditions and probed for rabbit immunoglobulins. FIG. 27E are graphs showing tumor growth kinetics of human U87 glioma in athymic nude mice treated locally with indicated antibodies. FIG. 27F shows tumor growth kinetics of human U87 glioma in athymic nude mice treated systemically with indicated antibodies. SD shown, significance *) P≤0.05, ) P≤0.01, *) P≤0.001. FIG. 27G are images showing modified antibodies accumulated in tumors where the target resides and exerted antitumor effects. Athymic nude mice engrafted with human U251 glioma cells were treated locally or systemically every other day for three times or left untreated, as indicated. Tissue sections from the indicated organs (tumors) were stained for fluoresceine (FITC) to detect the modified antibodies, CD31+ for tumor vasculature and cleaved caspase 3 for tumor cell apoptosis. Inlays show magnifications of indicated areas (dashed line box). Scale bar, 100 μm. Oligos and antibodies attached to oligos through vinylsulfone were used in the experiments for FIGS. 27A, 27B, 27C, 27D, 27E, and 27G. For FIG. 27F, STAT3/Exp7 was oligos and antibodies attached with oligos through vinylsulfone, while for STAT3Rb/STAT3Ms and STAT3Rb/Rb a mixture of antibodies with attached oligos containing a S—S-hexanol group was used.

FIG. 33A is an image of a Western blot showing human U251 glioma cells incubated with 10 mg/ml of purified (P) aSTAT3 antibody either modified via vinylsulfone (VS) mediated attachment of phosphorothioated DNA-20meric-oligos (lane 1) or unmodified aSTAT3 alone (lane 3) or aSTAT3 and 500 pmol/ml phosphorothioated GpC1668, same as attached via VS (lane 4; lane 2 empty). FIG. 33B is an image of a Western blot showing human U251 cells were incubated with 10 mg/ml of unpurified (UP) aSTAT3 antibody modified via SSR (lane 2), unpurified (UP) aSTAT3 antibody modified via vinylsulfone (VS) mediated attachment of phosphorothioated oligos (lane 3) or purified (P) aSTAT3 antibody modified via vinylsulfone (VS) mediated attachment of phosphorothioated (lane 4); no antibody IgG added (lane 1).

DETAILED DESCRIPTION OF THE INVENTION

Figure 1A:
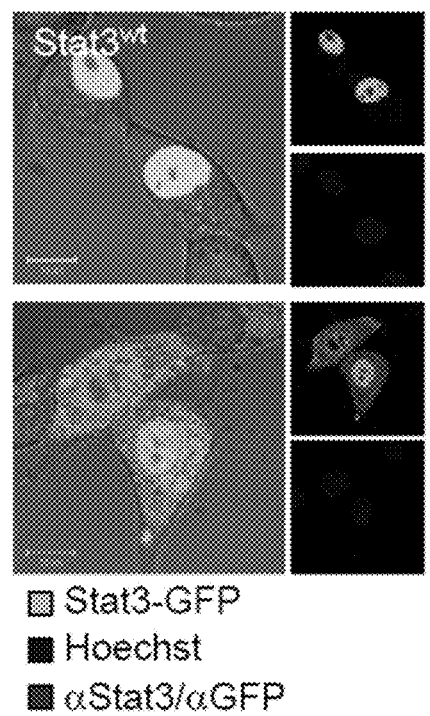
FIGS. 1A, 1B, 1C, 1D and 1E show targeting two discrete parts of a STAT3 fusion protein or STAT3/exportin 7 complex by antibodies retains STAT3 in the cytoplasm.

The terms "subject," "patient," "individual," etc. are not intended to be limiting and can be generally interchanged. That is, an individual described as a "patient" does not necessarily have a given disease, but may be merely seeking medical advice.

A "control" or "standard control" refers to a sample, measurement, or value that serves as a reference, usually a known reference, for comparison to a test sample, measurement, or value. For example, a test sample can be taken from a patient suspected of having a given disease (e.g. an autoimmune disease, inflammatory autoimmune disease, cancer, infectious disease, immune disease, or other disease) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophage-like synoviocytes, etc).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

The terms "dose" and "dosage" are used interchangeably herein. A dose refers to the amount of active ingredient given to an individual at each administration. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

As used herein, the terms "treat" and "prevent" may refer to any delay in onset, reduction in the frequency or severity of symptoms, amelioration of symptoms, improvement in patient comfort or function (e.g. joint function), decrease in severity of the disease state, etc. The effect of treatment can be compared to an individual or pool of individuals not receiving a given treatment, or to the same patient prior to, or after cessation of, treatment. The term "prevent" generally refers to a decrease in the occurrence of a given disease (e.g. an autoimmune, inflammatory, cancer, infectious, metabolic, developmental, cardiovascular, liver, intestinal, endocrine, neurological, or other disease) or disease symptoms in a patient. As indicated above, the prevention may be complete (no detectable symptoms) or partial, such that fewer symptoms are observed than would likely occur absent treatment.

By "therapeutically effective dose or amount" as used herein is meant a dose that produces effects for which it is administered (e.g. treating or preventing a disease). The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

The term "diagnosis" refers to a relative probability that a disease (e.g. an autoimmune, inflammatory autoimmune, cancer, infectious, immune, or other disease) is present in the subject. Similarly, the term "prognosis" refers to a relative probability that a certain future outcome may occur in the subject with respect to a disease state. For example, in the context of the present invention, prognosis can refer to the likelihood that an individual will develop a disease (e.g. an autoimmune, inflammatory autoimmune, cancer, infectious, immune, or other disease), or the likely severity of the disease (e.g., duration of disease). The terms are not intended to be absolute, as will be appreciated by any one of skill in the field of medical diagnostics.

"Nucleic acid" or "oligonucleotide" or "polynucleotide" or grammatical equivalents used herein means at least two nucleotides covalently linked together. The term "nucleic acid" includes single-, double-, multiple-stranded or branched DNA, RNA and analogs (derivatives) thereof. The term "phosphorothioate nucleic acid" refers to a nucleic acid in which one or more internucleotide linkages are through a phosphorothioate moiety (thiophosphate) moiety. The phosphorothioate moiety may be a monothiophosphate ($—P(O)_3(S)^{3-}—$) or a dithiophosphate ($—P(O)_2(S)_2^{3-}—$). In embodiments of all the aspects provided herein, the phosphorothioate moiety is a monothiophosphate ($—P(O)_3(S)^{3-}—$). That is, in embodiments of all the aspects provided herein, the phosphorothioate nucleic acid is a monothiophosphate nucleic acid. In embodiments, one or more of the nucleosides of a phosphorothioate nucleic acid are linked through a phosphorothioate moiety (e.g. monothiophosphate) moiety, and the remaining nucleosides are linked through a phosphodiester moiety (—P(O)$_4^{3-}$—). In embodiments, one or more of the nucleosides of a phosphorothioate nucleic acid are linked through a phosphorothioate moiety (e.g. monothiophosphate) moiety, and the remaining nucleosides are linked through a methylphosphonate linkage. In embodiments, all the nucleosides of a phosphorothioate nucleic acid are linked through a phosphorothioate moiety (e.g. a monothiophosphate) moiety.

Phosphorothioate oligonucleotides (phosphorothioate nucleic acids) are typically from about 5, 6, 7, 8, 9, 10, 12, 15, 25, 30, 40, 50 or more nucleotides in length, up to about 100 nucleotides in length. Phosphorothioate nucleic acids may also be longer in lengths, e.g., 200, 300, 500, 1000, 2000, 3000, 5000, 7000, 10,000, etc. As described above, in certain embodiments. the phosphorothioate nucleic acids herein contain one or more phosphodiester bonds. In other embodiments, the phosphorothioate nucleic acids include alternate backbones (e.g., mimics or analogs of phosphodiesters as known in the art, such as, boranophosphate, methylphosphonate, phosphoramidate, or O-methylphosphoroamidite linkages (see Eckstein, Oligonucleotides and Analogues: A Practical Approach, Oxford University Press). The phosphorothioate nucleic acids may also include one or more nucleic acid analog monomers known in the art, such as, peptide nucleic acid monomer or polymer, locked nucleic acid monomer or polymer, morpholino monomer or polymer, glycol nucleic acid monomer or polymer, or threose nucleic acid monomer or polymer. Other analog nucleic acids include those with positive backbones; non-ionic backbones, and nonribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. Phosphorothioate nucleic acids and phosphorothioate polymer backbones can be linear or branched. For example, the branched nucleic acids are repetitively branched to form higher ordered structures such as dendrimers and the like.

As used herein, a "phosphorothioate polymer backbone" is a chemical polymer with at least two phosphorothioate linkages (e.g. monothiophosphate) (e.g. linking together sugar subunits, cyclic subunits or alkyl subunits). The phosphorothioate polymer backbone may be a phosphorothioate sugar polymer, which is a phosphorothioate nucleic acid in which one or more (or all) of the chain of pentose sugars lack the bases (nucleobases) normally present in a nucleic acid. The phosphorothioate polymer backbone can include two or more phosphorothioate linkages. The phosphorothioate polymer backbone can include 5, 6, 7, 8, 9, 10, 12, 15, 25, 30, 40, 50 or more linkages and can contain up to about 100 phosphorothioate linkages. Phosphorothioate polymer backbones may also contain a larger number of linkages, e.g., 200, 300, 500, 1000, 2000, 3000, 5000, 7000, 10,000, and the like.

The phosphorothioate nucleic acids and phophorothioate polymer backbones may be partially or completely phosphorothioated. For example, 50% or more of the interneucleotide linkages of a phosphorothioate nucleic acid can be phosphorothioate linkages. Optionally, 5%, 10%, 15%, 20%, 25%, 30%, 35%, 40%, 45%, 50%, 55%, 60%, 65%, 70%, 75%, 80%, 85%, 90%, 95%, or 99% of the internucleotide linkages of a phosphorothioate nucleic acid are phosphorothioate linkages. Optionally, 50%, 55%, 60%, 65%, 70%, 75%, 80%, 85%, 90%, 95%, or 99% of the internucleotide linkages of a phosphorothioate nucleic acid are phosphorothioate linkages. Optionally, 75%, 80%, 85%, 90%, 95%, or 99% of the internucleotide linkages of a phosphorothioate nucleic acid are phosphorothioate linkages. Optionally, 90%, 95%, or 99% of the internucleotide linkages of a phosphorothioate nucleic acid are phosphorothioate linkages. In embodiments, the remaining internucleotide linkages are phosphodiester linkages. In embodiments, the remaining internucleotide linkages are methylphosphonate linkages. Optionally, 100% of the internucleotide linkages of the phosphorothioate nucleic acids are phosphorothioate linkages. Similarly, 5%, 10%, 15%, 20%, 25%, 30%, 35%, 40%, 45%, 50%, 55%, 60%, 65%, 70%, 75%, 80%, 85%, 90%, 95%, or 99%, of the intersugar linkages in a phosphorothioate polymer backbone can be phosphorothioate linkages. Optionally, 50%, 55%, 60%, 65%, 70%, 75%, 80%, 85%, 90%, 95%, or 99%, of the intersugar linkages in a phosphorothioate polymer backbone can be phosphorothioate linkages. Optionally, 75%, 80%, 85%, 90%, 95%, or 99%, of the intersugar linkages in a phosphorothioate polymer backbone can be phosphorothioate linkages. Optionally, 90%, 95%, or 99%, of the intersugar linkages in a phosphorothioate polymer backbone can be phosphorothioate linkages. In embodiments, the remaining internucleotide linkages are phosphodiester linkages. In embodiments, the remaining internucleotide linkages are methylphosphonate linkages. Optionally, 100% of the intersugar linkages of the phosphorothioate polymer backbone are phosphorothioate linkages.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism. An "inhibitory nucleic acid" is a nucleic acid (e.g. DNA, RNA, polymer of nucleotide analogs) that is capable of binding to a target nucleic acid (e.g. an mRNA translatable into a protein) and reducing transcription of the target nucleic acid (e.g. mRNA from DNA) or reducing the translation of the target nucleic acid (e.g. mRNA) or altering transcript splicing (e.g. single stranded morpholino oligo).

Figure 19:
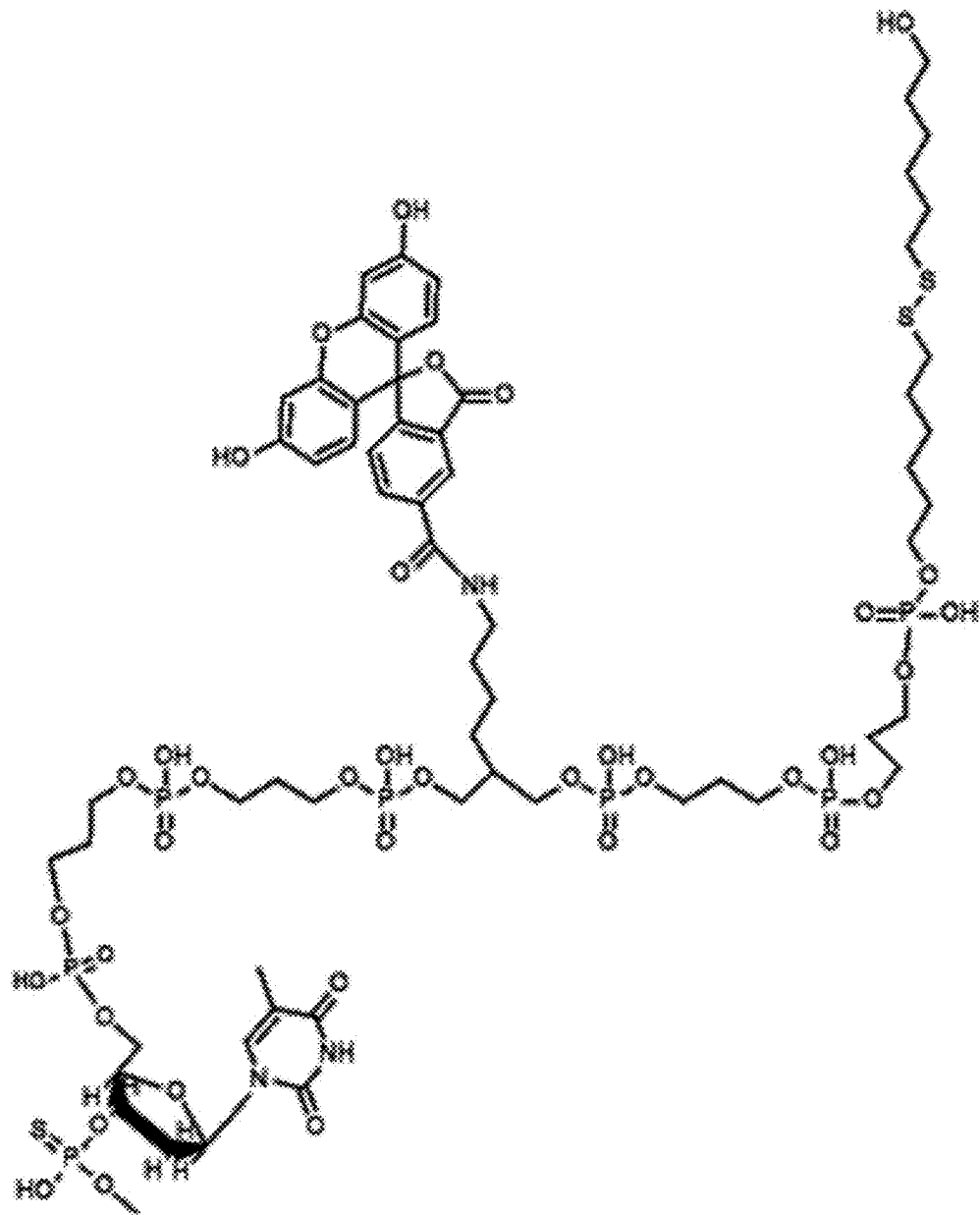
FIG. 19 is a schematic of the structure of an exemplary phosphorothioate nucleic acid with a moiety having the formula —S—S—R. One phosphorothioate nucleic acid base linked to the moiety is shown for purposes of illustration of the attachment point for phosphorothioate nucleic acid sequences. In this case, the R is hexanol and a linker moiety (having phosphodiester propyl repeating monomer units) links the —SSR to the remainder of the phosphorothioate nucleic acid.
Figure 20:
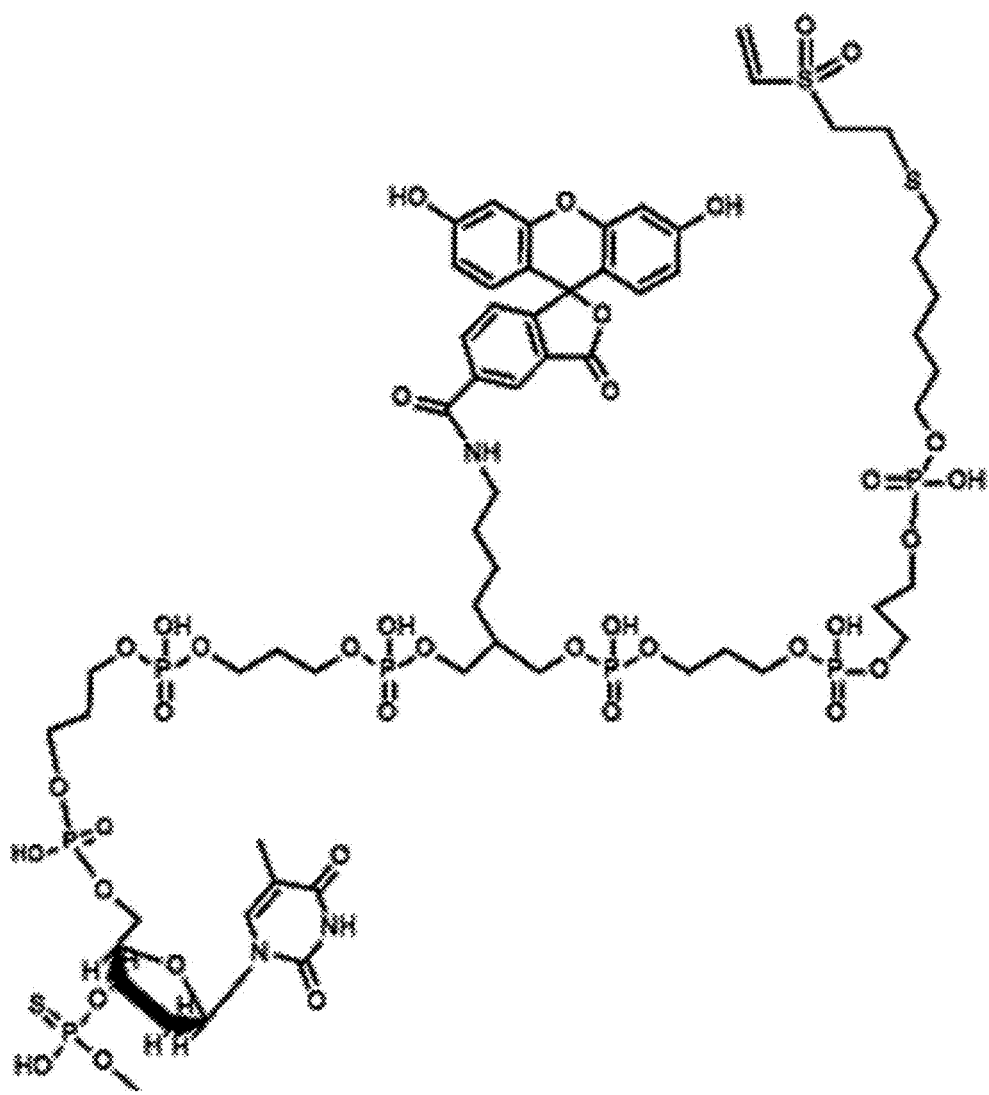
FIG. 20 shows the structure of an exemplary phosphorothioate nucleic acid with a vinyl sulfone (VS) reactive moiety and a linker moiety (having phosphodiester propyl repeating monomer units) that links the VS to the remainder of the phosphorothioate nucleic acid. One phosphorothioate nucleic acid base linked to the moiety is shown for purposes of illustration of the attachment point for phosphorothioate nucleic acid sequences.

The phosphorothioate nucleic acids and phosphorothioate polymer backbones provided herein can include one or more reactive moieties, e.g., a covalent reactive moiety. A reactive moiety may be attached to the remainder of the phosphorothioate nucleic acids and phosphorothioate polymer backbones using any appropriate linker, such as a polymer linker known in the art (as shown in FIGS. 19 and 20, or alternatively a polyethylene glygcol linker or equivalent). The linker may, in embodiments, include (i.e. be attached to) a detectable label as described herein. As used herein, the term "covalent reactive moiety" refers to a chemical moiety capable of chemically reactive with an amino acid of a non-cell penetrating protein, as described herein, to form a covalent ond and, thus, a conjugate as provided herein.

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer backbone includes a detectable label, as disclosed herein and generally known in the art.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

The term "recombinant" when used with reference, e.g., to a cell, or nucleic acid, protein, or vector, indicates that the cell, nucleic acid, protein or vector has been modified by or is the result oflaboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The P388 leukemia model is widely accepted as being predictive of in vivo anti-leukemic activity. It is believed that a compound that tests positive in the P388 assay will generally exhibit some level of anti-leukemic activity in vivo regardless of the type of leukemia being treated. Accordingly, the present application includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, and carcinoma *villosum*.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

As used herein, an "autoimmune disease" refers to a disease or disorder that arises from altered immune reactions by the immune system of a subject, e.g., against substances tissues and/or cells normally present in the body of the subject. Autoimmune diseases include, but are not limited to, arthritis, rheumatoid arthritis, psoriatic arthritis, juvenile idiopathic arthritis, scleroderma, systemic scleroderma, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, inflammatory bowel disease, Addison's disease, Vitiligo, asthma, and allergic asthma.

As used herein, an "inflammatory disease" refers to a disease or disorder associated with abnormal or altered inflammation. Inflammation is a biological response initiated by the immune system as part of the healing process in response to a pathogen, damaged cells or tissues or irratants. Chronic inflammation can lead to a variety of diseases. Inflammatory diseases include, but are not limited to, atherosclerosis, allergies, asthma, rheumatoid arthritis, transplant rejection, celiac disease, chronic prostatitis, inflammatory bowel diseases, pelvic inflammatory diseases, and inflammatory myopathies.

As used herein, "metabolic disorders" refer to diseases or disorders involving abnormal metabolism of a variety of molecules and substances including, for example, carobydrates, amino acids, organic acids. Metabolic disorders include, but are not limited to, disorders of carbohydrate metabolism, e.g., glycogen storage disease, disorders of amino acid metabolism, e.g., phenylketonuria, maple syrup urine disease, glutaric acidemia type 1, urea cycle disorder or urea cycle defects, e.g., carbamoyl phosphate synthetase I deficiency, disorders of organic acid metabolism (organic acidurias), e.g., alcaptonuria, disorders of fatty acid oxidation and mitochondrial metabolism, e.g., medium-chain acyl-coenzyme A dehydrogenase deficiency, disorders of porphyrin metabolism, e.g., acute intermittent *porphyria*, disorders of purine or pyrimidine metabolism, e.g., Lesch-Nyhan syndrome, disorders of steroid metabolism, e.g., lipoid congenital adrenal hyperplasia, congenital adrenal hyperplasia, disorders of mitochondrial function, e.g., Kearns-Sayre syndrome, disorders of peroxisomal function, e.g., Zellweger syndrome, and lysosomal storage disorders, e.g., Gaucher's disease, and Niemann Pick disease.

As used herein, "developmental disorders" refer to diseases or disorders often originating in childhood associated with language disorders, learning disorders, motor disorders and neurodevelopmental disorders. Examples include, but are not limited to, autism spectrum disorders and attention deficit disorders.

As used herein, "cardiovascular diseases" refer to diseases associated with the heart, blood vessels or both. Cardiovascular diseases include, but are not limited to, coronary heart disease, cardiomyopathy, hypertensive heart disease, heart failure, cardiac dysrhythmias, inflammatory heart disease, peripheral arterial disease, cerebrovascular disease and inflammatory heart disease.

As used herein, "liver diseases" refer to diseases associated with the abnormalities in the liver and/or liver function. Liver diseases include, but are not limited to, hepatitis, alcoholic liver disease, fatty liver disease, cirrhosis, Budd-Chiari syndrome, Gilbert's syndrome and cancer.

As used herein, the term "intestinal disease" refers to diseases or disorders associated with abnormalities in the intestine (small or large). Intestinal diseases include, but are not limited to, gastroenteritis, colitis, ileitis, appendicitis, coeliac disease, Chron's disease, enteroviruses, irritable bowel syndrome, and diverticular disease.

As used herein, the term "endocrine disease" refers to diseases or disorders of the endocrine system including endocrine gland hyposecretion, endocrine gland hypersecretion and tumors. Endocrine diseases include, but are not limited to, Addison's disease, diabetes, Conn's syndrome, Cushing's syndrome, glucocorticoid remediable aldosteronism, hypoglycemia, hyperthyroidism, hypothyroidism, thyroiditis, hypopituitarism, hypogonadism and parathyroid gland disorders.

As used herein, the term "neurological disorder" refers to diseases or disorders of the bodies nervous system including structural, biochemical or electrical abnormalities. Neurological disorders include, but are not limited to, brain damage, brain dysfunction, spinal cord disorders, peripheral neuropathies, cranial nerve disorders, autonomic nervous system disorders, seizure disorders, movement disorders, e.g., Parkinson's disease and Multiple Sclerosis, and central neuropathies.

As used herein, the term "infectious disease" refers to diseases or disorders associate with infection, presence and/or growth of a pathogenic agent in a host subject. Infectious pathogenic agents include, but are not limited to, viruses, bacteria, fungi, protozoa, multicellular parasites and aberrant proteins, e.g., prions. Viruses associated with infectious disease include but are not limited to, herpes simplex viruses, cytomegalovirus, Epstein-Barr virus, Varicella-zoster virus, herpesviruses, Vesicular stomatitis virus, Hepatitis viruses, Rhinovirus, Coronavirus, Influenza viruses, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Simian Immunodeficiency viruses, Human Immunodeficiency viruses. Bacteria associated with infectious disease include, but are not limited to, *M. tuberculosis, Salmonella* species, *E. coli, Chlamydia* species, *Staphylococcus* species, *Bacillus* species, and *Pseudomonas* species.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

As used herein, the terms "cell-penetrating" or "cell-penetration" refer to the ability of a molecule (e.g. a protein) to pass from the extracellular environment into a cell in a significant or effective amount. Thus, a cell-penetrating conjugate is a molecule that passes from the extracellular environment, through the membrane, and into a cell.

As used herein, the terms "non-cell penetrating" or "non-cell penetration" refers to the inability of a molecule to pass from the extracellular environment into a cell in a significant or effective amount. Thus, non-cell penetrating peptides or proteins generally are not capable of passing from the extracellular environment, through the cell membrane, and into a cell in order to achieve a significant biological effect on a population of cells, organ or organism. The term does not exclude the possibility that one or more of the small number of peptides or proteins may enter the cell. However, the term refers to molecules that are generally not able to enter a cell from the extracellular environment to a significant degree. Examples of non-cell penetrating molecules and substances include, but are not limited to, large molecules such as, for example, high molecular weight proteins. Peptides or proteins can be determined to be non-cell penetrating using methods known to those of skill in the art. By way of example, a peptide or protein can be fluorescently labeled and the ability of the peptide or protein to pass from the extracellular environment into the cell can be determined in vitro by flow cytometric analysis or confocal microscopy. In some embodiments, a "non-cell penetrating protein" refers to a protein that penetrates a cell at least about 2, 3, 4, 5, 6, 7, 8, 9, 10, 20, 30, 40, 50, 60, 70, 80, 90, 100, 200, 300, 400, 500, 600, 700, 800, 900, 1000, 10,000 or 100,000 fold less than the same protein attached to a phosphorothioate nucleic acid or phosphorothioate polymer backbone. In some embodiments, a "non-cell penetrating protein" refers to a protein that does not measurably penetrate a cell.

As used herein, "molecular weight" (M.W.) or "molecular mass" refers to the sum of the atomic weights of all the atoms in a molecule. With respect to molecules, a molecule with a high molecular weight typically has a molecular weight of 25 kDa or more. By way of example, a high molecular weight protein can have a M.W. from about 25 kDa to 1000 kDa or more.

As used herein, the term "intracellular" means inside a cell. As used herein, an "intracellular target" is a target, e.g., nucleic acid, polypeptide or other molecule (e.g., carbohydrate) that is located inside of a cell and is a target to which the non-cell penetrating proteins provided herein bind. Binding can be direct or indirect. Optionally, the non-cell penetrating protein selectively binds the intracellular target. By selectively binds, selectively binding, or specifically binding refers to the agent (e.g., a non-cell penetrating protein) binding one agent (e.g., intracellular target) to the partial or complete exclusion of other agents. By binding is meant a detectable binding at least about 1.5 times the background of the assay method. For selective or specific binding such a detectable binding can be detected for a given agent but not a control agent. Alternatively, or additionally, the detection of binding can be determined by assaying the presence of down-stream molecules or events.

As used herein, the term "conjugate" refers to the association between atoms or molecules. The association can be direct or indirect. For example, a conjugate between a nucleic acid and a protein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). Optionally, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the phosphorothioate nucleic acid and phosphorothioate backbone polymer are non-covalently attached to the protein through a non-covalent chemical reaction between a component of the phosphorothioate nucleic acid and phosphorothioate backbone polymer (e.g. a monothiophosphate) and a component of the protein (e.g. an amino acid). In other embodiments, the phosphorothioate nucleic acid or phosphorothioate backbone polymer include one or more reactive moieties, e.g., a covalent reactive moiety, as described herein (e.g., an amino acid reactive moiety such as a vinyl sulfone moiety ($-S(O)_2CH=CH_2$).

Useful reactive moieties including covalent reactive moieties or functional groups used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

Figure 21:
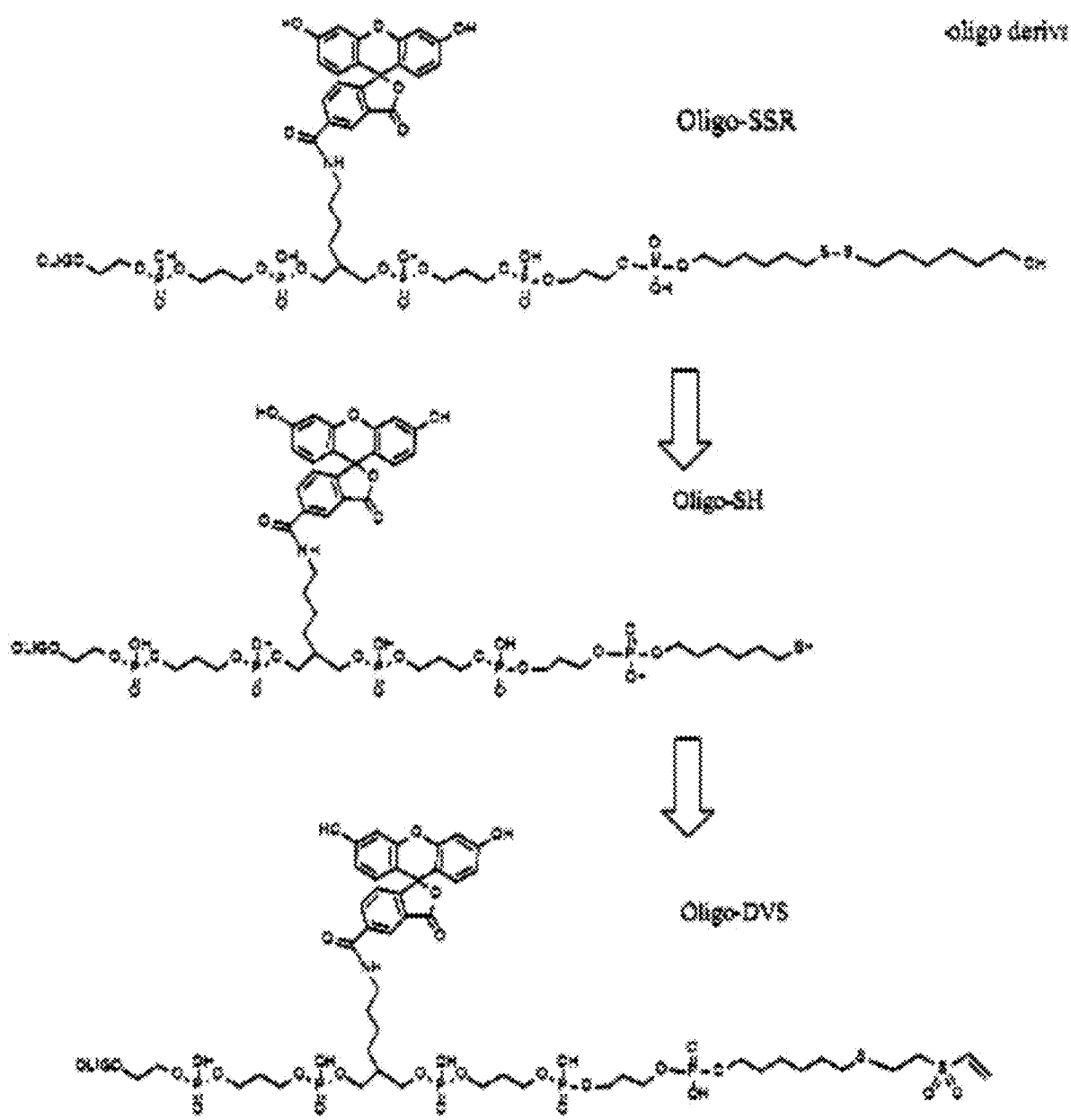
FIG. 21 is a schematic showing an exemplary method for the synthesis of a phosphorothioate nucleic acid with a vinyl sulfone from a phosphorothioate nucleic acid having a moiety of the formula —S—S—R.
Figure 22:
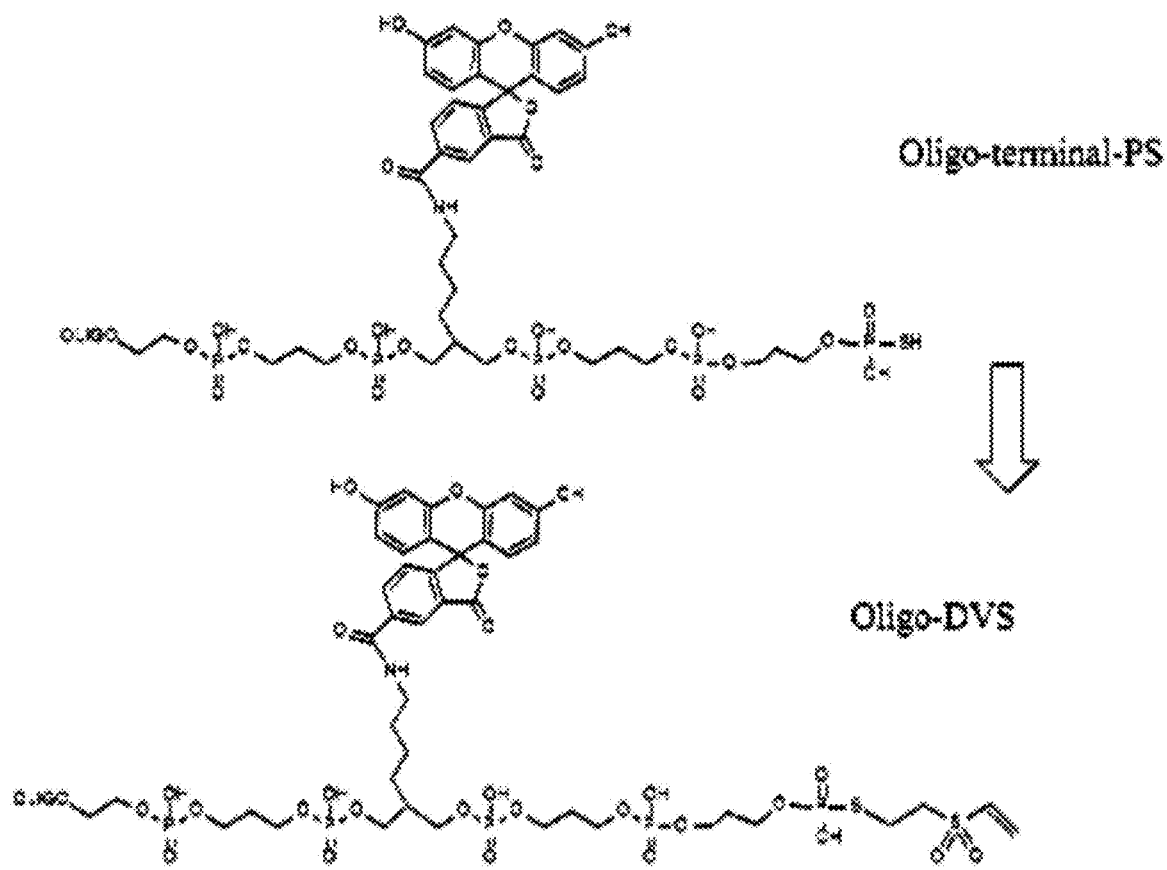
FIG. 22 is a schematic showing an exemplary method for the synthesis of a nucleic acid having a vinyl sulfone reactive moiety from a nucleic acid with a terminal phosphate (PS).

The reactive functional groups can be chosen such that they do not participate in, or interfere with, the chemical stability of the proteins described herein. By way of example, the nucleic acids can include a vinyl sulfone or other reactive moiety. FIG. 21 is a schematic showing the formation of a nucleic acid with a vinyl sulfone reactive moiety from a nucleic acid with an S—S—R moiety, wherein R is —$(CH_2)_6$—OH. FIG. 22 is a schematic showing the formation of a nucleic acid with a vinyl sulfone from a nucleic acid with a terminal phosphate (PS).

Provide herein are cell penetrating conjugates. The conjugate includes a non-cell penetrating protein attached to a phosphorothioate nucleic acid, wherein the phosphorothioate nucleic acid enhances intracellular delivery of the non-cell penetrating protein. Optionally, each phosphorothioate nucleic acid comprises a nonspecific sequence. In some embodiments, the non-cell penetrating protein is attached to a phosphorothioate polymer backbone. Thus, provided herein are cell penetrating conjugates including a non-cell penetrating protein attached to a phosphorothioate polymer backbone, wherein the phosphorothioate polymer backbone enhances intracellular delivery of the non-cell penetrating protein. As discussed above, polymer backbones contain the same structure (i.e., contains a chain of two or more sugar residues linked together) as a nucleic acid sequence with the exception that the polymer backbone lacks the bases normally present in a nucleic acid sequence. Also provided are cells comprising the cell penetrating conjugates.

The phosphorothioate nucleic acids or phosphorothioate polymer backbones can be of any appropriate length. Optionally, each phosphorothioate nucleic acid or phosphorothioate polymer backbone is independently 10, 20, 30, 40, 50, 60, 70, 80, 90, 100 or more nucleic acid residues or sugar residues in length. Optionally, each phosphorothioate nucleic acid or phosphorothioate polymer backbone is independently from 10 to 30 residues in length. Thus, the length of each nucleic acid or polymer backbone can be at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleic acid residues or sugar residues in length. Optionally, each phosphorothioate nucleic acid or phosphorothioate polymer backbone is independently from 5 to 50, 10 to 50, 15 to 50, 20 to 50, 25 to 50, 30 to 50, 35 to 50, 40 to 50, 45 to 50, 5 to 75, 10 to 75, 15 to 75, 20 to 75, 25 to 75, 30 to 75, 35 to 75, 40 to 75, 45 to 75, 50 to 75, 55 to 75, 60 to 75, 65 to 75, 70 to 75, 5 to 100, 10 to 100, 15 to 100, 20 to 100, 25 to 100, 30 to 100, 35 to 100, 40 to 100, 45 to 100, 50 to 100, 55 to 100, 60 to 100, 65 to 100, 70 to 100, 75 to 100, 80 to 100, 85 to 100, 90 to 100, 95 to 100, or more residues in length. Optionally, each phosphorothioate nucleic acid or phosphorothioate polymer backbone is independently from 10 to 15, 10 to 20, 10 to 30, 10 to 40, or 10 to 50 residues in length.

Optionally, the length of one phosphorothioate nucleic acid or phosphorothioate polymer backbone differs from another phosphorothioate nucleic acid or phosphorothioate polymer backbone. By way of example, if two phosphorothioate nucleic acids or phosphorothioate polymer backbones are attached to a non-cell penetrating protein the first phosphorothioate nucleic acid or phosphorothioate polymer backbone can be of one length (e.g., 22 residues) and the second phosphorothioate nucleic acid or phosphorothioate polymer backbone can be of a different length (e.g. 25 residues). Thus, if a plurality of phosphorothioate nucleic acids and phosphorothioate polymer backbones are attached to a non-cell penetrating protein the phosphorothioate nucleic acids and phosphorothioate polymer backbones can have a number of different lengths, e.g., ranging from 10 to 30 residues in length.

Optionally, a plurality of phosphorothioate nucleic acids or phosphorothioate polymer backbones are attached to the non-cell penetrating protein. Optionally, 1, 2, 3, 4, 5, 6, 7, 8, 9, 10, 15, 20, 25, or more phosphorothioate nucleic acids or phosphorothioate polymer backbones are attached to the protein. In embodiments, the attachment is covalent. The attachment may be non-covalent. The phosphorothioate nucleic acids or phosphorothioate polymer backbones can be independently attached to a lysine, arginine, cysteine, or histidine of the non-cell penetrating protein. Optionally, each phosphorothioate nucleic acid or phosphorothioate polymer backbone is attached to a cysteine of the protein. Optionally, the protein comprises phosphorothioate nucleic acids or phosphorothioate polymer backbones attached to 10%, 25%, 50%, 75%, 90%, 95%, or 100% of the lysines, arginines, cysteines, histidines, or combinations thereof of the protein.

As discussed above, the nucleic acids, e.g., the phosphorothioate nucleic acids or phosphorothiate polymer backbones can be attached to the non-cell penetrating proteins through a variety of mechanisms. The phosphorothioate nucleic acid or phosphorothioate polymer backbone can be covalently or non-covalently attached to the non-cell penetrating protein. Optionally, when a plurality of phosphorothioate nucleic acids or phosphorothioate polymer backbones are attached to the protein, each of the plurality can be covalently or non-covalently attached to the protein. Optionally, the protein comprises covalently and non-covalently attached phosphorothioate nucleic acids or phosphorothioate polymer backbones. Optionally, the protein comprises covalently attached phosphorothioate nucleic acids or phosphorothioate polymer backbones and does not comprise non-covalently attached phosphorothioate nucleic acids or phosphorothioate polymer backbones. Optionally, the protein comprises non-covalently attached phosphorothioate nucleic acids or phosphorothioate polymer backbones and does no comprise covalently attached phosphorothioate nucleic acids or phosphorothioate polymer backbones. Each of the phosphorothioate nucleic acids or phosphorothioate polymer backbones may contain a reactive moiety, e.g., an amino acid reactive moiety or covalent reactive moiety, that facilitates attachment of the phosphorothioate nucleic acid or phosphorothioate polymer backbone to the non-cell penetrating protein. Thus, the phosphorothioate nucleic acids or phosphorothioate polymer backbones can be attached to the protein through a reactive moiety.

The cell penetrating conjugates provided herein may be made by contacting an unattached non-cell penetrating protein with an unattached phosphorothioate nucleic acid or unattached phosphorothioate polymer backbone and allowing the unattached phosphorothioate nucleic acid or unattached phosphorothioate polymer backbone to covalently bind to an amino acid of the unattached non-cell penetrating protein thereby attaching and forming said cell penetrating conjugate. The use of the term "unattached" as used within the context of making the cell penetrating conjugates is intended to indicate the state of the non-cell penetrating protein, phosphorothioate nucleic acid or phosphorothioate polymer backbone prior to attachment and formation of the conjugate. That is, the term "unattached" indicates that the non-cell penetrating protein, phosphorothioate nucleic acid or phosphorothioate polymer backbone are free and in their unbound state relative to their associated form within the cell penetrating conjugate.

In embodiments, the phosphorothioate nucleic acid or phosphorothioate polymer backbone includes a covalent reactive moiety. As described above, the covalent reactive moiety may reactive with a lysine, arginine, cysteine or histidine of the protein (e.g. with the amino acid side chains). In embodiments, the covalent reactive moiety is reactive with a cysteine. The covalent reactive moiety may be a vinyl sulfone.

In embodiments, the cell penetrating conjugates provided herein may be made by made by contacting an unattached non-cell penetrating protein with an unattached phosphorothioate nucleic acid or unattached phosphorothioate polymer backbone and allowing the unattached phosphorothioate nucleic acid or unattached phosphorothioate polymer backbone to bind to the unattached non-cell penetrating protein thereby attaching and forming the cell penetrating conjugate.

In this or other embodiments provided herein, the phosphorothioate nucleic acid, phosphorothioate polymer backbone, unattached phosphorothioate nucleic acid or unattached phosphorothioate polymer backbone may include a substituent having the formula —S—S—$(CH_2)_z$—OH, wherein z is an integer from 1 to 50, 1 to 40, 1 to 30, 1 to 20, 1 to 10 or 1 to 5. The variable z may be 1, 2, 3, 4, 5, 6, 7, 8, 9 or 10. The variable z may be 1, 2, 3, 4, 5, 6, 7, 8 or 9. The variable z may be 1, 2, 3, 4, 5, 6, 7 or 8. The variable z may be 1, 2, 3, 4, 5, 6 or 7. The variable z may be 1, 2, 3, 4, 5, or 6.

In embodiments, where an unattached phosphorothioate nucleic acid or unattached phosphorothioate polymer backbone is contacted with an non-cell penetrating protein, the contacting is performed under reducing conditions. The contacting may also be performed at a pH less than about 9.0, 8.5, 8.0, 7.9, 7.8, 7.7, 7.6, 7.5, 7.4, 7.3, 7.2, 7.1 or 7.0. In embodiments, the pH is less than 8.0. In embodiments, the pH is less than 7.9. In embodiments, the pH is less than 7.8. In embodiments, the pH is less than 7.7. In embodiments, the pH is less than 7.6. In embodiments, the pH is less than 7.5. In embodiments, the pH is less than 7.4. In embodiments, the pH is less than 7.3. In embodiments, the pH is less than 7.2. In embodiments, the pH is less than 7.1. In embodiments, the pH is less than 7.0. In embodiments, the contacting is performed under reducing conditions and at a pH less than about 8.0 (e.g. about 7.9, 7.8, 7.7, 7.6, 7.5, 7.4, 7.3, 7.2, 7.1 or 7.0).

In embodiments, the unattached phosphorothioate nucleic acid or unattached phosphorothioate polymer backbone is present in molar excess of the unattached non-cell penetrating protein (e.g. at the time of contacting). The molar excess may be an excess of about 2 to 100 fold, such as about 2, 3, 4, 5, 6, 7, 8, 9, 10, 11, 12, 13, 14, 15, 1, 6 17, 18, 19, 20, 25, 30, 35, 40, 45, 50, 55, 60, 65, 70, 75, 80, 85, 90, 95 or 100. In embodiments, the molar excess from about 2 to 90, 3 to 80, 4 to 70, 5 to 60, 6 to 50, 7 to 40, 8 to 30, 9 to 30, 10 to 30, 15 to 25 or about 20. In embodiments, the molar excess is about 10, 20 or 30. In embodiments, the molar excess is about 20. In embodiments, the molar excess is at least about 5. In embodiments, the molar excess is at least about 10. In embodiments, the molar excess is at least about 15. In embodiments, the molar excess is at least about 20.

In embodiments of any aspect provided herein, phosphorothioate nucleic acid or phosphorothioate polymer backbone includes a reactive moiety having the formula S—S—R, where R is a protecting group. Optionally, R is a hexanol (a monovalent substituent). As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

The provided cell penetrating conjugate may be made by contacting the non-cell penetrating protein with the phosphorothioate nucleic acid and allowing the phosphorothioate nucleic acid to bind to the protein. By way of example, the provided cell penetrating conjugate may be made by contacting the non-cell penetrating protein with the phosphorothioate nucleic acid and allowing the phosphorothioate nucleic acid to covalently bind to an amino acid of the protein. Optionally, the phosphorothioate nucleic acid comprises a reactive moiety. By way of example, the reactive moiety can a vinyl sulfone or a reactive moiety with the formula S—S—R, as described above. Optionally, R is a hexanol, for example, 1-hexanol. Exemplary phosphorothioate nucleic acids having a reactive moiety of the formula S—S—R is shown in FIG. 19 and an exemplary phosphorothioate nucleic acid having a vinyl sulfone reactive moiety is shown in FIG. 20. The contacting is, optionally, performed under reducing conditions but can be performed under other conditions known to those of skill in the art. Optionally, the phosphorothioate nucleic acid is present in molar excess of the non-cell penetrating protein.

Optionally, the non-cell penetrating protein is a high molecular weight protein. The non-cell penetrating protein optionally has a molecular weight of at least about 25 kD or greater. In some embodiments, the non-cell penetrating protein has a molecular weight of at least about 25 to at least about 750 kD. Thus, the non-cell penetrating protein can have a molecular weight of at least about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, or more kilodaltons (kD). Optionally, the non-cell penetrating protein has a molecular weight from at least about 25 to 100 kD, at least about 25 to 150 kD, at least about 25 to 200 kD, at least about 25 to 250 kD, at least about 25 to 300 kD, at least about 25 to 350 kD, at least about 25 to 400 kD, at least about 25 to 450 kD, at least about 25 to 500 kD, at least about 25 to 550 kD, at least about 25 to 600 kD, at least about 25 to 650 kD, at least about 25 to 700 kD or at least above 25 to 750 kD.

Optionally, the non-cell penetrating protein is an antibody. As discussed in more detail above, antibodies can be full length antibodies such as IgG, IgA, IgM, IgD or IgE antibodies or fragments thereof. Optionally, the antibody is an IgG antibody or a fragment thereof. Optionally, the antibody is an Fv fragment or a humanized antibody. Thus, provided are antibodies attached to a phosphorothioate nucleic acid or polymer backbone, wherein the phosphorothioate nucleic acid or polymer backbone enhances delivery of the antibody into a cell. Optionally, the antibody is a therapeutic antibody, i.e., an antibody used in the treatment of disease. Thus, also provided are therapeutic antibodies attached to one or more phosphorothioate nucleic acids or polymer backbones wherein the antibody binds an intracellular target.

Optionally, the non-cell penetrating protein binds an intracellular target. The intracellular target can be a therapeutic target or a diagnostic target or other target of interest located intracellularly, e.g., a target or structure, e.g., histone, to be imaged, e.g., by confocal microscopy. Thus, provided are cell penetrating conjugates bound to an intracellular target. Optionally, the intracellular target is a target of a disease selected from the group consisting of autoimmune disease, inflammatory disease, metabolic disorder, developmental disorder, cardiovascular disease, liver disease, intestinal disease, infectious disease, endocrine disease, neurological disorder, and cancer. The target of a disease can be a diagnostic target or therapeutic target or other target of interest associated with the disease. Exemplary intracellular targets of cancer include, but are not limited to, STAT (e.g., STAT3), NFκB, PKB/Akt, Myc family members, steroid hormone receptors (e.g., estrogen receptor), ligands of steroid hormone receptors (e.g., cyclin D1), receptor tyrosine kinases (RTKs), HER2, EGFR, VEGFR, PDGFR, Src family members, Ras, Abl, BCR-Abl, NPM-Alk, Janus kinases (JAKs), Brutun's tyrosine kinase (BTK), and viral oncoproteins (e.g., an EBV protein, or an HPV protein, e.g., E6 and E7). Optionally, the intracellular target of the infectious disease is a viral protein or viral transcript. Thus, the intracellular target can be a viral protein or viral transcript of a human immunodeficiency virus (HIV), influenza virus, herpes simplex cirus, epstein barr virus, cytomegalovirus, human papilloma virus, or hepatitis virus. Optionally, the intraceullar target is a DNA binding protein including, but not limited to, a transcription factor, a transcriptional enhancer, a transcriptional repressor, a histone or post-translationally modified histone. Optionally, the intracellular target is epigenetically modified DNA, e.g., methylated or hydroxymethylated cytosine (5mC or 5hmC), 5-formylcytosine (5fC) and 5-carboxylcytosine (5caC). Optionally, the intracellular target is a nucleic acid, e.g., an RNA transcript or a nucleic acid. For example, the intracellular target may be the nucleic acid of an infectious pathogen, e.g., a parasite, virus or bacteria. Optionally, the intracellular target is a signaling molecule or transcription factor. Optionally, the signaling molecule is a phosphatase or kinase. Optionally, the intracellular target is a cancer target or located within a cancer cell. Optionally, the intracellular target is a STAT, e.g., STAT3 or exportin 7. Optionally, the non-cell penetrating protein further comprises a label, a small molecule or a functional nucleic acid attached to the protein.

Provided are a plurality of cell penetrating conjugates comprising non-cell penetrating proteins attached to phosphorothioate nucleic acids or phosphorothioate polymer backbones, wherein the phosphorothioate nucleic acids or phosphorothioate polymer backbones enhance intracellular delivery of the non-cell penetrating proteins. The phosphorothioate nucleic acids or phosphorothioate polymer backbones are covalently or non-covalently attached to the non-cell penetrating proteins. Optionally, the plurality comprises covalently attached phosphorothioate nucleic acids or phosphorothioate polymer backbones and does not comprise proteins with non-covalently attached phosphorothioate nucleic acids or phosphorothioate polymer backbones. Optionally, the phosphorothioate nucleic acids or phosphorothioate polymer backbones are non-covalently attached to the non-cell penetrating proteins and the plurality does not comprise proteins with covalently attached phosphorothioate nucleic acids or phosphorothioate polymer backbones. In some embodiments, the plurality comprises one or more of the proteins comprises non-covalently attached phosphorothioate nucleic acids or phosphorothioate polymer backbones and one or more one or more of the proteins comprises covalently attached phosphorothioate nucleic acids or phosphorothioate polymer backbones. Thus, the pluarlity can comprise proteins comprising non-covalently and covalently attached phosphorothioate nucleic acids or phosphorothioate polymer backbones. Further, each conjugate can comprise a protein comprising non-covalently and/or covalently attached phosphorothioate nucleic acids or phosphorothioate polymer backbones.

Provided are cells comprising one or more of the provided cell penetrating conjugates, e.g., the cells can comprise a plurality of cell penetrating conjugates. Optionally, the conjugate is bound within the cell to an intracellular target. By way of example, the cells can include a first non-cell penetrating protein and a second non-cell penetrating protein attached to one or more phosphorothioate nucleic acids or polymer backbones. The first and second non-cell penetrating protein can be bound within the cell to an intracellular target. Optionally, the second non-cell penetrating protein binds a different epitope on the intracellular target relative to the first non-cell penetrating protein. Optionally, the second non-cell penetrating protein binds a second intracellular target. Optionally, the first and/or second non-cell penetrating protein is an antibody. Thus, the first and second non-cell penetrating proteins can be the same protein or a different protein.

Provided herein are pharmaceutical compositions comprising the cell penetrating conjugates and a pharmaceutically acceptable carrier. The provided compositions are, optionally, suitable for formulation and administration in vitro or in vivo. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

Provided compositions can include a single agent or more than one agent. In some embodiments, the compositions further include a second non-cell penetrating protein attached to one or more phosphorothioate nucleic acids or polymer backbones. Thus, provided herein are compositions comprising a first cell-penetrating conjugate comprising a first non-cell penetrating protein attached to one or more phosphorothioate nucleic acids or polymer backbones and a second cell-penetrating conjugate comprising a second non-cell penetrating protein attached to one or more phosphorothioate nucleic acids or polymer backbones. Optionally, the second non-cell penetrating protein binds an intracellular target. Optionally, the second non-cell penetrating protein binds a different epitope on the intracellular target relative to the first non-cell penetrating protein. Optionally, the second non-cell penetrating protein binds a second intracellular target. Optionally, the first and/or second non-cell penetrating protein is an antibody. The first and second non-cell penetrating proteins can be the same protein or a different protein.

The compositions for administration will commonly comprise an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

Compositions can be formulated to provide quick, sustained or delayed release after administration by employing procedures known in the art. Certain carriers may be more preferable depending upon, for instance, the route of administration and concentration of composition being administered. Suitable formulations for use in the provided compositions can be found in Remington: The Science and Practice of Pharmacy, 21st Edition, David B. Troy, ed., Lippicott Williams & Wilkins (2005).

Provided herein are kits comprising one or more of the provided conjugates and/or compositions and instructions for use. Thus, provided are kits comprising one or more cell penetrating conjugates or pharmaceutical compositions comprising the conjugates and instructions for use. Optionally, the kit further includes a second non-cell penetrating protein attached to one or more phosphorothioate nucleic acids or polymer backbones. Optionally, the second non-cell penetrating protein is in separate containers. Optionally, the kit comprises a first cell penetrating conjugate and a second cell penetrating conjugate. Optionally, the first and second cell penetrating conjugates are in separate containers. Optionally, the second non-cell penetrating protein of the second cell penetrating conjugate binds a different epitope on the intracellular target relative to the non-cell penetrating protein of the first cell penetrating conjugate. Optionally, the second non-cell penetrating protein binds a second intracellular target. Optionally, the second non-cell penetrating protein is formulated as a pharmaceutical composition comprising the second non-cell penetrating protein and a pharmaceutically acceptable carrier. Optionally, the second non-cell penetrating protein is an antibody. Optionally, the kit comprises one or more additional agents for treating or preventing one or more symptoms of a disease. Optionally, the kit comprises a means of administering the composition, such as, for example, a syringe, needle, tubing, catheter, patch, and the like. The kit may also comprise formulations and/or materials requiring sterilization and/or dilution prior to use.

Provided herein are methods of delivering a non-cell penetrating protein into a cell comprising contacting the cell with a cell penetrating conjugate. The cell penetrating conjugate including a non-cell penetrating protein attached to a phosphorothioate nucleic acid or polymer backbone. The phosphorothioate nucleic acid or polymer backbone enhances intracellular delivery of the non-cell penetrating protein. Optionally, the non-cell penetrating protein binds the nuclear protein in the cytoplasm thereby forming a non-cell penetrating protein-nuclear protein complex. Optionally, the non-cell penetrating protein-nuclear protein complex in not capable of entering the nucleus of the cell.

Optionally, the cell penetrating conjugates are used for diagnosing a disease in a subject. Thus, provided is a method of diagnosing a disease in a subject comprising administering to the subject an effective amount of a cell penetrating conjugate or composition comprising a cell penetrating conjugate as described herein. Administration of the conjugate diagnoses the disease or one or more symptoms of the disease in the subject. The disclosed methods involve comparing the levels or activity of a biomarker, e.g., intracellular target of a disease, from a test sample to a control sample. As discussed above, a control sample or value refers to a sample that serves as a reference, usually a known reference, for comparison to a test sample. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. As also discussed above, diagnosis refers to a relative probability that a disease (e.g. an autoimmune, inflammatory autoimmune, cancer, infectious, immune, or other disease) is present in the subject.

The terms comparing, correlating and associated, in reference to determination of a disease risk factor, refers to comparing the presence or amount of the risk factor (e.g., amount of intracellular target of a disease) in an individual to its presence or amount in persons known to suffer from, or known to be at risk of disease, or in persons known to be free of disease, and assigning an increased or decreased probability of having/developing the disease to an individual based on the assay result(s).

Provided herein is also a method of detecting an intracellular target in a cell, comprising contacting the cell with a cell penetrating conjugate and detecting binding of the cell penetrating conjugate to the intracellular target, wherein the cell penetrating conjugate comprises a non-cell penetrating protein attached to a phosphorothioate nucleic acid, and wherein the phosphorothioate nucleic acid enhances intracellular delivery of the non-cell penetrating protein. The cell can be a fixed cell or a live cell. Optionally, the cell is located in vitro or in vivo. Binding can be detecting directly or indirectly. It is understood and contemplated herein that numerous methods may be used to detect the binding of the cell penetrating conjugate to its intracellular target. For example, binding can be detected directly by assaying coupling between the cell penetrating conjugate and its intracellular target. Binding can be determined, for example, by selecting an assay from the group consisting of a coimmunoprecipitation assay, a colocalization assay, or a fluorescence polarizing assay, as described below. The assays are known in the art, e.g., see Sambrook et al., Molecular Cloning: A Laboratory Manual, 3$^{rd}$ Ed., Cold Spring Harbor Press, Cold Spring Harbor, N.Y. (2001); Dickson, Methods Mol. Biol. 461:735-44 (2008); Nickels, Methods 47(1):53-62 (2009); and Zinchuk et al., Acta Histochem. Cytochem. 40(4): 101-11 (2007).

Optionally, binding is determining by an imaging method or system. Thus, the provided cell penetrating conjugates can also be used in imaging applications or other applications for analyzing intracellular target levels and/or activities. For example, the provided cell penetrating conjugates can be used for in vitro or in vivo imaging of intracellular targets of interest. Optionally, the cell penetrating conjugates are used for live cell imaging. For example, live cell imaging can be used to monitor intracellular target distribution and/or dynamics inside living cells and is also applicable to monitoring target interactions. For example, the cell penetrating conjugates can be used in immunoprecipitation and co-immunoprecipitation assays to study protein-protein interactions in cells, optionally, in living cells. Optionally, the cell penetrating conjugates are used for analysis of intracellular targets by flow cytometry. In imaging applications, the cell penetrating conjugates are, optionally, labeled as appropriate to the application being used. As described above, a label or a detectable moiety is a composition detectable by spectroscopic, photochemical, biochemical, immunochemical, chemical, or other physical means. Useful labels include, but are not limited to, 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, Bioconjugate Techniques 1996, Academic Press, Inc., San Diego.

Optionally, the cell penetrating conjugate and compositions comprising the cell penetrating conjugates as described herein are useful for both prophylactic and therapeutic treatment. For prophylactic use, a therapeutically effective amount of the agents described herein are administered to a subject prior to or during early onset (e.g., upon initial signs and symptoms of an autoimmune disease). Therapeutic treatment involves administering to a subject a therapeutically effective amount of the agents described herein after diagnosis or development of disease.

Thus, provided is a method of treating a disease in a subject comprising administering to the subject an effective amount of a cell penetrating conjugate or composition comprising a cell penetrating conjugate as described herein. Administration of the conjugate treats the disease or one or more symptoms of the disease in the subject.

Optionally, the methods of treatment further include administering to the subject a second non-cell penetrating protein attached to one or more phosphorothioate nucleic acids. Optionally, the method includes administration of a first conjugate comprising a first non-cell penetrating protein attached to a phosphorothioate nucleic acid or polymer backbone and a second conjugate comprising a second non-cell penetrating protein attached to a phosphorothioate nucleic acid or polymer backbone. Optionally, the second non-cell penetrating protein binds a different epitope on the intracellular target relative to the first non-cell penetrating protein. Optionally, the second non-cell penetrating protein binds a second intracellular target. The first and second conjugates can be administered simultaneously or sequentially. Optionally, the second non-cell penetrating protein is an antibody. Optionally, the disease is selected from the group consisting of autoimmune disease, developmental disorder, inflammatory disease, metabolic disorder, cardiovascular disease, liver disease, intestinal disease, infectious disease, endocrine disease, neurological disorder, and cancer. Optionally, the disease is cancer. Optionally, the non-cell penetrating protein of the conjugate binds an intracellular target and the intracellular target is STAT3 or exportin 7. Optionally, the first non-cell penetrating protein is an antibody that specifically binds STAT3 and the second non-cell penetrating protein is an antibody that specifically binds exportin 7. Optionally, the first non-cell penetrating protein of the conjugate is an antibody that specifically binds STAT3 and the second non-cell penetrating protein is an antibody that specifically binds another epitope of STAT3.

In the provided methods of treatment, additional therapeutic agents can be used that are suitable to the disease being treated. Thus, in some embodiments, the provided methods of treatment further comprise administering a second therapeutic agent to the subject. Suitable additional therapeutic agents include, but are not limited to, therapeutic agent is selected from the group consisting of analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

According to the methods provided herein, the subject is administered an effective amount of one or more of the agents provided herein. The terms effective amount and effective dosage are used interchangeably. The term effective amount is defined as any amount necessary to produce a desired physiologic response (e.g., reduction of inflammation). Effective amounts and schedules for administering the agent may be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims.

EXAMPLE

Example 1

Inactivating Nuclear Transcription Factor STAT3 by Cell-Penetrating Antibodies

As described in more detail below, it is demonstrated herein that simultaneously targeting two discrete parts of a protein or two proteins in a complex by antibodies retains a nuclear protein in the cytoplasm. Exportin 7 was identified as an essential protein that mediates STAT3 nucleocytoplasmic shuttling. Intracellular delivery of STAT3 and exportin 7 antibodies effectively prevents STAT3 nucleocytoplasmic shuttling, trapping STAT3 in the cytoplasm. A technology was developed to allow efficient cell penetration of antibodies, in vitro and in vivo. Specifically, attachment of phosphorothioate oligonucleotides to antibodies enables efficient antibody cellular internalization and target recognition. Both local and systemic deliveries of the modified STAT3/exportin 7 antibodies effectively inhibited STAT3 activity in tumors, resulting in tumor cell apoptosis and tumor regression in various models. This technology enables antibodies to target intracellular molecules including nuclear transcription factors.

Materials and Methods

Localization of STAT3-GFP in living cells was imagined and analyzed using a LSM 510 Meta Inverted microscope (Zeiss, Jena, Germany) and bleaching experiments resulting in iFLAP imaging were performed as described (Herrmann et al., *J. Cell* Science 120:3249-3261 (2007)). Briefly, YFP and CFP emission signals of the STAT3-CFP-YFP fusion protein were equally amplified. Using λ=514 nm laser line, the YFP moiety of the fusion protein was bleached for several rounds, interrupted by image acquisition. In a post-acquisition procedure, the algorithm $I=1-I_{YFP}/I_{CFP}$ was applied to collected images resulting in the spatial distribution of STAT3-CFP-YFP as a function of time. Tumor sections were stained using protocols for indirect immunofluorescence as described previously (Herrmann et al., *Cancer Res.* 70:7455-7464 (2010)).

Delivery of antibodies against STAT3 (Santa Cruz, sc-482, Dallas, Tex.), exportin 7 (Santa Cruz, sc-98639, Dallas, Tex.), or GFP (Rockland, Gilbertsville, Pa.) in cell culture was achieved using a lipid carrier system (GenLantis, BP509604, San Diego, Calif.) according to the manufacturer's instructions. A total dose of 10 μg immunoblobulins in complex with the lipid carrier (GenLantis, BP509604, San Diego, Calif.) or oligonucleotide modified antibodies against STAT3 and exportin 7, respectively, was administered for each treatment.

Conjugation of Oligos to Antibody.

Oligonucleotides (200-300 nmol) were reduced by a 30-molar excess of TCEP (400 μL, 5 mM TEAA, pH 6.8) for 2 hours at room temperature under argon and purified by reverse phase chromatography (PRP1, linear gradient from 5 mM TEAA to 95% MeOH over 30 minutes). Removal of the thiol protecting group was confirmed by mass-spectrometry (LTQ FT, Thermo) followed by lyophilization. The reduced oligonucleotide was redissolved in 0.5 mL water/DMSO (4:1), a 25-fold excess of vinyl sulfone was added, the pH was adjusted to 8.5, reacted for 3 hours at room temperature under argon, purified by reverse phase HPLC (as above), the correct product confirmed by mass-spectrometry and the sample lyophilized. Polyclonal IgG (1.6 mg, dialyzed in PBS for 48 hours) was reduced with a 30-molar excess of TCEP in PBS for 2 hours at 37° C. under argon. After removal of the excess TCEP (Zeba spin column, Thermo; 2,000 rpm for 2 minutes), the reduced antibodies were reacted with a 20-molar excess of VS-oligonucleotide at pH 7.5 under argon overnight. Successful oligo-to-antibody-conjugation was confirmed by IEF gel electrophoresis (pH 3-9, GE Health Sciences, Pittsburgh, Pa.) comparing unconjugated to conjugated antibody.

Live Cell Imaging and Immunfluorescence.

Cells overexpressing STAT3-GFP or STAT3-CFP-YFP were grown in glass bottom cell culture dishes (MatTek, Ashland, Mass.). Localization of STAT3 in live cells under thermostat-controlled and $CO_2$ controlled conditions was analyzed using a LSM 510 Meta Inverted microscope (Zeiss, Jena, Germany). Nucleic acids were stained with Hoechst33342 (Sigma-Aldrich, St. Louis, Mo.) at 100 ng/ml. Intracellularly delivered antibodies were visualized using Zenon labeling technology (Invitrogen, Carlsbad, Calif.) according to manufacturer's instructions. The FPP assay (Lorenz et al., Nature Protoc. 1:276-9 (2006)) was adapted to visualize the nuclear retention of STAT3 and STAT3$^{K685R}$. Briefly, STAT3-GFP or STAT3$^{K685R}$-GFP expressing cells were treated with 20 µm digitonin in KHM buffer (110 mM potassium acetate, 20 mM HEPES, 2 mM MgCl$_2$) to permeabilize the outer cell membrane. Nuclear egress of STAT3-GFP or STAT3$^{K685R}$-GFP in live cells was monitored over time by confocal microscopy. Localization of STAT3-GFP or NFκB subunit p65-GFP upon leptomycin B (Sigma-Aldrich, St. Louis, Mo.) treatment was assessed by indirect immunofluorescence. Cells grown on coverslips (Fisher Scientific, Waltham, Mass.) expressing STAT3-GFP or p65-GFP were fixed with 2% paraformaldehyde (dissolved in PBS, pH 7.4) and mounted with DAPI containing Vectashield (Vector Laboratories, Burlingame, Calif.) mounting media. Microsections from tumor or normal tissue were stained using indirect immunofluorescence as described previously (Kujawski et al., J. Clin. Invest. 118: 3367-3377 (2008)). Briefly, sections were blocked with 10% goat serum and 2.5% mouse serum, rinsed with PBS and incubated with antibodies against exportin 7, nucleoporin 50, nucleoporin 153 (Santa Cruz Biotechnology, Inc., Dallas, Tex.), Ki67 (eBioscience, San Diego, Calif.), and CD31/PECAM-1 (BD Pharmingen, San Diego, Calif.) diluted 1:50 in blocking solution containing 100 ng/ml Hoechst33342 (Sigma-Aldrich, St. Louis, Mo.). Slides were rinsed in PBS (three times for 5 minutes each time), incubated with appropriate secondary fluorescent antibodies, rinsed with PBS and mounted with Mowiol (Calbiochem, San Diego, Calif.). Sections were analyzed using a LSM 510 Meta Inverted microscope (Zeiss, Jena, Germany). In vivo delivered antibodies were visualized using anti-rabbit IgG conjugated to alexa fluor 488 (Invitrogen, Carlsbad, Calif.).

Quantification of Fluorescent Emission Signals.

Figure 6A:
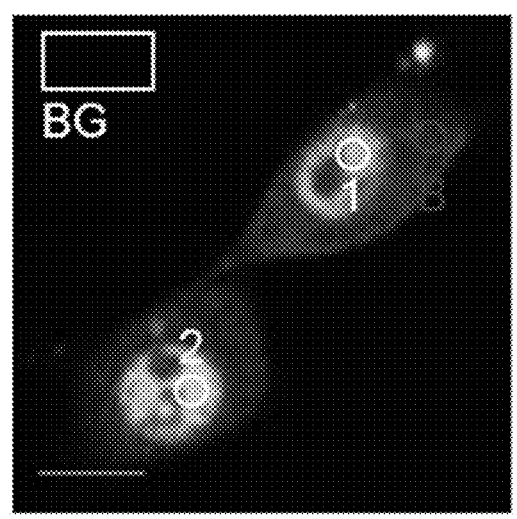
FIGS. 6A and 6B show STAT3 nucleocytoplasmic shuttling analysis by iFLAP or FLIP, respectively. Fibroblasts transformed with v-Src were used to perform intracatenar bleaching experiments (FLAP, fluorescence loss after photobleaching) to determine the compartmental turnover of STAT3. Schematic experimental design of iFLAP technique shows all regions of interest (ROIs) used to determine the spatiotemporal distribution of activated STAT3 or nuclear YFP decoy upon repeated rounds of cytoplasmic bleaching procedure in FLIP assay setting, alternatively.
Figure 6B:
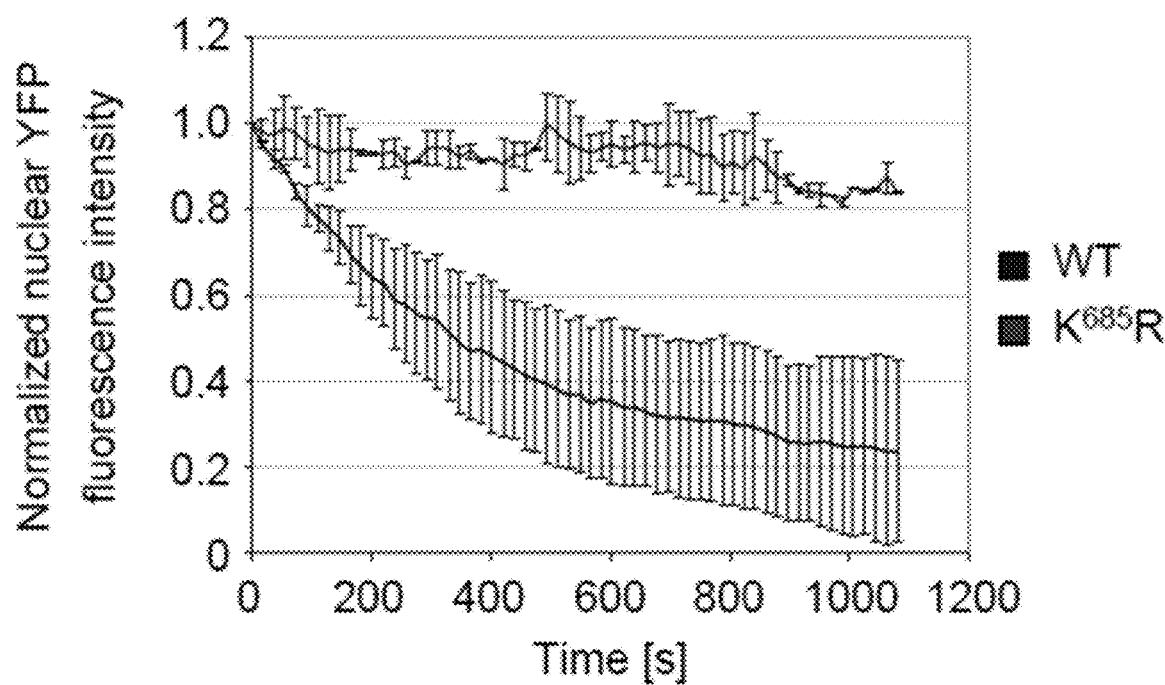
Figure 7A:
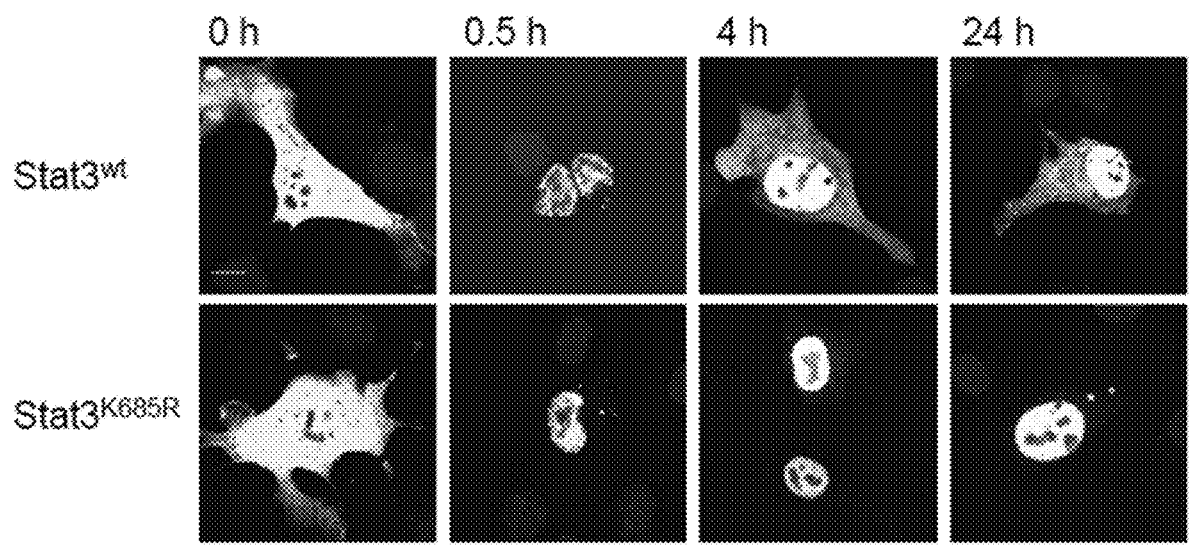
FIGS. 7A, 7B, and 7C show STAT3-K685R undergoes nuclear retention.
Figure 7B:
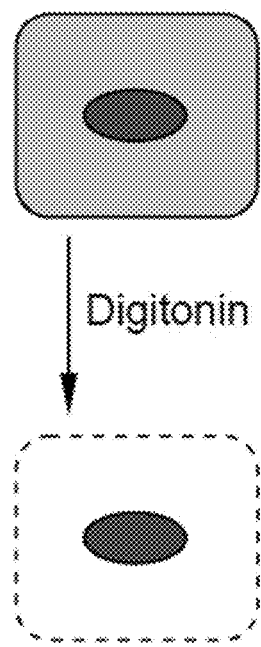
Figure 7C:
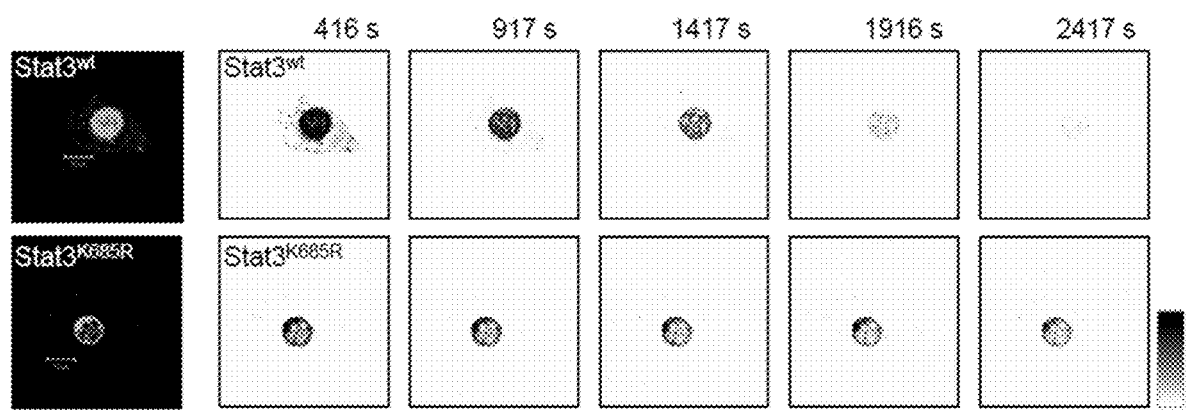

Nuclear residing proteins were quantified by the mean fluorescence intensity in the cell nucleus (Hoechst+). Complete nuclear accumulation was normalized to one (100%). Mean fluorescence intensities, tissue structures such as CD31+ blood vessel length, image masks of double-positive pixels in a field of view, or fluorescent signal densities, respectively, were quantified using Zeiss imaging software (Zeiss, Jena, Germany) or Image-Pro 6.3 (Media Cybernetics, Rockville, Md.). Nuclear decoy of STAT3-GFP or STAT3$^{K685R}$ GFP was determined by the adaption of FLIP (fluorescence loss in photobleaching) parameters as previously described (Rabut and Ellenberg, "Photobleaching Techniques to Study Mobility and Molecular Dynamics of Proteins in Live Cells. In: *Live Cell Imaging, A Laboratory Manual* Cold Spring Harbor Laboratory Press. pp. 101-126 (2004)). In contrast to FLIP, regions of interests (ROIs) have been organized as shown schematically in FIGS. 6A and 6B. In brief, acquired signals were corrected by ROI1/ROI2 after background (BG) subtraction (FIGS. 6A and 6B), and normalized using e-t/x, where t is time and x the fluorescent signal of the neighbouring control cell (ROI2). The emission intensity at the prebleach time point was normalized to one.

Intravital Multiphoton Microscopy (IVMPM).

C57BL/6 mice bearing melanoma B16 tumors were anaesthetized with isoflurane/oxygen, followed by intravenous (via retroorbital route) injection with 10 µg Annexin-V-FITC (BioVision, Milpitas, Calif.). Immediately after injection, mice were surgically opened and tumor tissue was exposed for IVMPM, performed by using an Ultima Multiphoton Microscopy System (Prairie Technologies, Middleton, Wis.). For imaging fluorescein conjugates, the excitation wavelength was set to λ=890 nm. Band-pass filters optimized for fluorescein (BP λ=525/50 nm) was used for detection. Signals of the extracellular matrix are given by second harmonic generation at excitation wavelength λ=890 nm and was detected with BP λ=460/50 nm.

In Situ Localization of Protein Interaction.

Human U251 brain tumor cells were grown in a glass chamber slide system (Fisher Scientific, Waltham, Mass.) and Duolink® procedure was performed according to the manufacturer's instructions (OLINK Bioscience, Uppsala, Sweden). Detecting antibodies used were purchased from Santa Cruz (STAT3, catalogue no. sc-482) and Acris (exportin 7, catalogue no. AP16201PU-N). A STAT3 blocking peptide purchased from Santa Cruz (Dallas, Tex.) was used at 0.01 mg/ml.

Oligo-Pulldown Assay.

To determine STAT3 DNA-binding activity, oligo-pulldown assay was performed using nuclear extracts isolated from U87 tumors grown in athymic nu/nu mice. After homogenizing tumor tissues, nuclear extracts were isolated, using a combination of (i) hypotonic buffer A containing 10 mM HEPES-KOH (pH 7.9), 1.5 mM MgCl$_2$, 10 mM KCl and (ii) high-salt buffer C containing 20 mM HEPES-KOH (pH 7.9), 420 mM NaCl, 1.5 mM MgCl$_2$, 0.2 mM EDTA, 25% glycerol. Protease inhibitors 0.2 mM PMSF, 0.5 mM DTT, 1 mM Na$_3$VO$_4$ were added fresh. A biotinylated oligo, 5'-AGCTTCATTTCCCGTAAATCCCTAAGCT-3' (SEQ ID NO:1) (the sis-inducible element SIE with STAT3 binding site in bold), was incubated with 400 µg nuclear extract in binding buffer (12 mM HEPES pH 7.9, 12% glycerol, 4 mM Tris pH 7.9, 150 mM KCl, 1 mM EDTA; fresh: 1 mM DTT, 0.1 µg/µl poly(dI:dC), 0.5 µg/µl BSA) for two hours at room temperature. Strepavidin magnetic beads (Thermo Scientific, Waltham, Mass.) used at 50 µl per sample were prewashed thrice with 1 ml binding buffer, collected in a magnetic stand, and supernatant was removed. Strepavidin magnetic beads were blocked for 30 min at room temperature in 50 µl blocking buffer containing 100 µg BSA, 10 µg poly(dI:dC), 10 µg ssDNA (salmon sperm DNA at [10 µg/µl] used), followed by incubating with sample for two hours at room temperature. Precipitates were collected in a magnetic stand, washed three times using binding buffer, and resuspended in 40 µl 4× reducing protein sample buffer (Laemmli). Protein-precipitates were electrophoretically separated by SDS-PAGE. Supernatant after initial clearance was collected and nuclear proteins were electrophoretically separated to assess a loading control of protein input.

Conjugation of Oligos to Antibody.

The following DNA oligonucleotide sequences have been synthesized for attachment to antibodies:
Oligonucleotide sequences used for conjugation to antibodies:

phospothioated
(SEQ ID NO: 2)
/5ThioMC6-D//iSpC3//iSpC3//iFAM//iSpC3//iSpC3/
T*C*C*A*T*G*A*G*C*T*T*C*C*T*G*A*T*G*C*T non-phospothioated
(SEQ ID NO: 3)
/5ThioMC6-D//iSpC3//iSpC3//iFAM//iSpC3//iSpC3/
TCCATGAGCTTCCTGATGCT phospothioated random 1
(SEQ ID NO: 4)
/5ThioMC6-D//iSpC3//iSpC3//iFAM//iSpC3//iSpC3/
C*T*G*T*A*G*T*C*C*T*C*T*G*A*G*T*A*C*C*T phospothioated random 2
(SEQ ID NO: 5)
/5ThioMC6-D//iSpC3//iSpC3//iFAM//iSpC3//iSpC3/
C*C*C*A*G*G*A*G*T*C*T*C*C*T*G*A*T*T*T*T T, thymine; A, adenine; G, guanine; C, cytosine; (*) indicates phosphorothioation. 5ThioMC6-D, 1-O-Dimethoxytrityl-hexyl-disulfide, 1'-[(2-cyanoethyl)-(N,N-diisopropyl)]-phosphoramidite (Thiol-Modifier C6 S—S); iSpC3, C3 3-(4,4'-Dimethoxytrityloxy)-propyl-1-[(2-cyanoethyl)-(N,N-diisopropyl)]-phosphoramidite (Spacer Phosphoramidite); iFAM, 2-Dimethoxytrityloxymethyl-6-(3', 6'-dipiv-aloylfluorescein-6-yl-carboxamido)-hexyl-1-O-[(2-cyanoethyl)-(N,N-diisopropyl)]-phosphoramidite (6-Fluorescein Phosphor-amidite) (Glen Research, Sterling, Va.).

Immunoblotting and Immunoprecipitation.

Whole cell lysates or tumor tissue homogenates were prepared using RIPA lysis buffer containing 50 mM Tris (pH 7.4), 150 mM NaCl, 1 mM EDTA, 0.5% NP-40, 1 mM NaF, 15% glycerol, and 20 mM β-glycerolphosphate. A protease inhibitor cocktail was added fresh to the lysis buffer (Mini Protease Inhibitor Cocktail, catalogue no. 04693124001, Roche, Basel, Switzerland). Resveratrol (Cayman Chemical, Ann Arbor, Mich.) was used in vitro at a suboptimal concentration of 10 μM for indicated times. Normalized protein amounts were subjected to electrophoretic separation by SDS-PAGE, transferred onto nitrocellulose for Western blotting, and subsequent immunodetection was performed using antibodies against exportins 1, 2, 5, 7, STAT3, VEGF, nucleoporin 50 (Santa Cruz, Dallas, Tex.), phosphorylated STAT3 (Tyr705), acetylated STAT3 (Lys685), cleaved PARP1, cleaved caspase 3, Bcl-2, cyclin D1 (Cell Signaling Technology, Boston, Mass.), angiopoietin 1, exportin T (Millipore, Billerica, Mass.), exportin 4 (Epitomics/Abcam, Burlingame, Calif.), exportin 6 (Proteintech Group, Chicago, Ill.), and β-actin (Sigma-Aldrich, St. Louis, Mo.). For immunoprecipitation, whole cell lysates of human U251 brain tumor cells or whole tumor homogenates at a total concentration of 1 mg per sample were cleared using indicated antibodies coupled to protein G agarose beads (Invitrogen, Carlsbad, Calif.). Non-targeting rabbit immunoglobulins (Abcam, Burlingame, Calif.) were included as controls. Normalized protein amounts were incubated for 16 hours shaking at 4° C. with antibody coupled to beads, washed three times at 4° C. using ice cold PBS and subjected to SDS-PAGE.

Mice and Cell Culture.

All animals were maintained in a pathogen-free room at City of Hope Research Animal Facilities. The animal use procedures were approved by institutional committee of Beckman Research Institute at City of Hope Medical Center. For subcutaneous tumor challenge, athymic nu/nu mice (NCI, Frederick, Md.) were injected with 5×10⁶ MEF cells stably expressing STAT3 or STAT3$^{K685R}$, or 10⁶ U87 human brain tumor cells into the flank. In a syngeneic model, C57BL/6 mice (The Jackson Laboratory, Bar Harbor, Me.) were injected s.c. with 10⁵ B16 melanoma cells. After tumors reached 5-7 mm in diameter, antibody treatment was administered every other day. Fibroblast 3T3/v-Src cells, MEF cells, and human U87 brain tumor cells were maintained in DMEM containing 10% heat inactivated FBS (Sigma-Aldrich, St. Louis, Mo.). Mouse melanoma B16 cells were grown in RPMI 1640 medium supplemented with 10% FBS. To establish cell lines stably expressing STAT3 constructs, STAT3 deficient MEF cells were transfected with STAT3-YFP or STAT3K685-YFP, following the Flp-In protocol (Invitrogen, Carlsbad, Calif.). Reconstituted MEF cells were subsequently sorted by flow cytometry for YFP+ to improve purity >95%.

Results and Discussion

The figures and results of the described methods are discussed in more detail below. Briefly, FIGS. 1-3 illustrate cell-penetrating antibodies can bind a nuclear transcription factor such as STAT3. FIGS. 5-12 further illustrate how using two cell-penetrating antibodies against a nuclear protein (e.g. STAT3) and a protein interacting with the nuclear protein (e.g., exportin 7) can block the activity of the nuclear protein (e.g., STAT3). FIGS. 13-18 show phosphorothioation, but not nucleic acid sequence, is important for enabling cell penetration of phosphorothioate nucleic acid modified antibodies, allowing target recognition and inactivation of target protein function in vivo and in vitro.

Although activated STAT3 is largely confined in the nucleus, STAT3 shuttles to the cytoplasm to be reactivated. According to diffusion properties of spherical particles, an increase in molecular weight can unbalance compartmental accumulation of proteins. It was thus postulated that using two antibodies to recognize two discrete parts of a nuclear protein or an additional interacting protein could form a large stable complex, thereby tipping the balance in favor of cytoplasmic compartmental accumulation of the nuclear protein(s). To test this hypothesis, first antibodies were delivered, using a lipid carrier, against STAT3 and GFP proteins to STAT3-GFP expressing 3T3 cells transformed by v-Src that persistently activates STAT3. When the two antibodies were delivered into the cells facilitated by the lipid carrier, STAT3-GFP fusion protein was found mainly trapped in the cytoplasm (FIG. 1A).

Figure 1B:
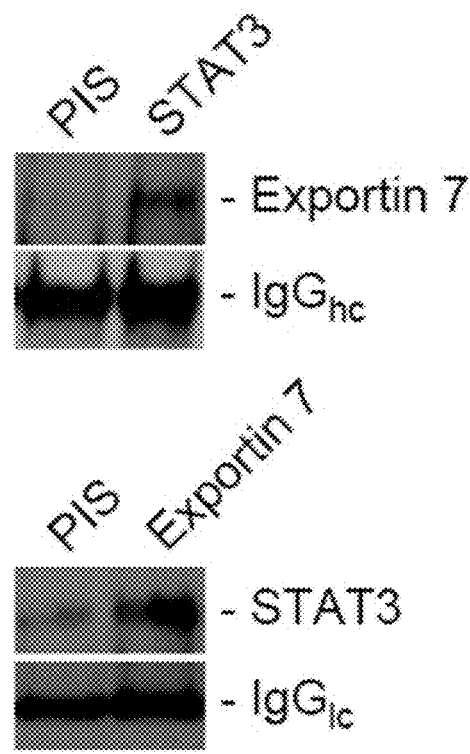
Figure 1C:
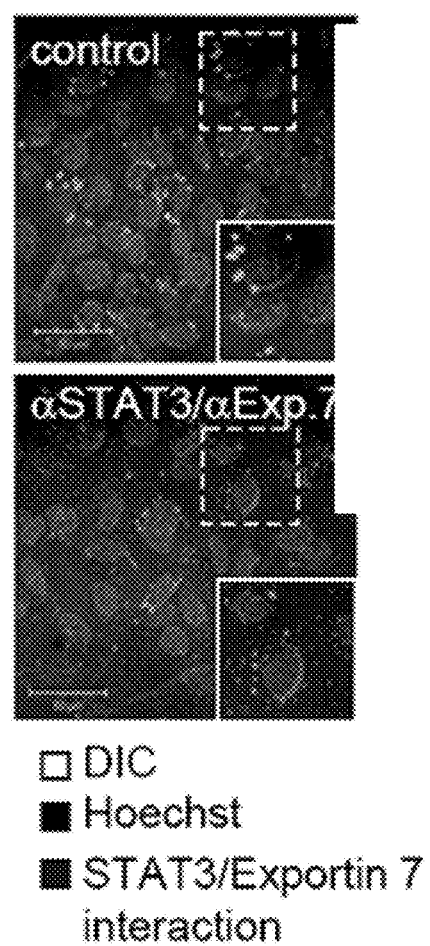
Figure 1D:
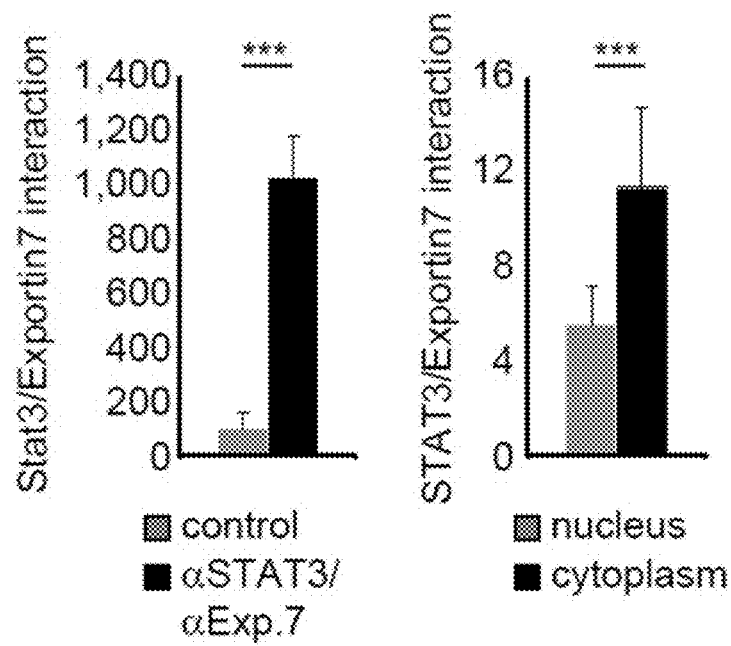
Figure 1E:
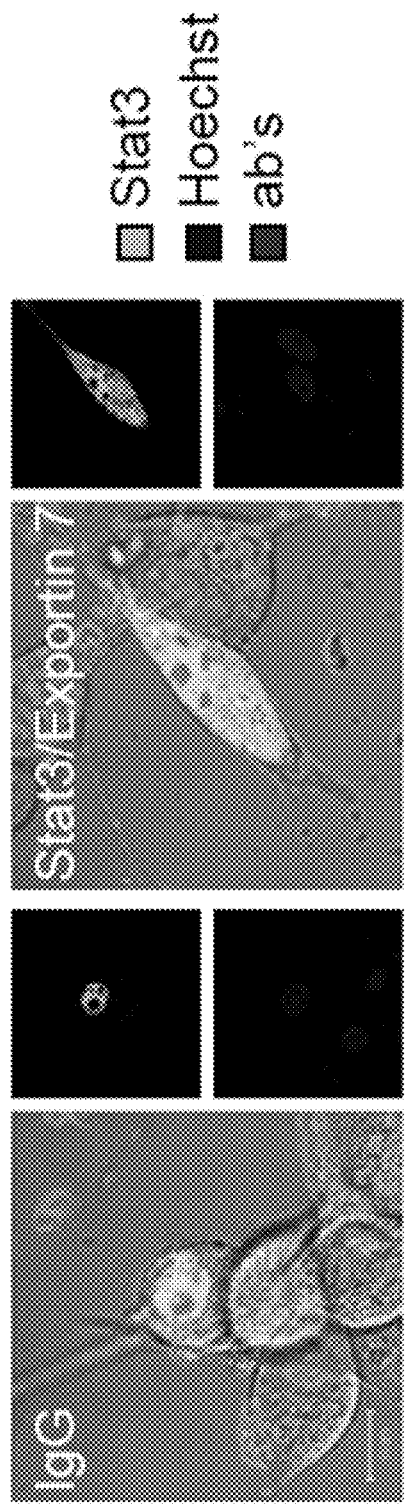
Figure 5A:
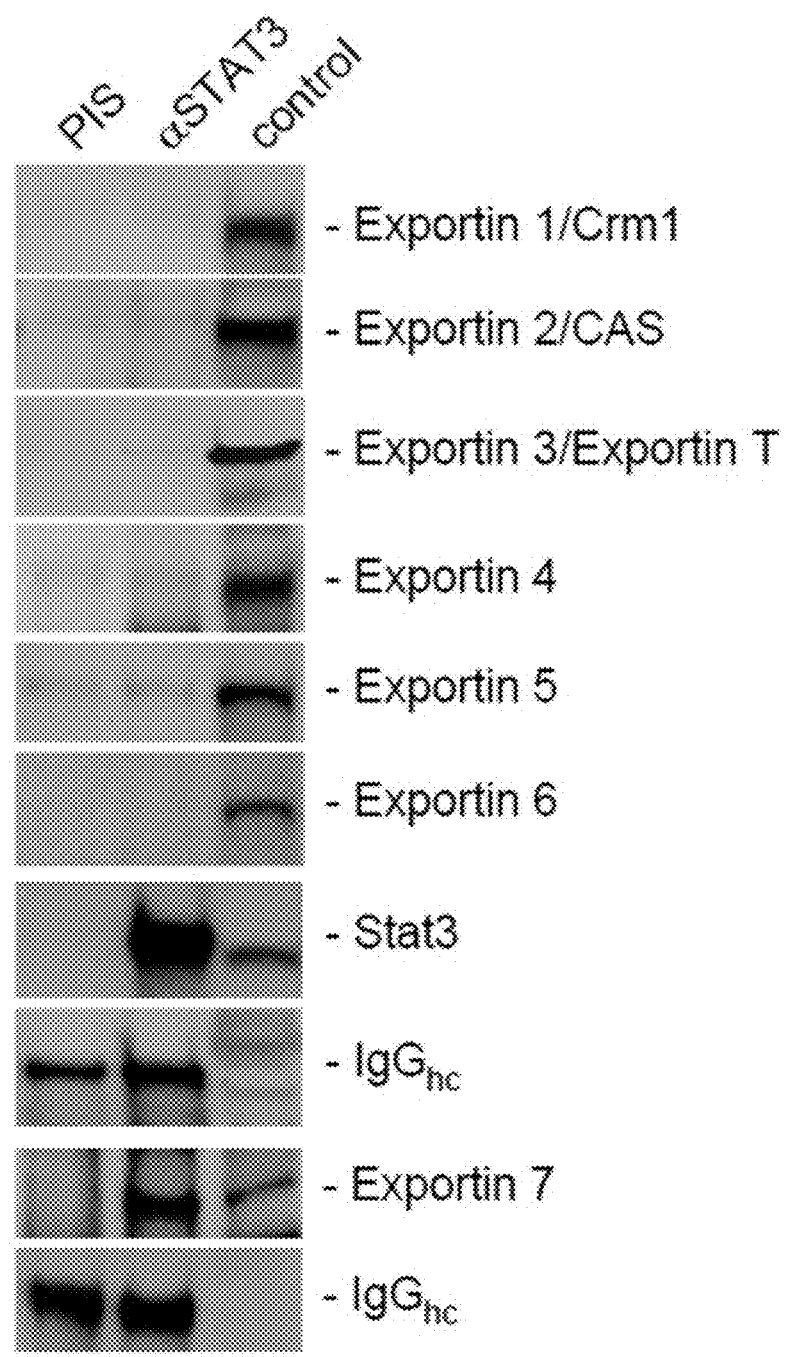
FIGS. 5A and 5B show STAT3 interacts with Exportin 7.
Figure 5B:
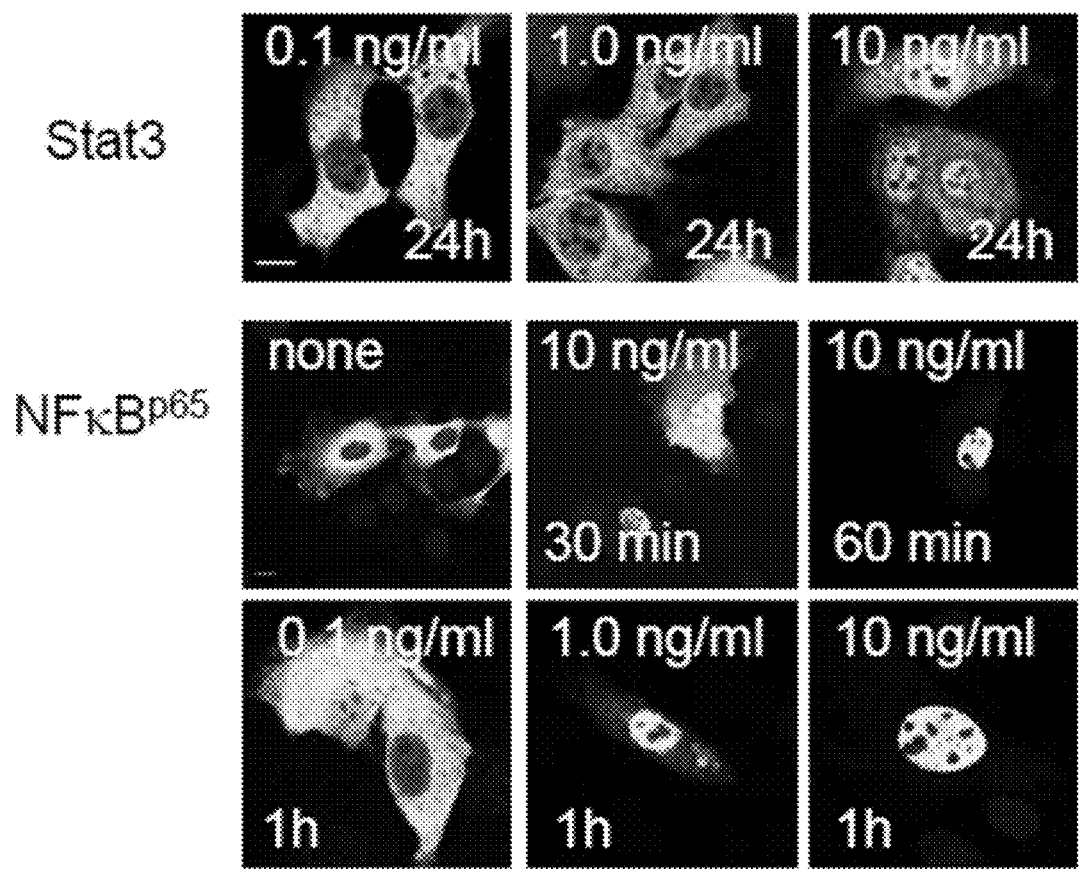

To extend this approach for targeting STAT3 physiologically, an endogenous protein that interacts with STAT3 in the cytoplasm was identified, thereby allowing trapping of STAT3 in the cytoplasm based on the same principle shown by the STAT3/GFP two-antibody treatment. It was purported that exportin(s) that shuttles STAT3 into the cytoplasm might form a relatively stable complex with STAT3. It was therefore attempted to identify the key exportin(s) involved in STAT3 shuttling into the cytoplasm. The involvement of exportin 1 in nucleocytoplasmic shuttling of STAT1 and to some extent, also STAT3 has been shown (Bhattacharya and Schindler, *J. Clin. Invest.* 111:553-9 (2003); Reich and Liu, Nature Rev. Immunol. 6:602-12 (2006); McBride et al., Embo J. 21:1754-63 (2002)). Immunoprecitation with STAT3 antibody followed by Western blot analysis with antibodies against various exportins indicated that exportin 7 was associated with STAT3 (FIG. 1B and FIG. 5A). The specific involvement of exportin 7 with STAT3 was further confirmed (FIG. 5B). Exportin 1 had also some detectable activity for STAT3 shuttling into cytoplasm as shown by a prolonged treatment with a Crm1-specific inhibitor at high concentrations (FIG. 5B). Interaction between STAT3 and export 7 in the cytoplasm was further demonstrated by the Duolink® (Olink Technologies, Uppsala, Sweden) technique (FIGS. 1C and 1D). Substituting GFP antibody with an exportin 7 antibody showed that cytoplasmic accumulation of STAT3-GFP was achieved (FIG. 1E).

Figure 2A:
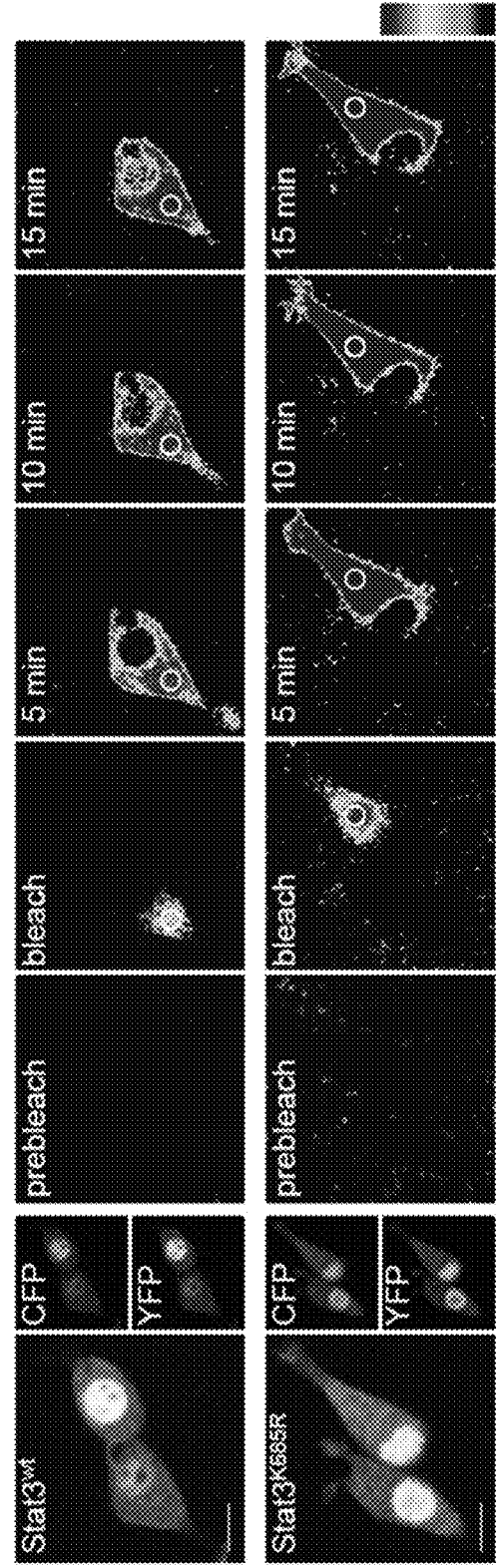
FIGS. 2A, 2B, 2C, 2D, 2E, 2F, and 2G show lysine acetylation of STAT3 determines STAT3 nucleocytoplasmic shuttling and subcellular localization of Exportin 7.
Figure 2B:
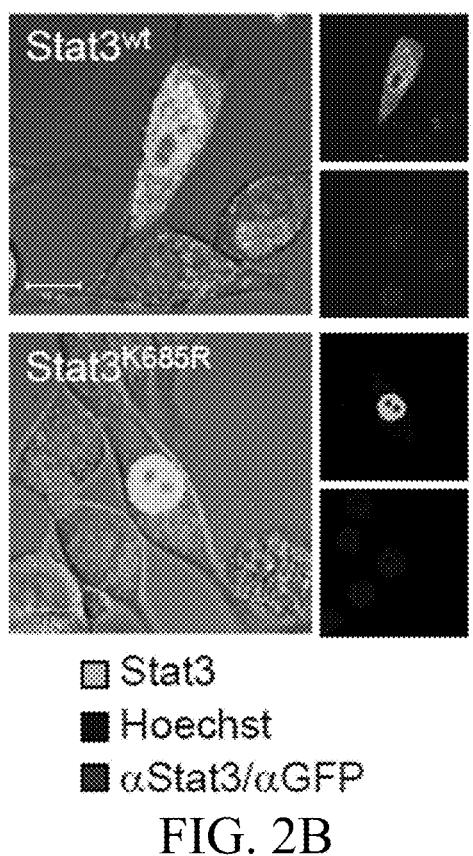
Figure 2C:
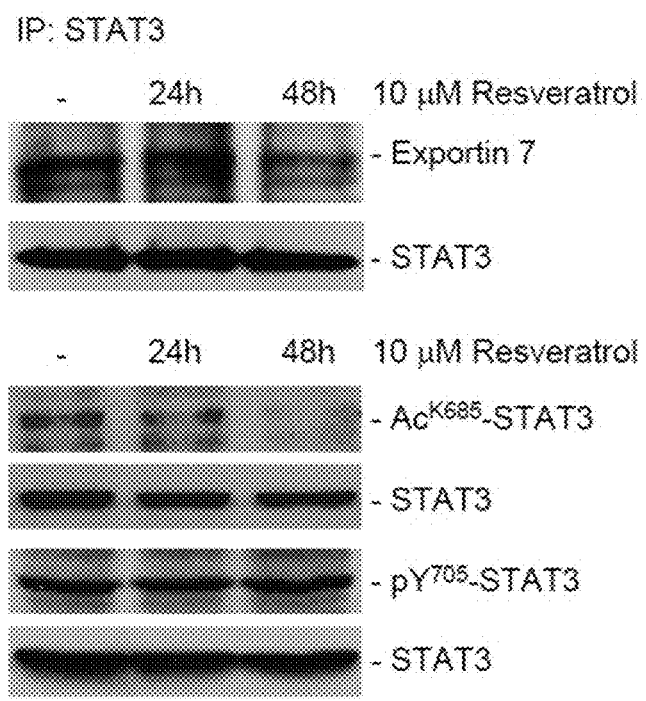
Figure 2D:
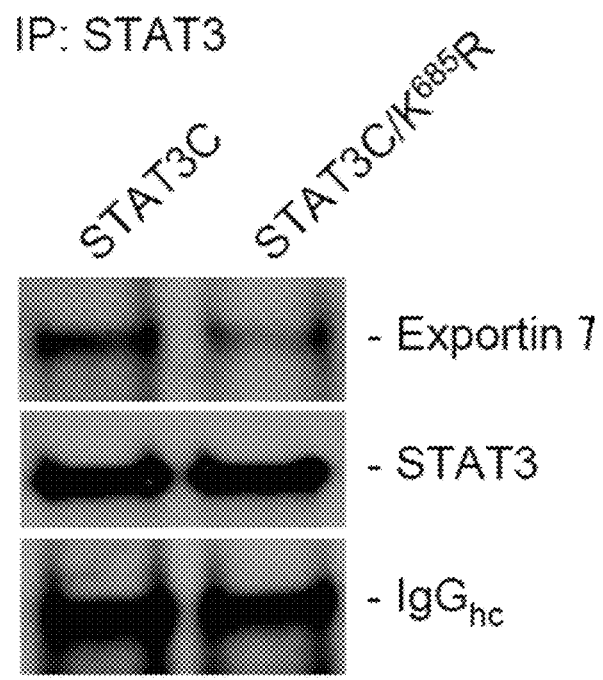

Because exportin 7 has been shown to recognize lysine containing motifs of cargo proteins in order to distinguish substrates, it was examined whether acetylation of STAT3 at lysine 685 is crucial for STAT3 cytoplasmic shuttling. The nucleocytoplasmic shuttling of STAT3 wt and STAT3$^{K685R}$ was assessed by iFLAP live cell confocal microscopy. Results from these analyses showed that STAT3$^{K685R}$ shuttling was considerably reduced due to nuclear retention (FIGS. 2A, 2B, 6A, 6B, 7A, 7B, and 7C). By either mutating STAT3 at lysine K685 or treating cells with resveratrol, which can inhibit STAT3 acetylation, a requirement of acetylation for STAT3/exportin 7 interaction was demonstrated (FIGS. 2C and 2D).

Figure 2E:
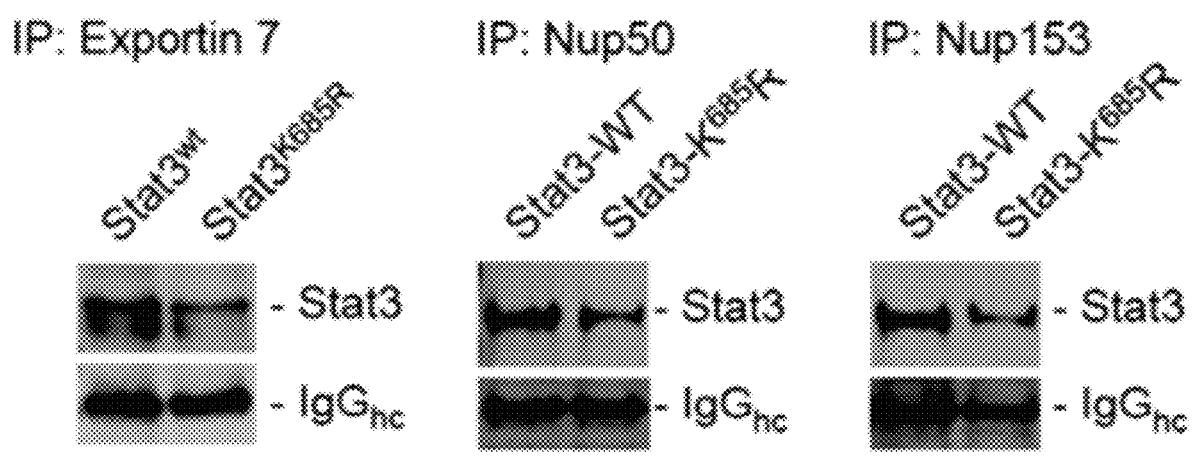
Figure 2F:
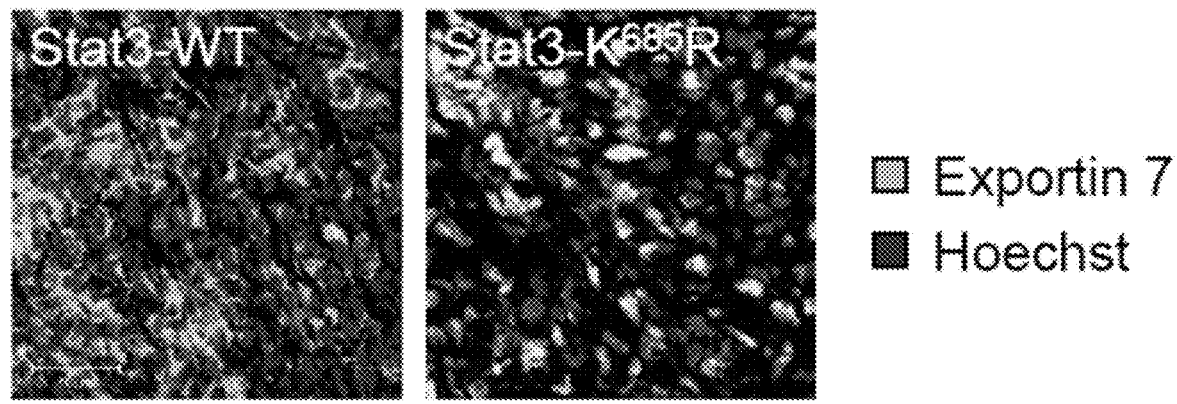
Figure 2G:
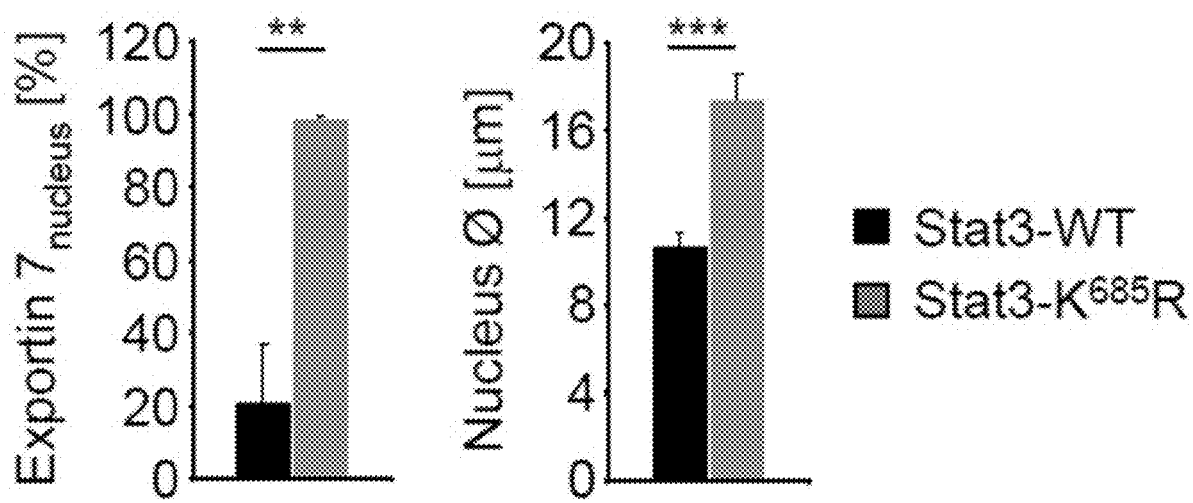
Figure 8A:
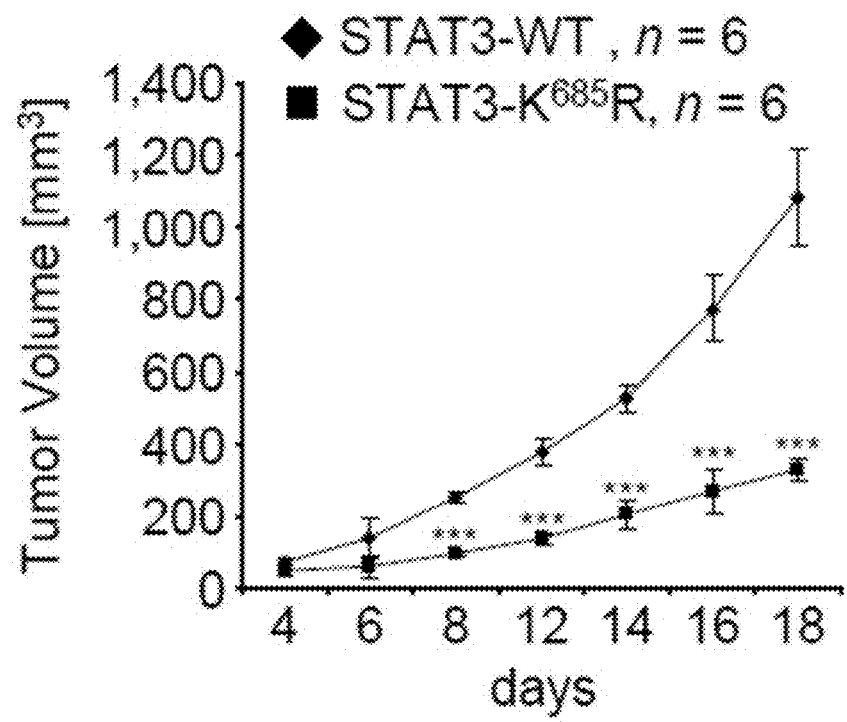
FIGS. 8A, 8B, 8C, and 8D show mutating STAT3 at lysine K685 abrogated its interaction with the inner nuclear pore complex (NPC) in vivo. STAT3 deficient MEF cells were stably reconstituted with STAT3 wt or STAT3K685R, respectively.
Figure 8B:
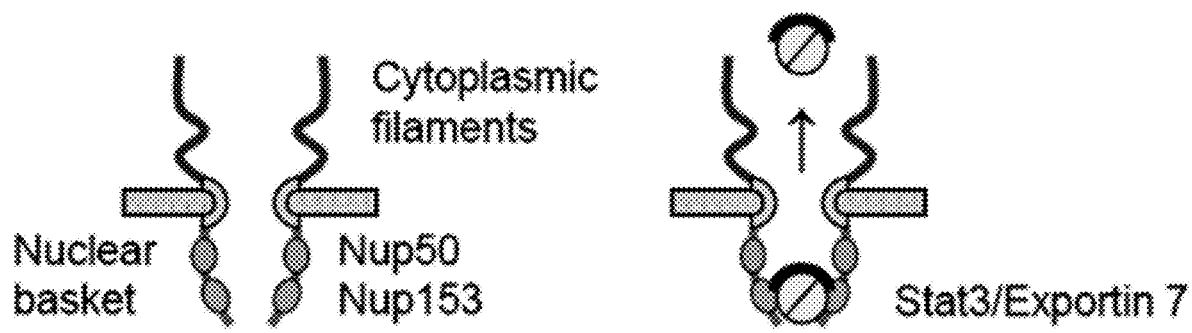
Figure 8C:
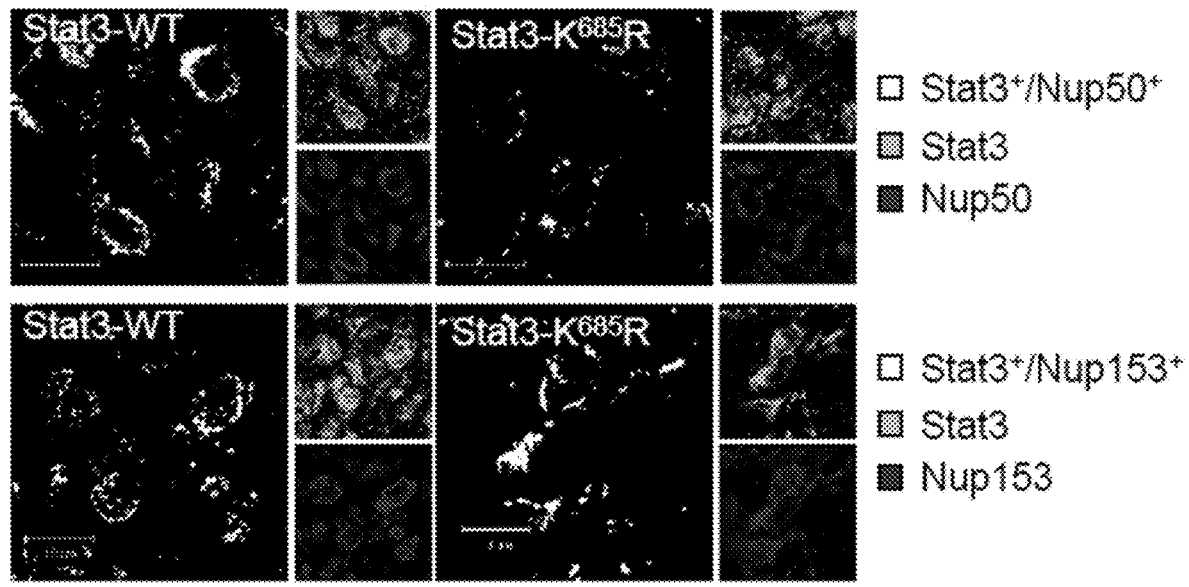
Figure 8D:
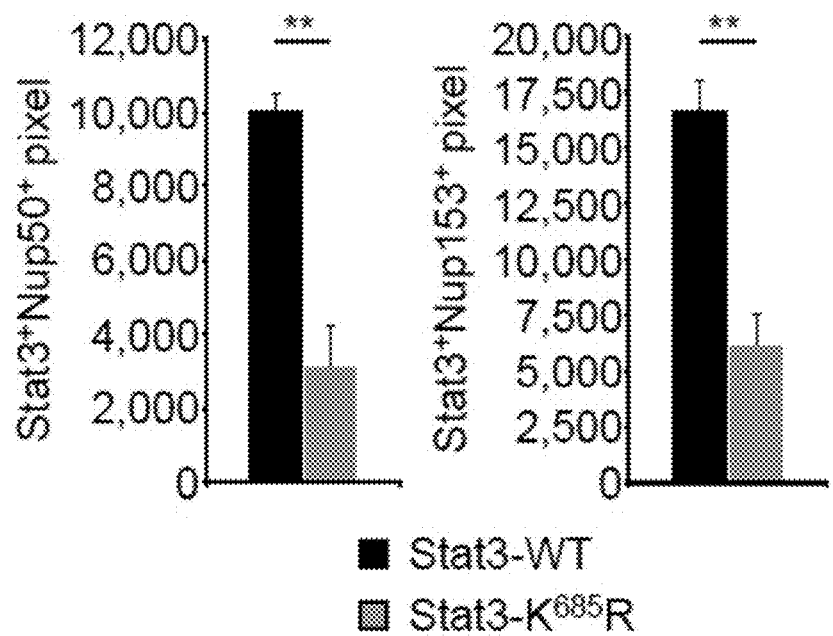
Figure 9:
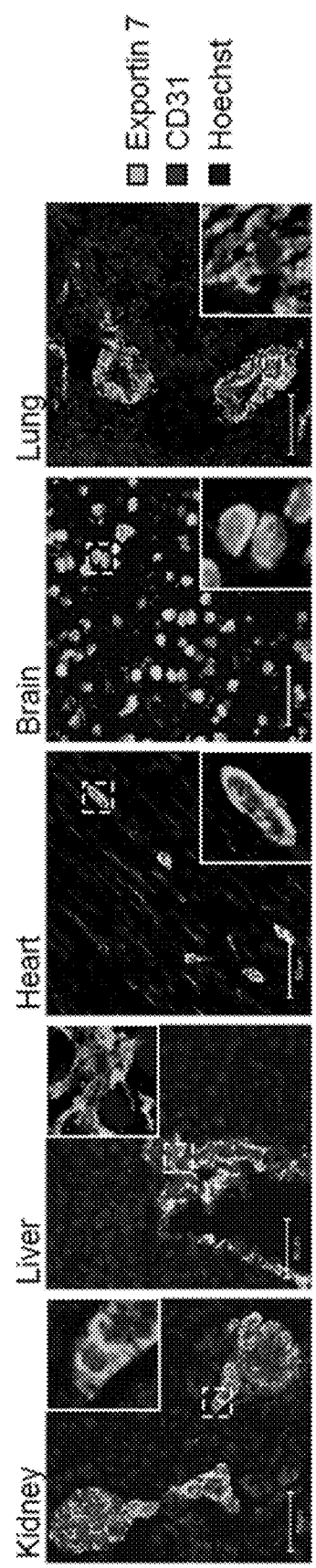
FIG. 9 are images showing Exportin 7 localization is confined to the cytoplasm in normal tissues. Confocal microscopic images of microsections from the indicated tissues were stained for exportin 7, CD31, and nucleic acids by indirect immunofluorescence. Higher magnification of exportin 7+ areas (dashed line) are shown in upper right or lower right corner, respectively. Scale bar 50 μm.
Figure 10A:
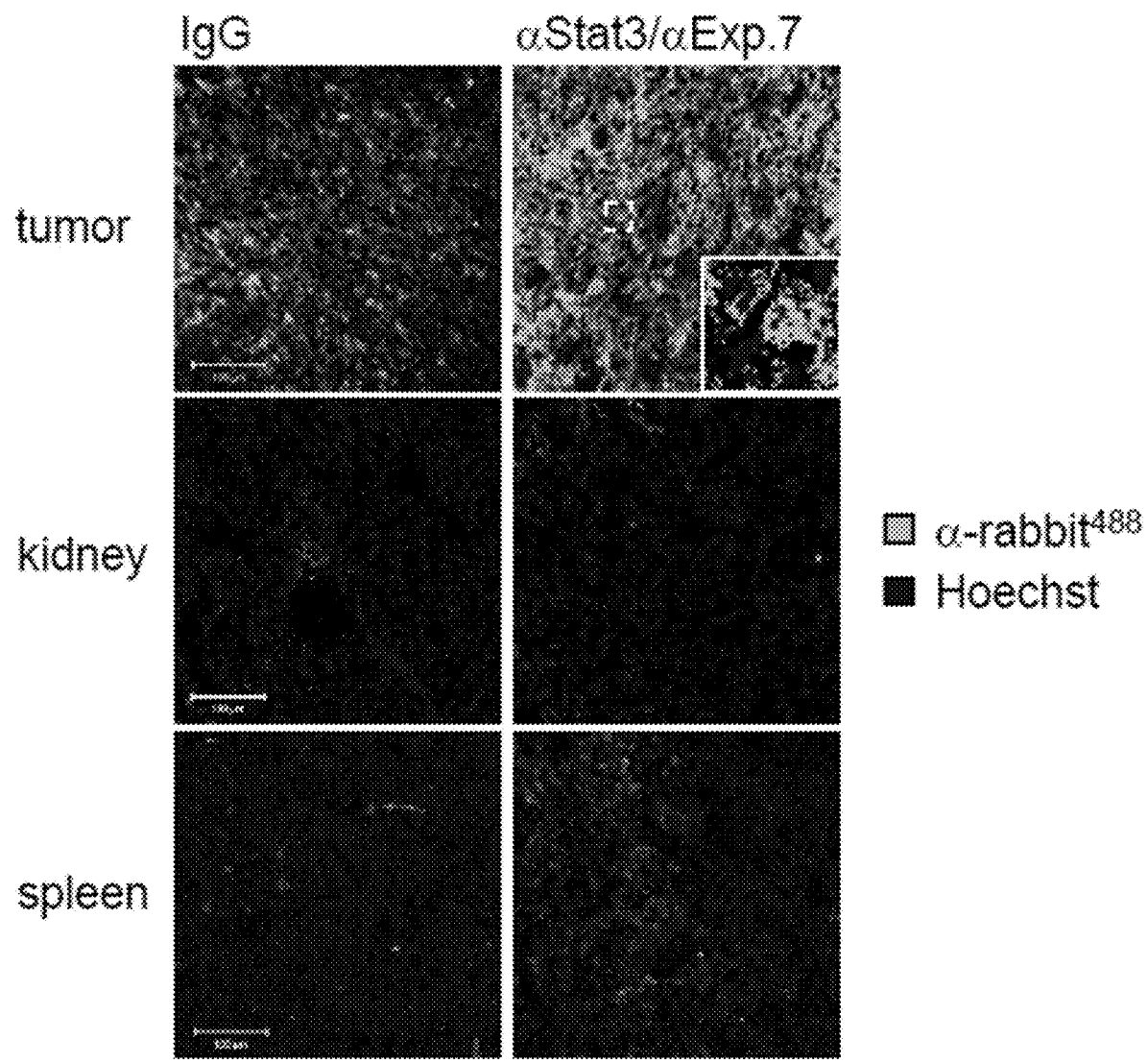
FIGS. 10A, 10B, and 10C show targeting STAT3 and exporting 7 complexes by duo-antibodies blocks STAT3 shuttling and functions in vivo.
Figure 10B:
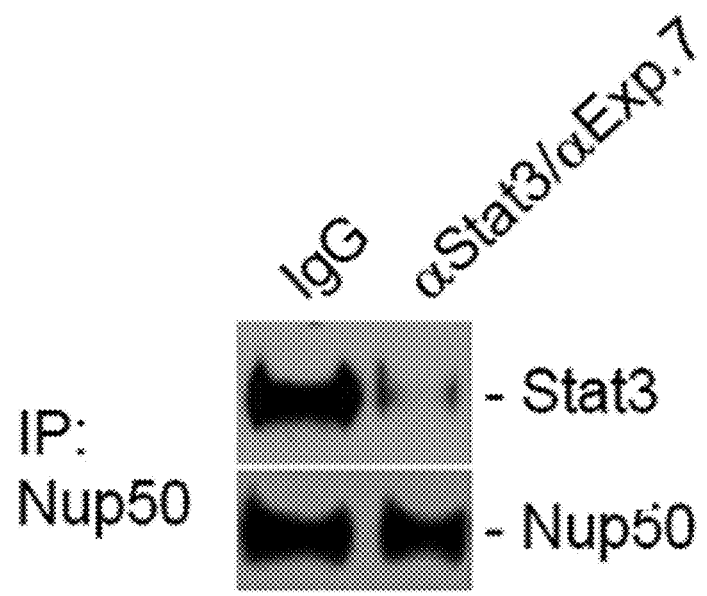
Figure 10C:
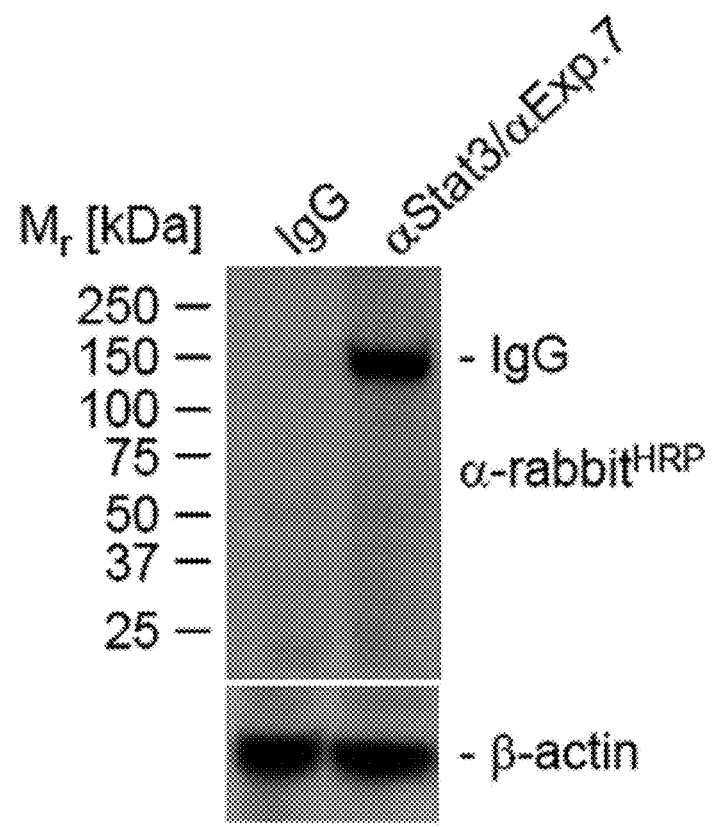

The impact of blocking exportin 7-mediated nuclear egress of STAT3 into the cytoplasm in vivo was further examined using mouse Stat3-null embryonic fibroblasts (MEFs) overexpressing either STAT3 wt or STAT3$^{K685R}$. Tumor growth kinetics indicates substantially decreased tumorigenic potential of STAT3$^{K685R}$-expressing MEFs (FIG. 8A). A concomitant reduction in the interaction between exportin 7 and STAT3$^{K685R}$ was detected (FIG. 2E). Furthermore, exportin 7-mediated interactions between STAT3$^{K685R}$ and nucleoporins, specifically nucleoplasmic FG-rich repeat Nup50 and Nup153 of the NPC, which are thought to facilitate the movement of proteins from the nucleus to the cytoplasm, were considerably decreased (FIGS. 2E, 8C and 8D). Further supporting an important role of acetylated STAT3 in nuclear egress, STAT3$^{K685R}$-expressing MEFs exhibit an accumulation of exportin 7 in the nucleus, which is associated with a substantial increase of the nuclear diameter (FIGS. 2F and 2G), indicating an effective inhibition of protein nuclear export. This is in sharp contrast to cells in normal organs/tissues, in which exportin 7 is found predominantly in the cytoplasm (FIG. 9).

Figure 3A:
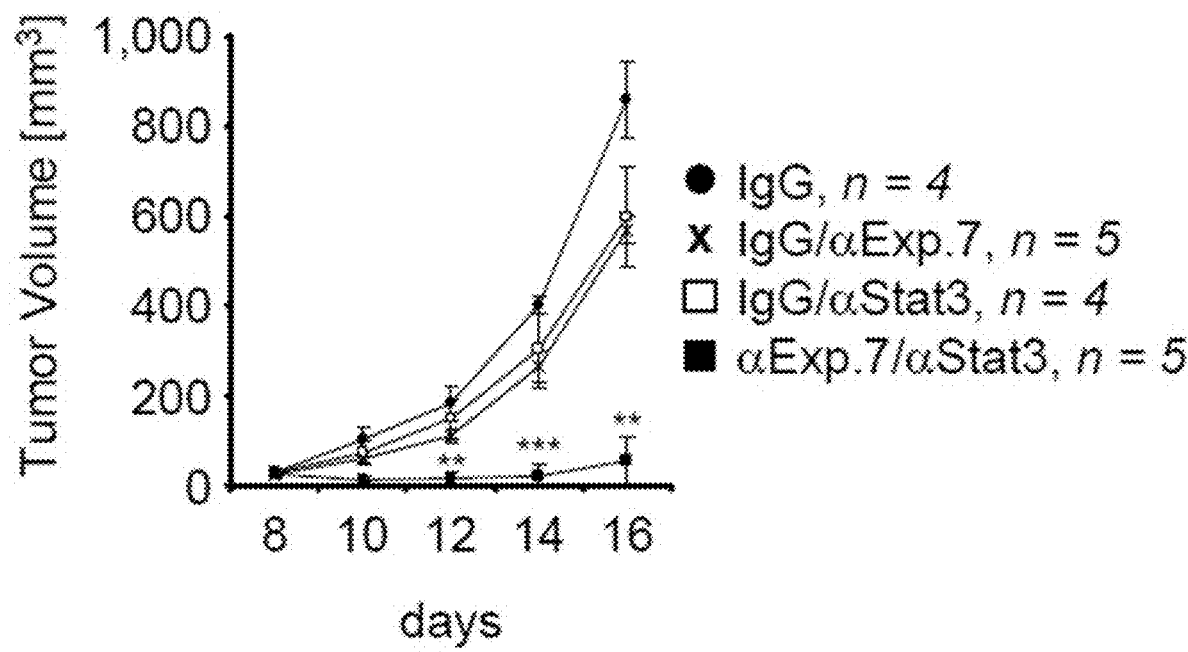
FIGS. 3A, 3B, 3C, 3D, 3E, 3F, 3G, 3H, and 3I show targeting the STAT3 and exportin 7 complex in vivo is effective for cancer therapy.
Figure 3B:
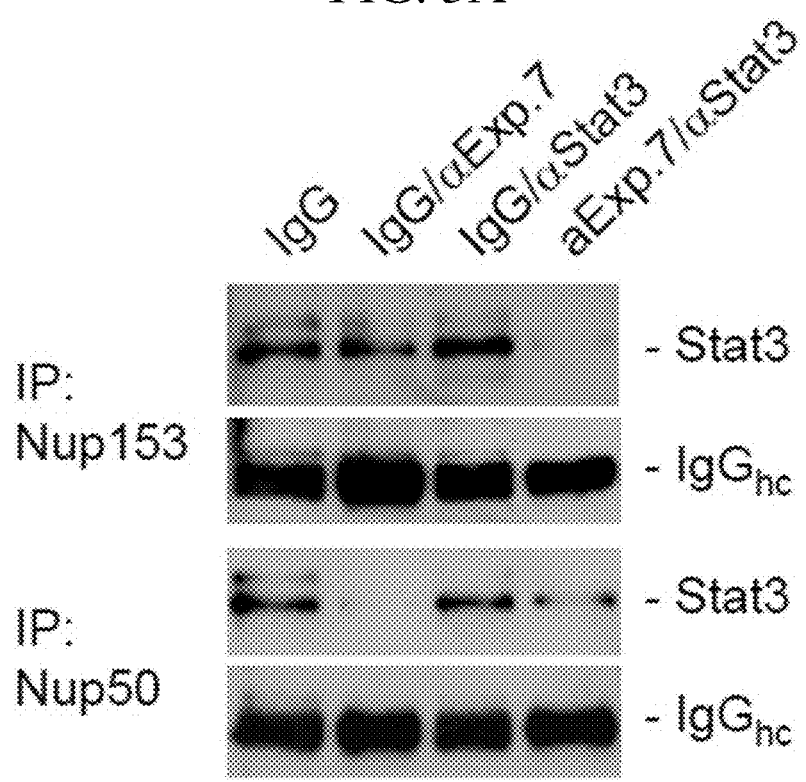
Figure 3C:
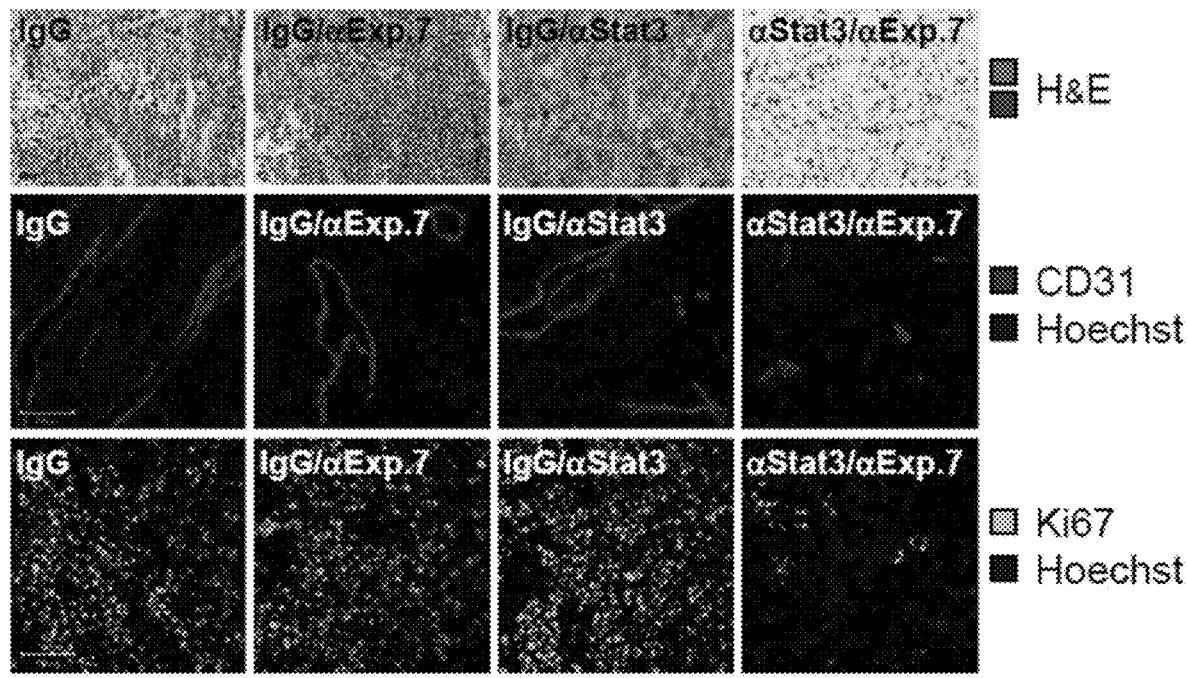
Figure 3D:
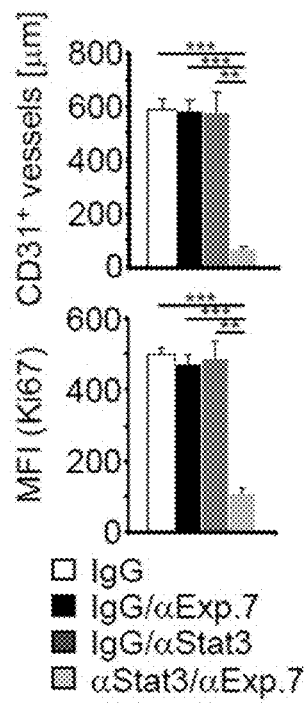
Figure 3E:
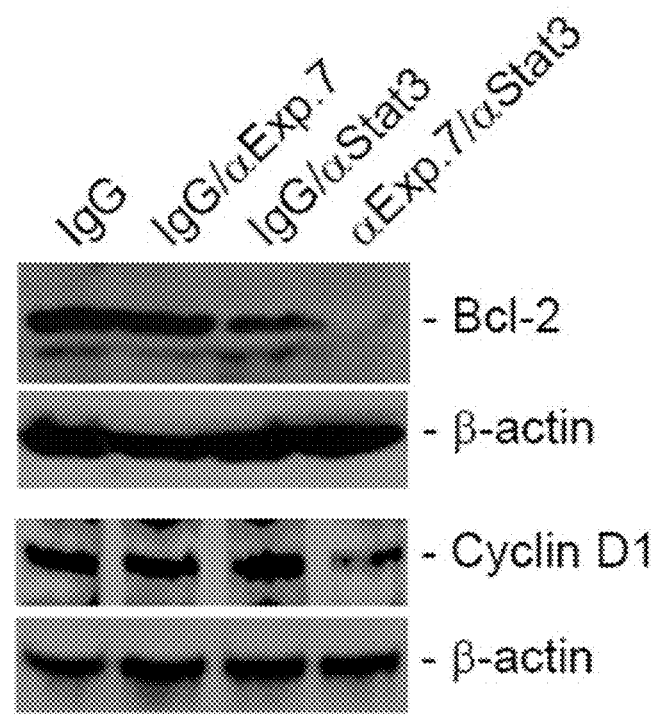
Figure 3F:
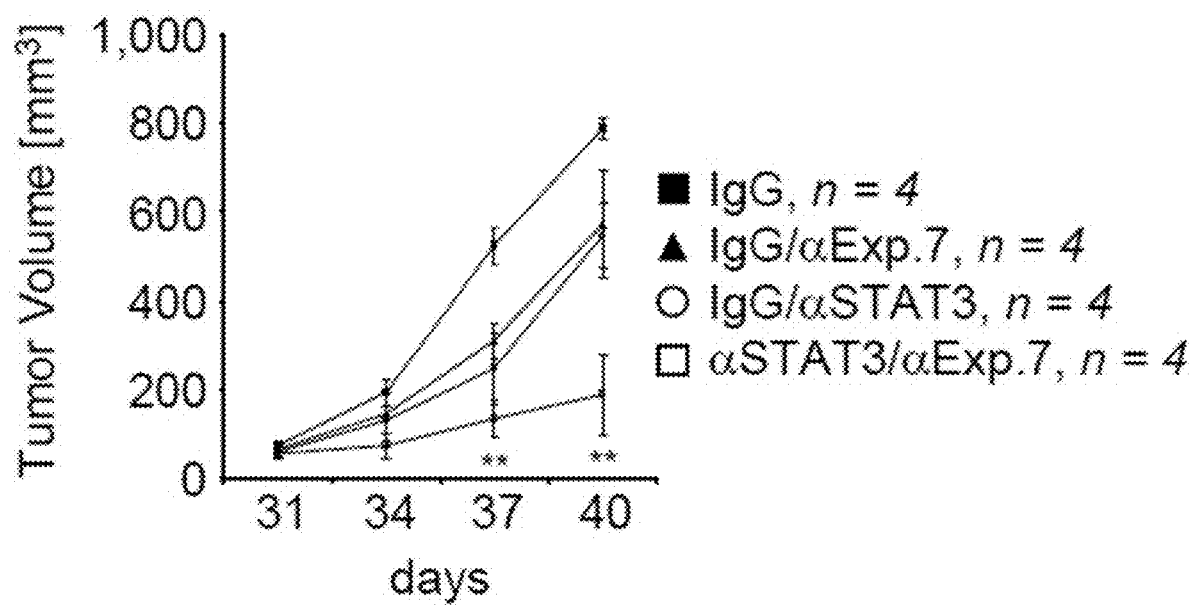
Figure 3G:
Figure 3H:
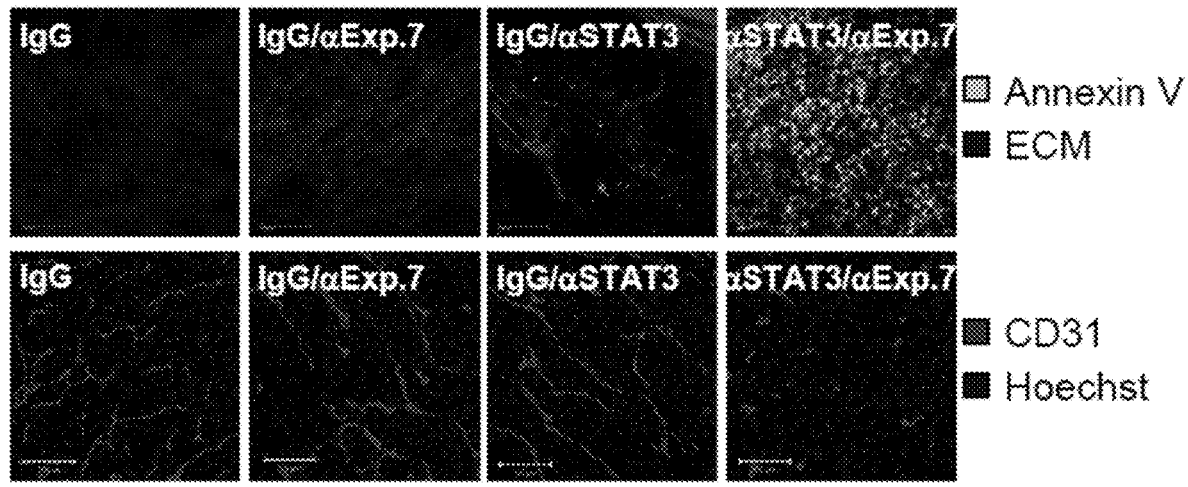
Figure 3I:
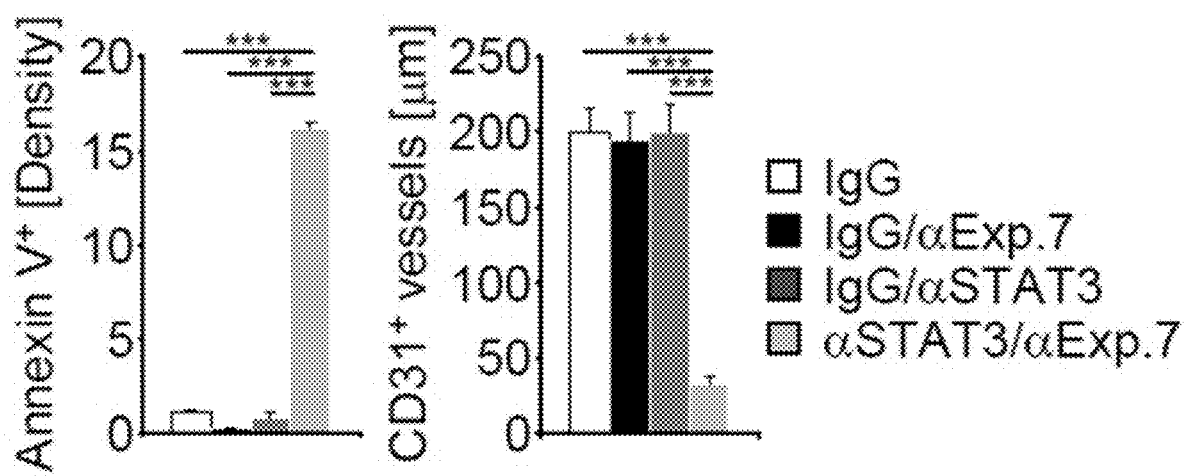
Figure 11A:
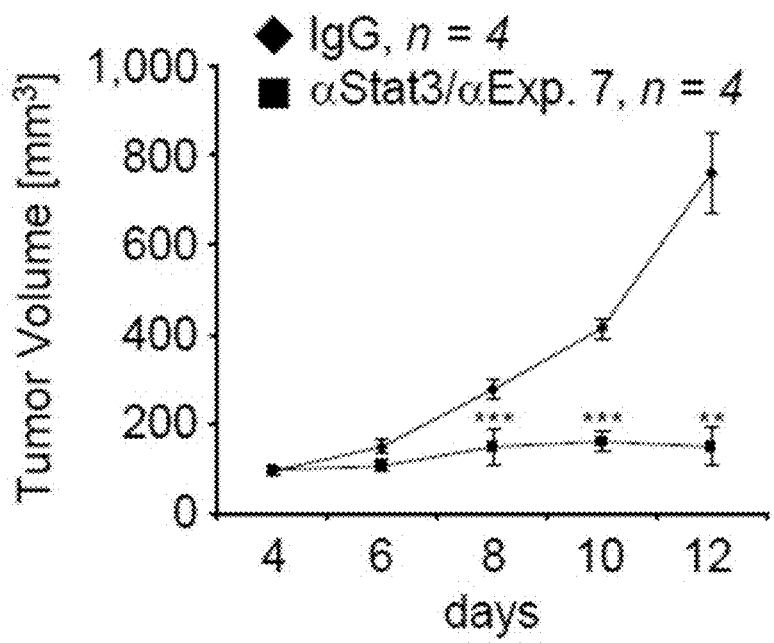
FIGS. 11A, 11B, 11C, and 11D show in vivo effects of the duo-antibody therapy in an artificial tumor model. Tumors were grown by engrafting STAT3-deficient MEF cells stably reconstituted with STAT3 wt into athymic nu/nu mice and treated as indicated.
Figure 11B:
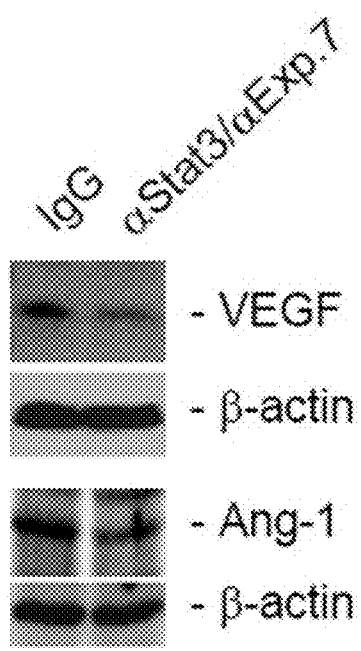
Figure 11C:
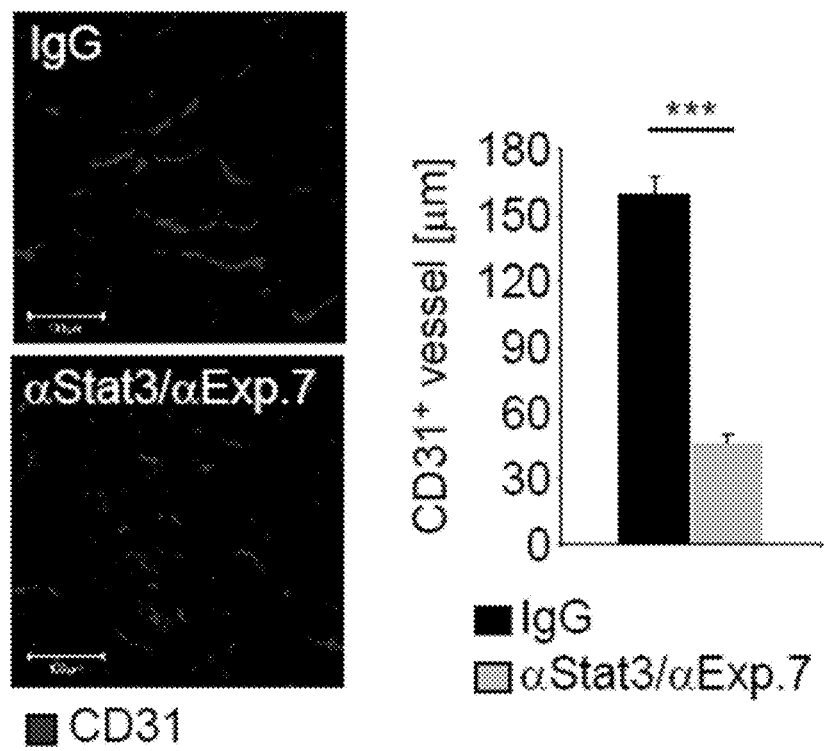
Figure 11D:
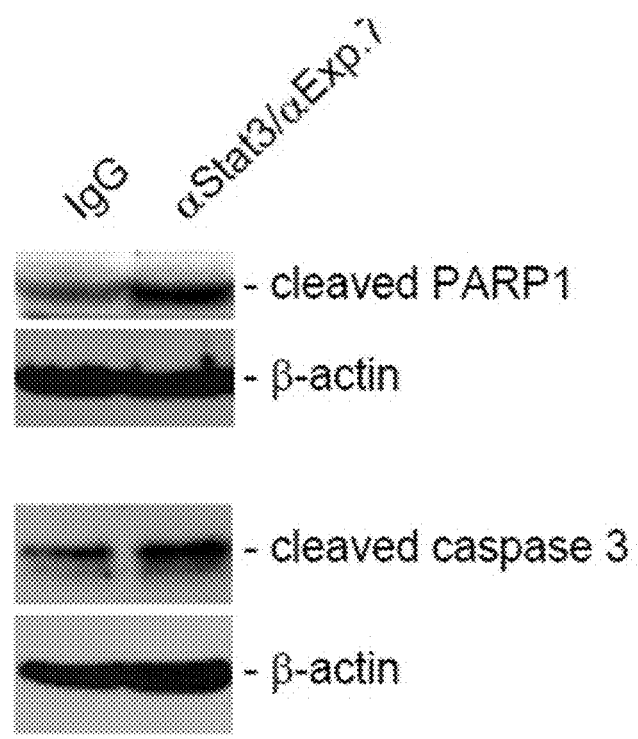
Figure 12A:
FIGS. 12A, 12B, and 12C show the duo-antibodies are efficiently internalized in cell cytoplasm in tumor in vivo.
Figure 12B:
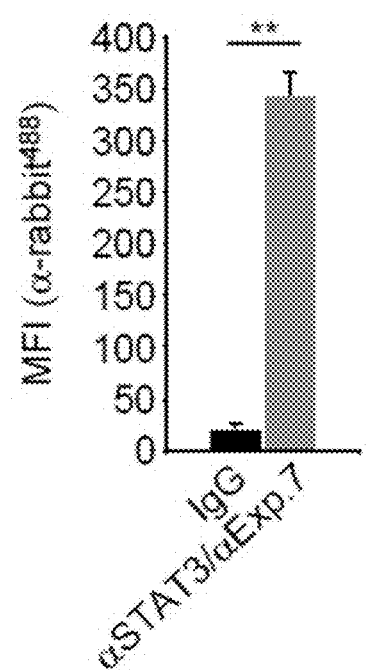
Figure 12C:
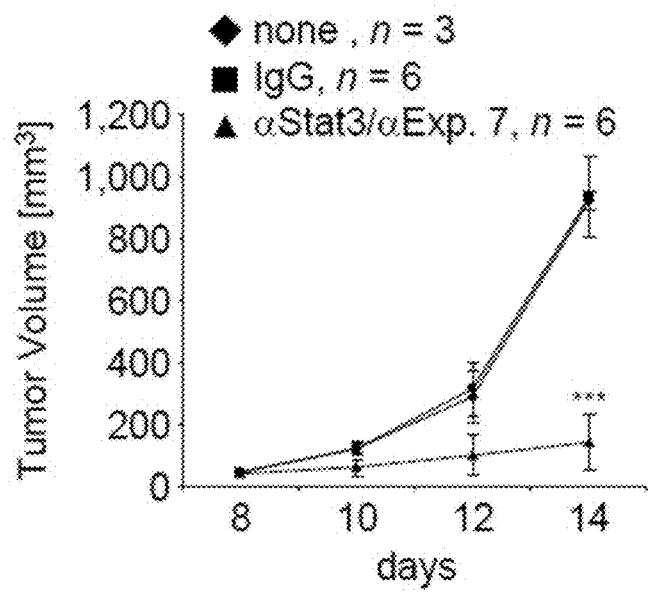

The ability of STAT3 and exportin 7 antibodies to inhibit STAT3 activity in vivo was tested in MEFs by blocking nucleocytoplasmic shuttling. Results from these experiments are shown in FIGS. 10A, 10B, 10C, 11A, 11B, 11C and 11D. Treating tumor-bearing mice with antibodies against exportin 7/STAT3 resulted in strong antibody intracellular uptake in tumors (FIGS. 10A and 12A), and significant tumor growth inhibition (FIGS. 3A, 11A and 12B). Single antibody treatment with either STAT3 or exportin 7, in combination with IgG control antibody, only marginally inhibited tumor growth (FIG. 3A). The two-antibody treatment was also accompanied by disruption of exportin 7-mediated STAT3 interaction with Nup153 and Nup50 (FIG. 3B). Treating tumor-bearing mice with STAT3/exportin 7 antibodies, but not with either one alone, was able to disrupt tumor vasculature and tumor proliferation significantly (FIGS. 3C and 3D), inhibit expression of STAT3 downstream genes involved in tumor cell survival, and proliferation (FIG. 3E). The efficacy of the two-antibody treatment was also tested in a human xenograft tumor model. Treating mice bearing human U87 glioma tumors with STAT3/exportin 7 antibodies was able to reduce tumor growth significantly (FIG. 3F) and prevent STAT3 binding to its DNA site (FIG. 3G). Tumor growth inhibition was associated with substantial increase in apoptotic tumor cells and reduction of tumor vasculature as visualized by intravital-multiphoton microscopy (FIGS. 3H and 3I).

Figure 4A:
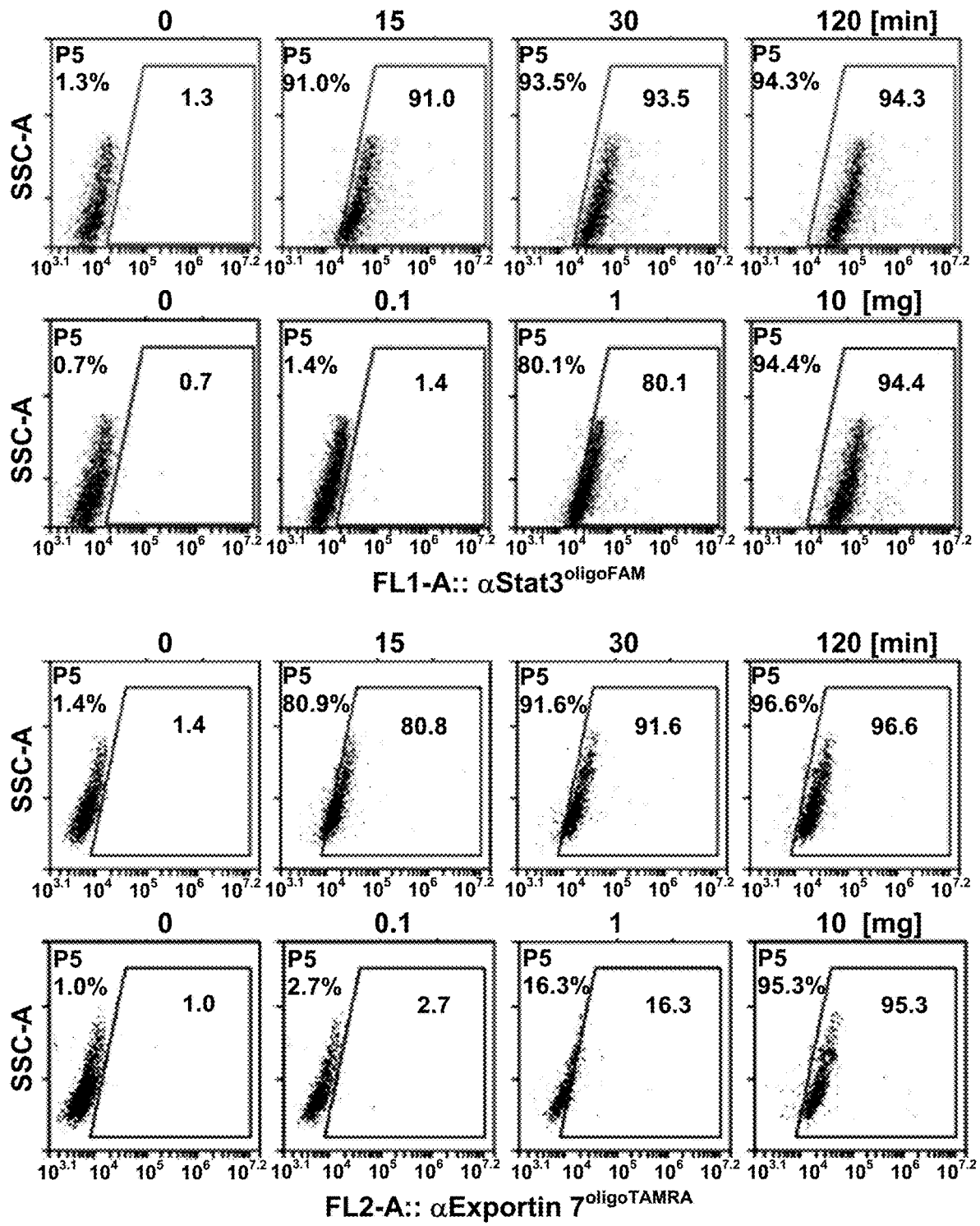
FIGS. 4A, 4B, 4C, 4D, 4E, 4F, 4G, 4H and 4I show potent antitumor efficacy by cell-penetrating STAT3 and Exportin 7 antibodies modified with phosphorothioated nucleic acids.
Figure 4B:
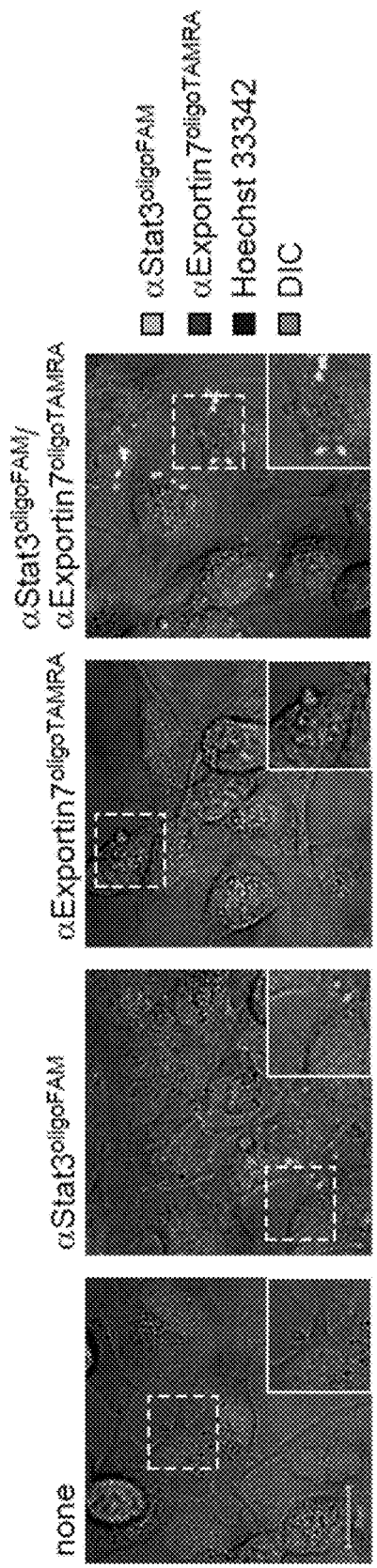
Figure 13A:
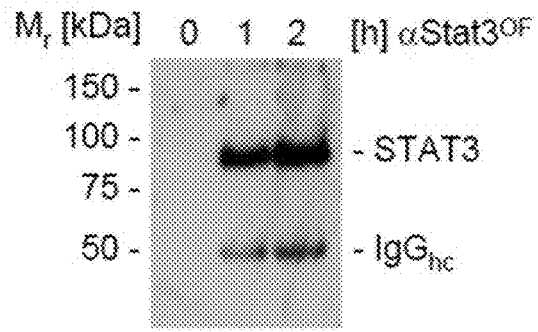
FIGS. 13A and 13B show recognition of intracellular targets by self-delivering antibodies. Human glioma U251 cells were treated with 10 μg of αStat3 (FIG. 13A) or αExportin 7 (FIG. 13B) antibody modified with phosphorothioated oligonucleotide, respectively, for indicated times. Whole cell lysates were prepared and cleared from cell debris before agarose beads were added to induce immunoprecipitation at 4° C. over night. Precipitates were carefully washed and subjected to Western blot analysis to determine antibody target recognition kinetics.
Figure 13B:
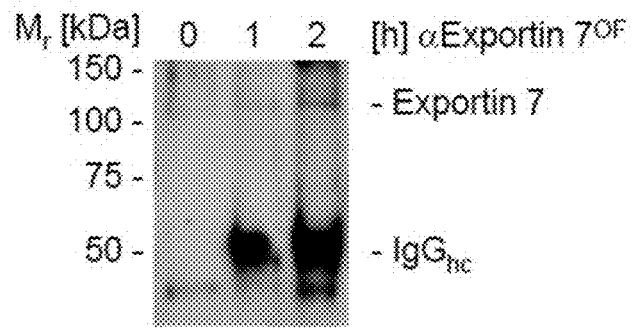
Figure 14:
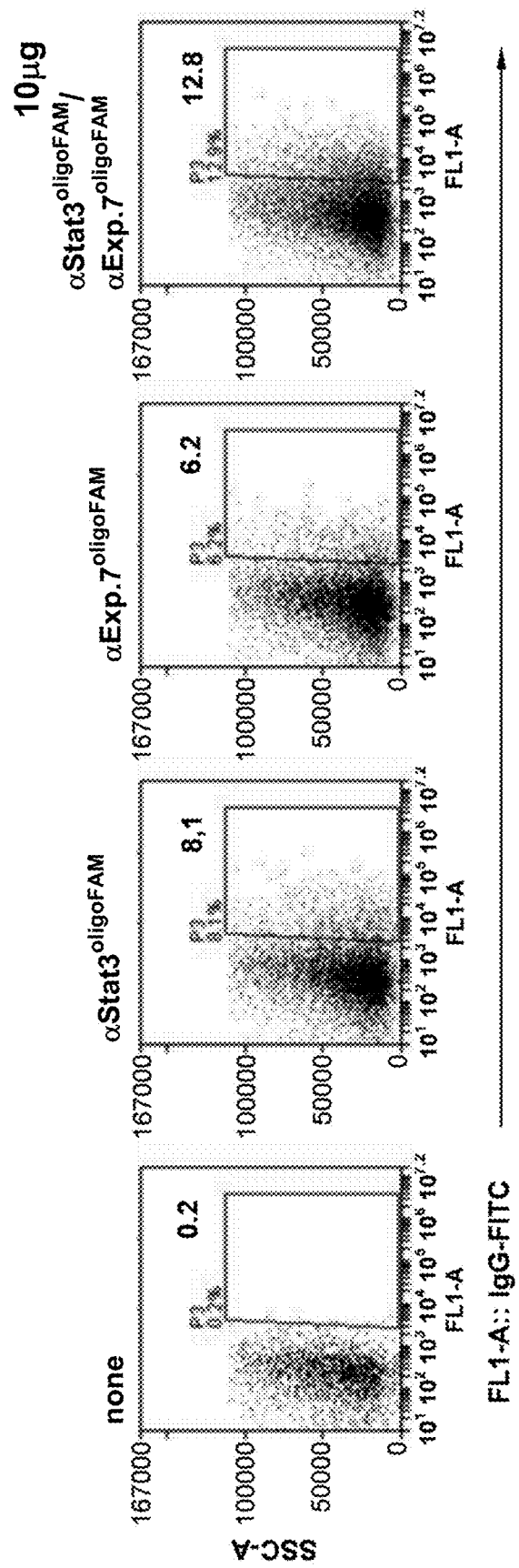
FIG. 14 are graphs showing in vivo intratumoral uptake of cell-penetrating antibodies. The intracellular uptake of the phosphorothioated nucleic acid-modified antibodies conjugated to fluorescent oligonucleotides (oligoFAM) by tumors in vivo was assessed 2 hours after local administration. Mouse melanoma B16 tumors were dissected and single-cell suspension was prepared for flow cytometric analysis to determine the FAM(FITC)+ cell population. Tumor bearing mice were treated with indicated modified antibody/antibodies, a total dose of 10 μg of oligo-modified antibodies was given in the single treatment.
Figure 15A:
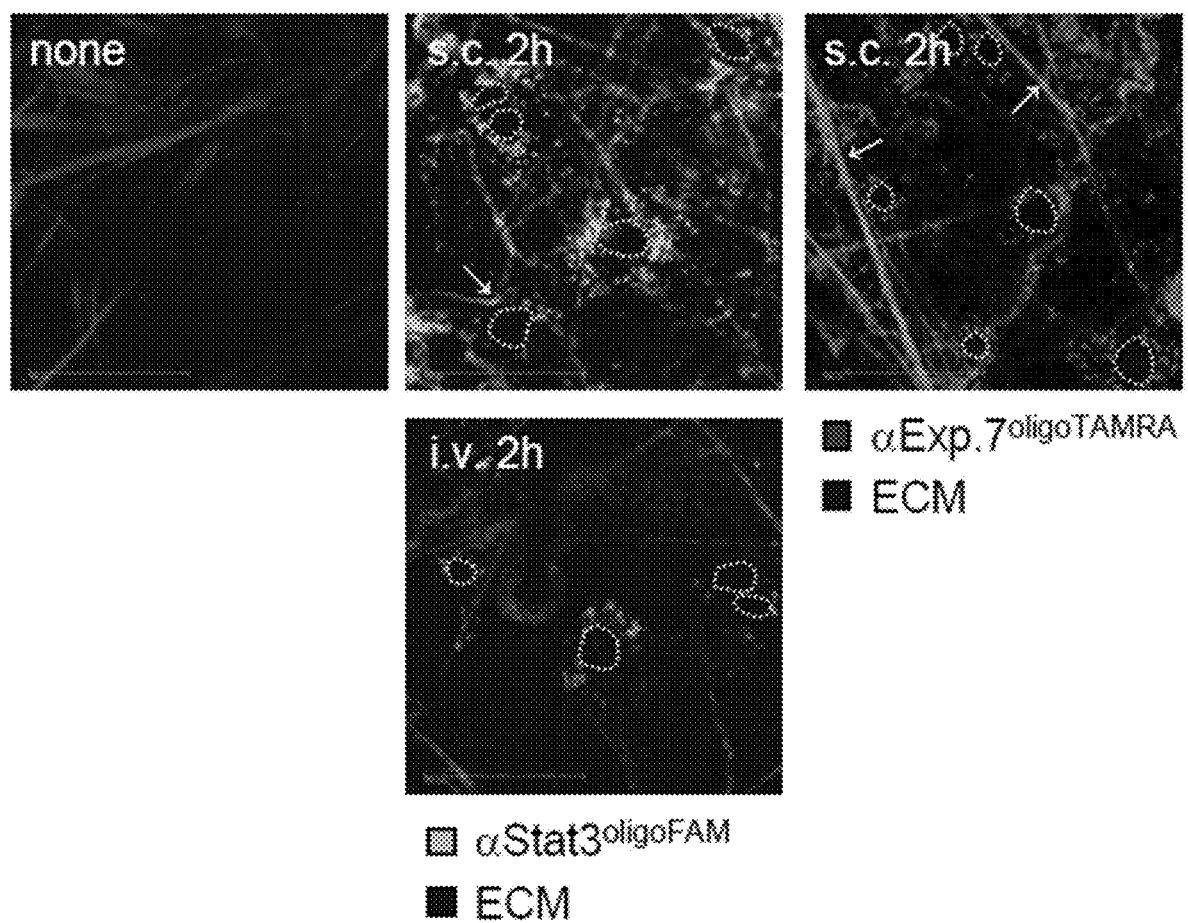
FIGS. 15A and 15B show homing and biostability of cell-penetrating antibodies to tumor tissue in vivo.
Figure 15B:
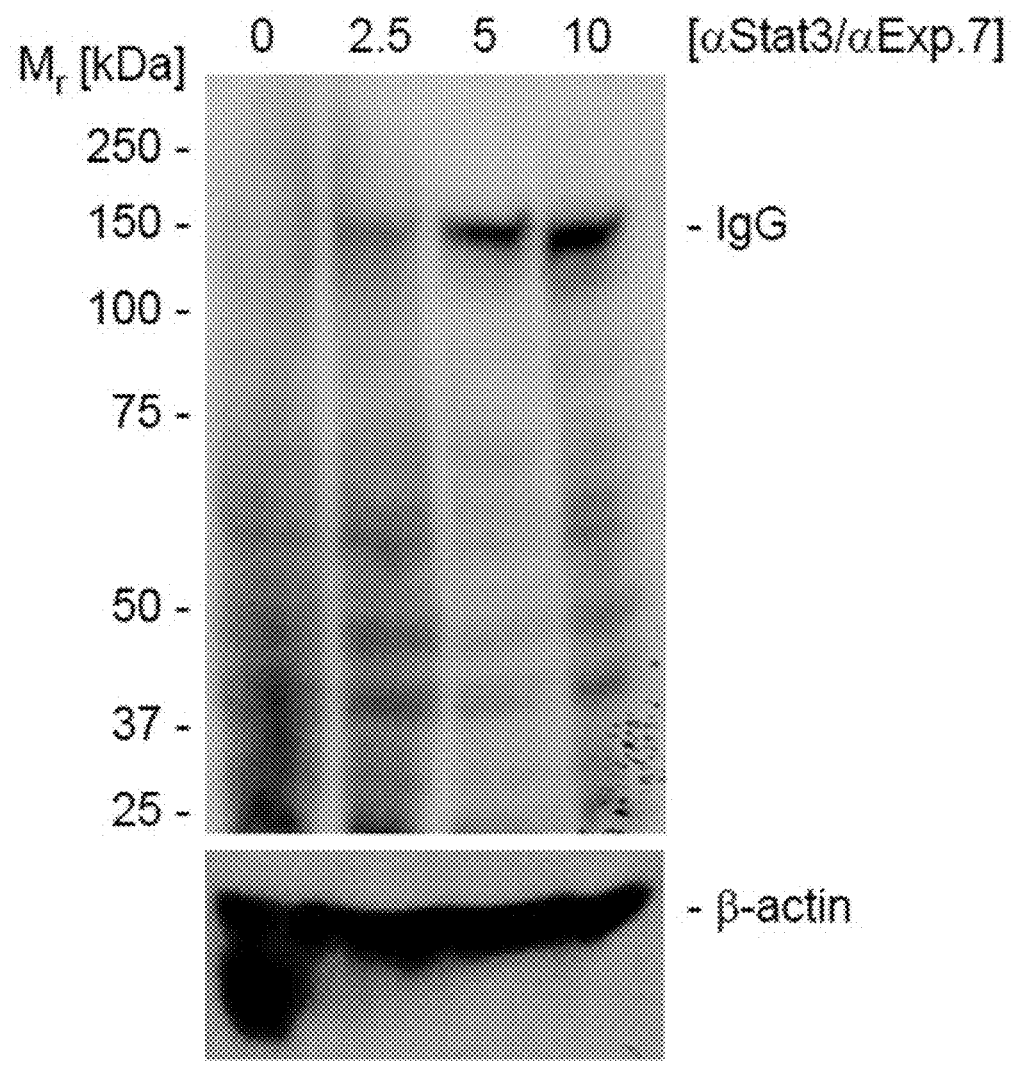
Figure 16A:
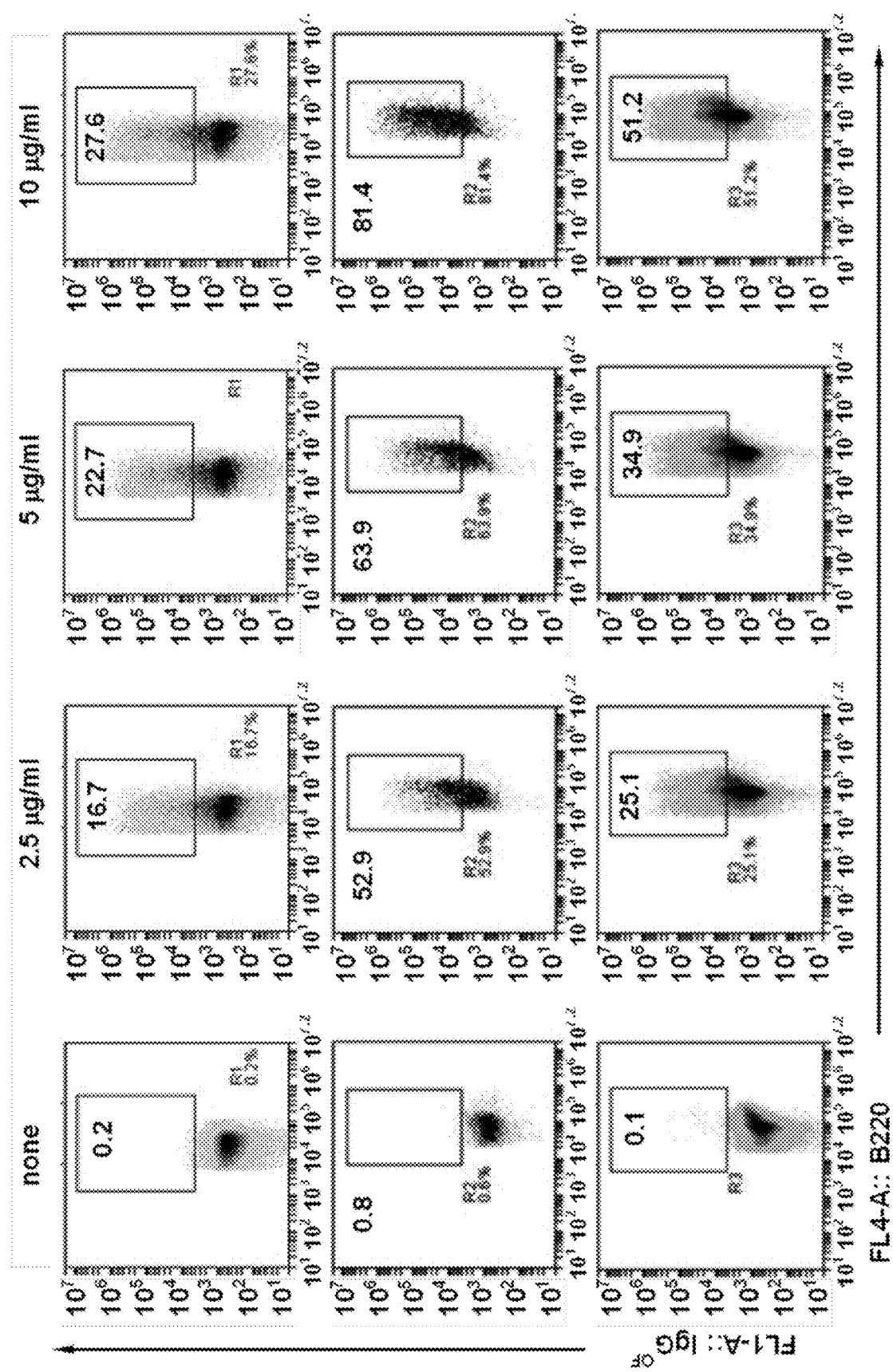
FIGS. 16A and 16B show cellular internalization of phosphorothioated nucleic acid-modified cell-penetrating antibodies into immune cell populations.
Figure 16B:
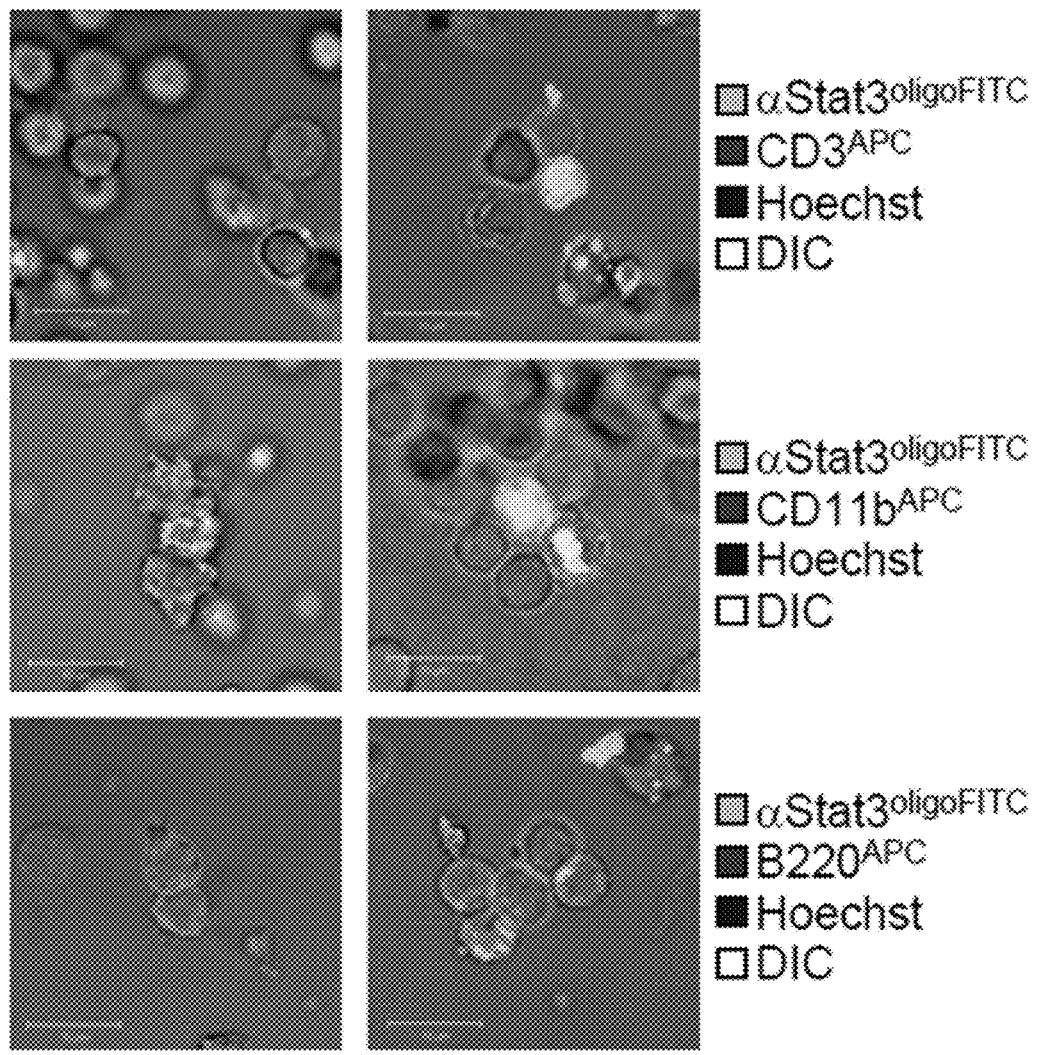
Figure 17A:
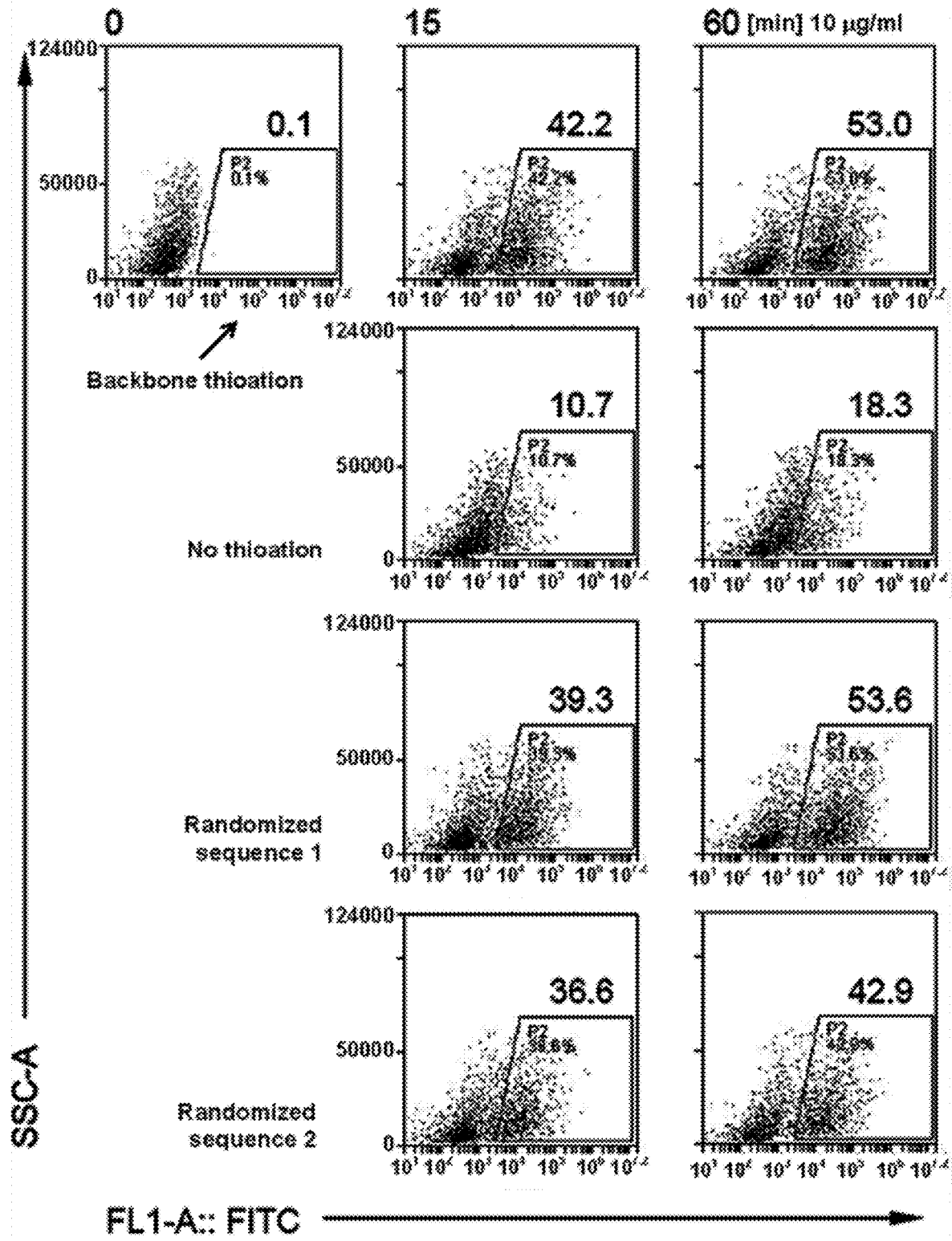
FIGS. 17A and 17B show oligonucleotide backbone phosphorothioation is critical for intracellular antibody delivery and antigen recognition. Human glioma U251 cells were treated with 10 µg/ml fluorescently labeled phosphorothioated nucleic acid-modified αStat3 antibodies for indicated times. Single cell suspensions were analyzed by flow cytometry for uptake of modified antibody.
Figure 17B:
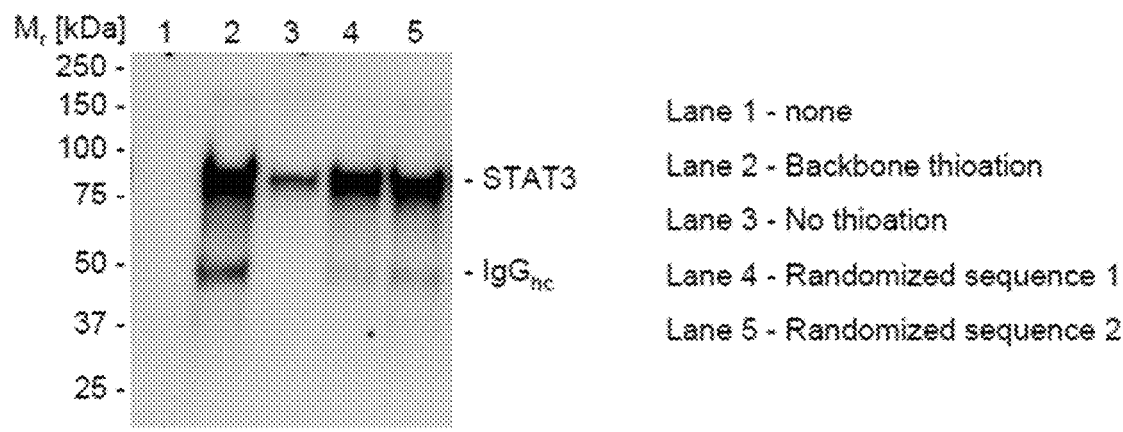
Figure 18:
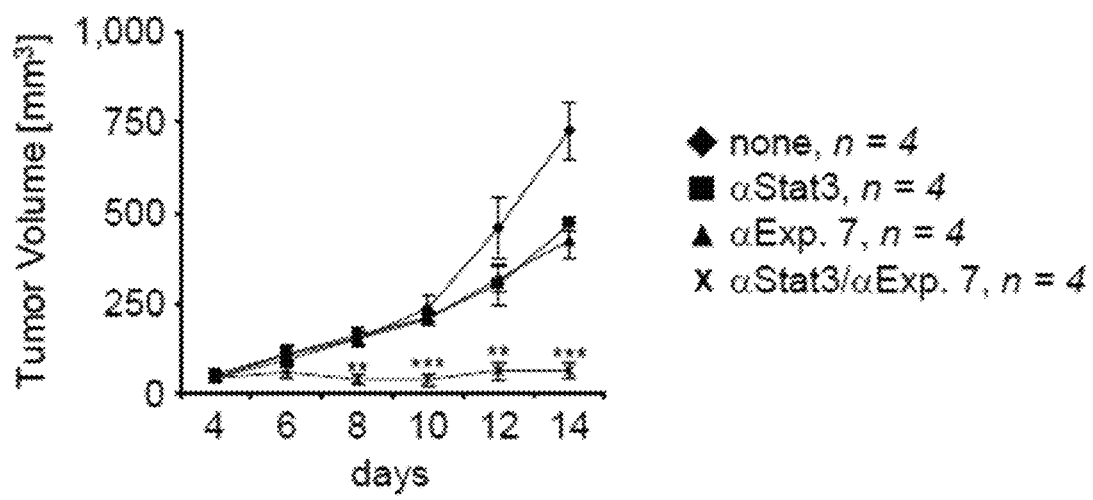
FIG. 18 is a graph showing potent antitumor effects by the modified STAT3/exportin 7 antibodies in a xenograft human glioma model. Human glioma U251 cells (2×10$^6$) were injected subcutaneously into immunocompromised NSG/NOD mice. When the tumors reached average 5 mm in diameter, mice were treated locally every other day, with 10 µg of indicated, modified antibodies. Tumor volume was assessed every other day. SD shown. Student's T-test *, P<0.001; , P<0.01; *P<0.05.

The results so far demonstrate that a transcription factor such as STAT3 can be targeted by antibodies. However, lipid carriers were relied upon to deliver antibodies intracellularly. Methods to enable antibodies and proteins to penetrate into cells for efficient cellular protein targeting remain elusive. A technology was developed for this purpose. Specifically, phosphorothioated oligonucleotides were attached to antibodies in an attempt to enable them to penetrate cells and target their intended molecules. Attachment of phosphorothioated oligonucleotides to STAT3 or exportin 7 polyclonal IgG antibodies led to efficient cellular internalization of the antibodies in the cell cytoplasm in vitro, in a time- and dose-dependent manner (FIGS. 4A and 4B). Notably, simultaneous delivery of the two modified antibody entities was demonstrated (FIG. 4B, right panel). Further characterization revealed intended target recognition by the modified antibodies in the cytoplasm (FIGS. 13A and 13B). Moreover, fluorescently labeled, phosphorothioated oligonucleotide modified antibodies were detected in tumors upon both local and systemic administrations (FIGS. 14 and 15A). Intact oligonucleotide modified antibodies were found in tumor tissues eight days after the last systemic treatment (FIG. 15B), indicating a robust biostability of the modified antibodies. In addition to penetrating cancer cells, the oligonucleotide modified antibodies can also enter immune cells (FIGS. 16A and 16B). DNA backbone phosphorothioation but not sequence specificity of oligonucleotides attached to antibodies is critical for both cellular uptake and subsequent target/antigen recognition (FIGS. 17A and 17B).

Figure 4C:
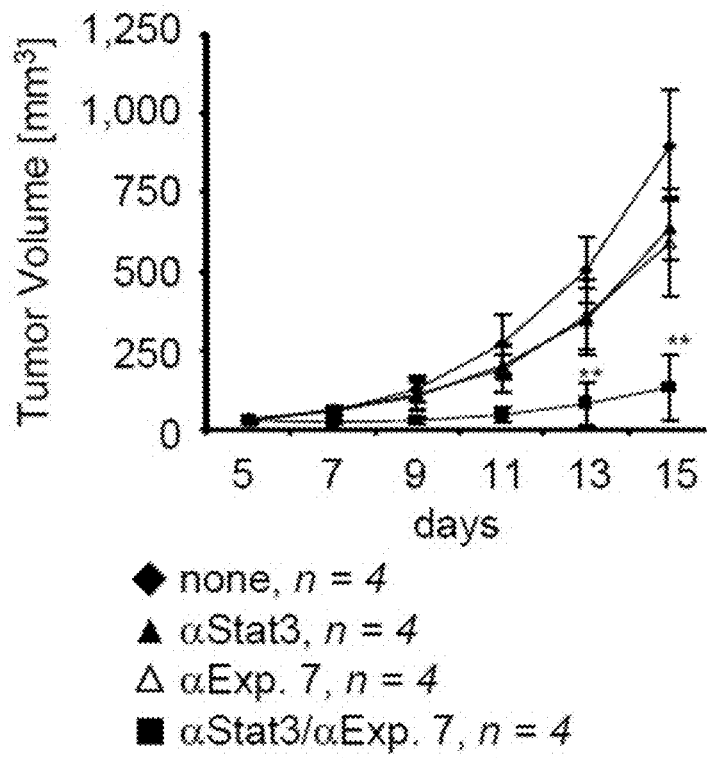
Figure 4D:
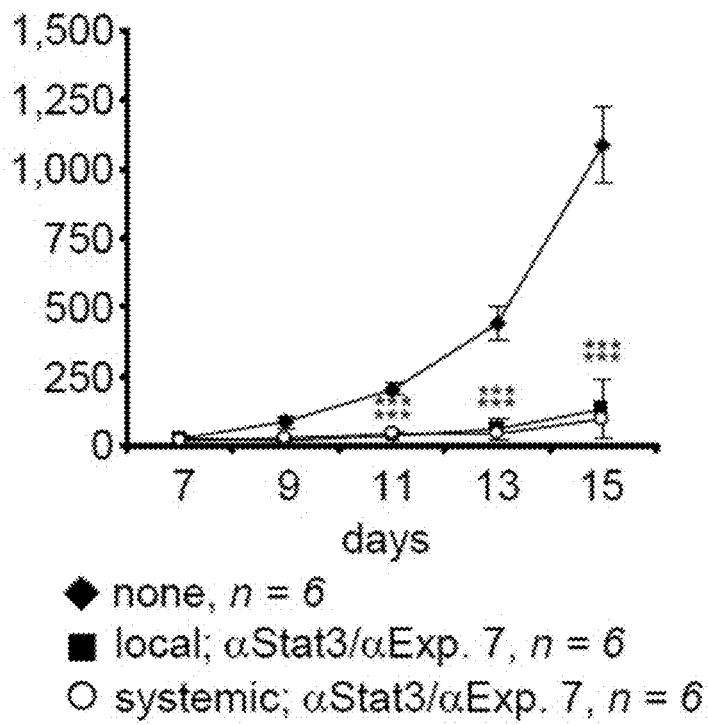
Figure 4E:
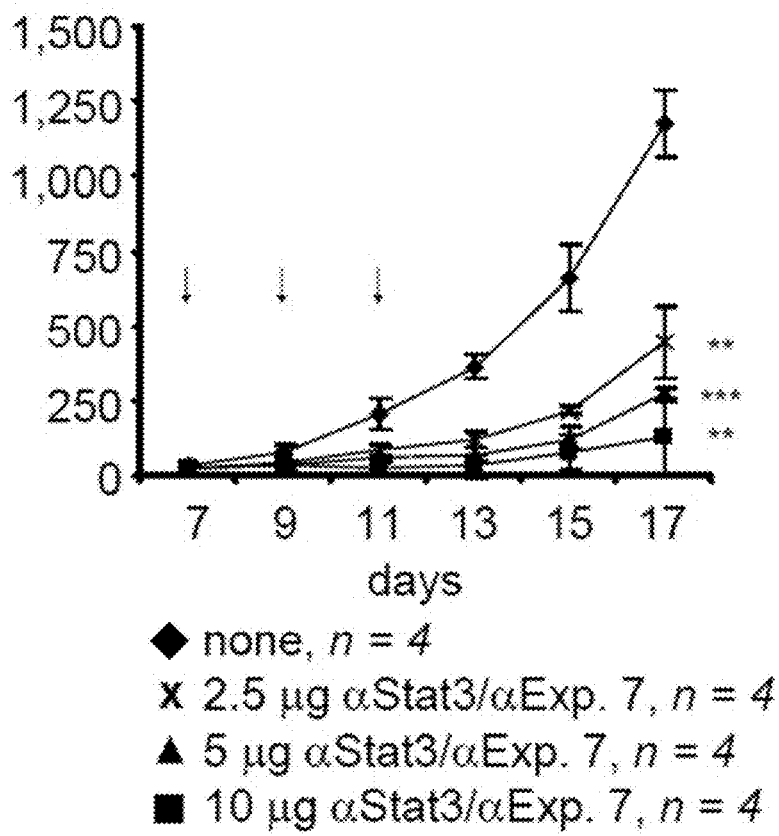
Figure 4F:
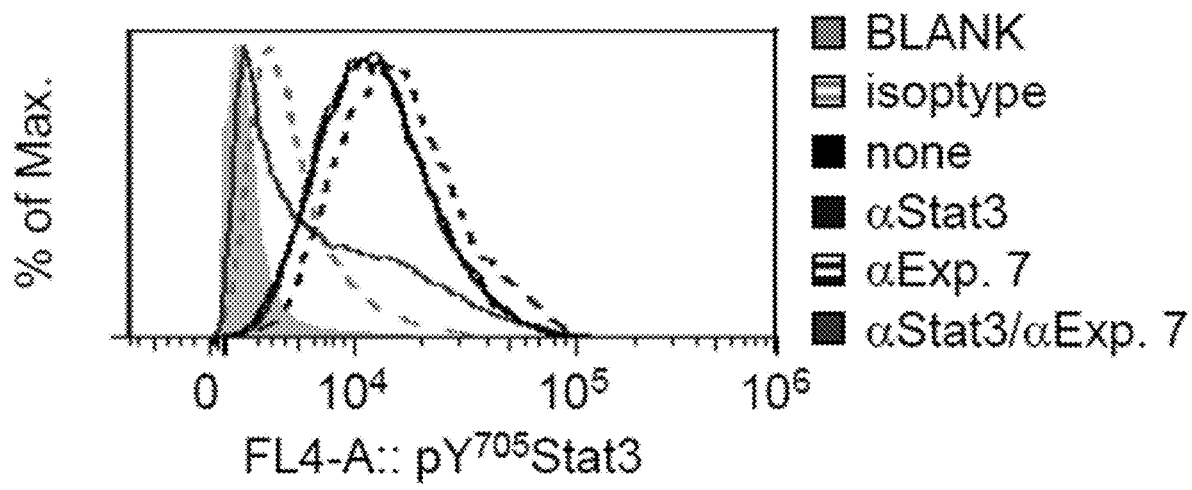
Figure 4G:
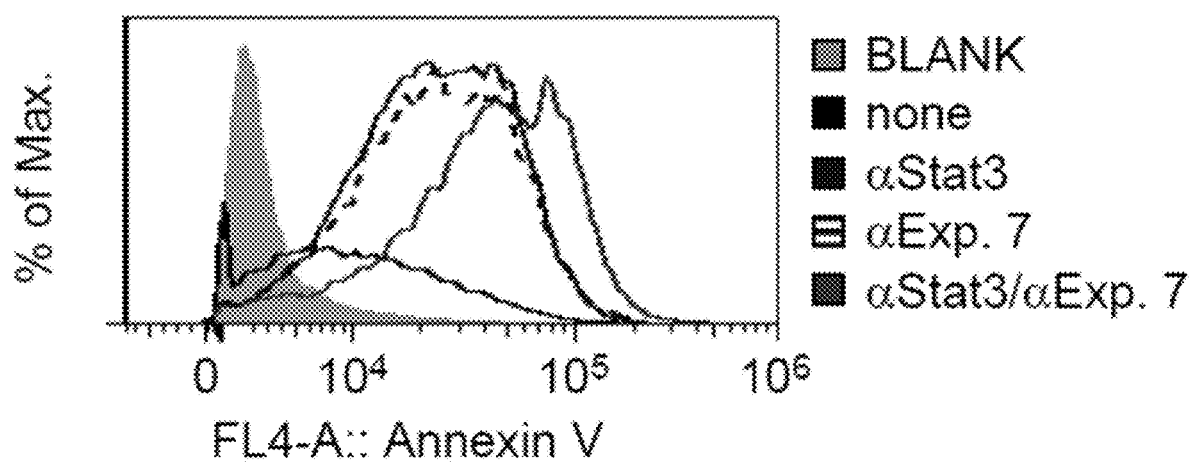

To assess the anti-tumor efficacy of phosphorothioated oligonucleotide-modified antibodies, STAT3/exportin 7 antibodies were administered locally to melanoma B16 tumor bearing mice, as well immuno-deficient mice bearing human U251 glioma. Compared to untreated mice and those treated with single antibodies, tumor growth kinetics in both models were significantly reduced in mice receiving the combination of modified STAT3/exportin 7 antibodies (FIGS. 4C and 18), which was accompanied by drastically decreased STAT3 activity (FIG. 4F), and increased apoptotic cell death (FIG. 4G).

Figure 4H:
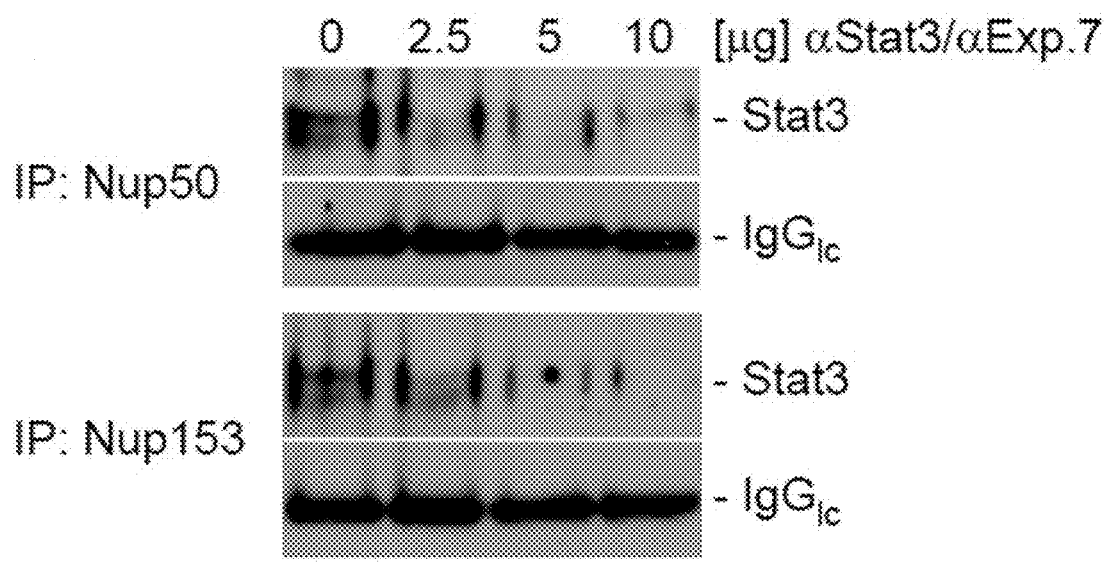
Figure 4I:
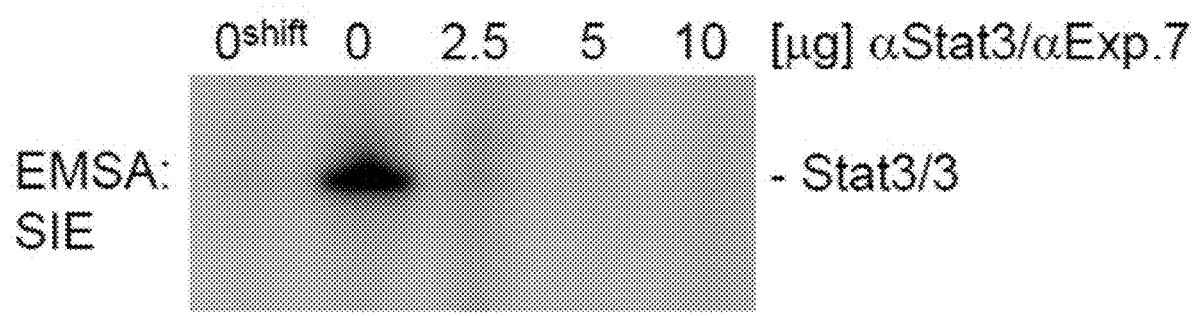

The antitumor efficacy of the modified STAT3/exportin 7 antibodies was tested via systemic administrations. Systemic delivery of the modified STAT3/exportin antibodies also showed very dramatic anti-tumor effects on tumor growth (FIG. 4D). The phosphorothioated nucleotide-modified antibodies efficiently reached and permeated tumor tissues, and exerted antitumor functions (FIG. 15A). The anti-tumor efficacy of combined antibody treatment was then assessed given systemically in descending doses down to 2.5 μg total antibodies per treatment. Potent antitumor effects remained when systemic treatment was discontinued after only three treatments (FIG. 4E), accompanied by inhibition of STAT3 compartmental turnover, as indicated by a reduction in STAT3 interaction with nucleoporins 50 and 153 (FIG. 4G). Moreover, systemic treatment of tumor bearing mice with the modified STAT3/exportin antibodies effectively diminished STAT3 DNA-binding capability in tumors (FIG. 4H).

The need to use antibodies to target intracellular molecules is compelling. Although it has been reported that antibodies can diffuse into cancer cells to block intended proteins in vivo, no molecular mechanisms were provided, and it was speculated that the antibody uptake by cancer cells is mediated by B cells. A methodology to modify antibodies to make them self-penetrating is described herein, enabling them to target intracellular molecules effectively even with systemic administration. Direct experimental evidence is provided that targeting two discrete parts of a protein or two proteins in a complex with antibodies can reduce nucleocytoplasmic shuttling required for re-activation of transcription factors. In addition to STAT3, a nuclear protein deemed to be impossible to be targeted by antibodies, the cell-penetrating antibody technology can be broadly used to target various intracellular proteins (e.g., oncogenic proteins and intracellularly residing viral proteins).

Example 2

Effective Cell-Penetrating Protein Delivery Technology

In the present example, it was demonstrated that modifying antibodies with phosphorothioated oligos enables them to penetrate cells where they bind to the intended intracellular target antigens/molecules. Further, the ability of the modified antibodies to specifically detect intracellular targets by flow cytometry and confocal microscopy was shown in living cells, as well as detecting protein in its native form by Western blotting. Furthermore, it was demonstrated that such modified antibodies can be used to effectively block the activities of intracellular tyrosine kinases (phospho-Src), intracellular/nuclear viral proteins (HPV16/18 E6 protein) as well as transcription factors (STAT3).

Materials and Methods

Localization of STAT3-GFP in living cells was imagined and analyzed using a LSM 510 Meta Inverted microscope (Zeiss) and bleaching experiments resulting in iFLAP imaging were performed (Herrmann, et al., *J. Cell Sci.* 120:3249-3261 (2007)). Briefly, YFP and CFP emission signals of the STAT3-CFP-YFP fusion protein were equally amplified. Using λ=514 nm laser line, the YFP moiety of the fusion protein was bleached for several rounds, interrupted by image acquisition. In a post acquisition procedure, the algorithm $I=1-I_{YFP}/I_{CFP}$ was applied to collected images resulting in the spatial distribution of STAT3-CFP-YFP as a function of time. Tumor sections were stained using protocols for indirect immunofluorescence as described previously (Herrmann, et al., *Cancer Research* 70:7455-7464 (2010)).

Delivery of antibodies against STAT3 (Santa Cruz, sc-482), exportin 7 (Santa Cruz, sc-98639), or GFP (Rockland) in cell culture was achieved using a lipid carrier system (GenLantis, BP509604) according to the manufacturer's instructions. In vivo, a total dose of 10 μg immunoblobulins in complex with the lipid carrier (GenLantis, BP509604) or oligo-nucleotide modified antibodies against STAT3 and exportin 7, respectively, was administered for each treatment.

Conjugation of oligos to antibody. Oligonucleotide sequences used for conjugation to antibodies:

```
phospothioated
                                    (SEQ ID NO: 2)
T*C*C*A*T*G*A*G*C*T*T*C*C*T*G*A*T*G*C*T non-phospothioated
                                    (SEQ ID NO: 3)
TCCATGAGCTTCCTGATGCT phospothioated scrambled 1 (scr1)
                                    (SEQ ID NO: 6)
T*C*G*T*A*G*T*C*C*T*T*C*G*A*G*T*A*C*C*T phospothioated scrambled 2 (scr2)
                                    (SEQ ID NO: 5)
C*C*C*A*G*G*A*G*T*C*T*C*C*T*G*A*T*T*T*T phosphothioated scrambled 3 (scr3)
                                    (SEQ ID NO: 7)
T*A*G*A*T*G*A*C*C*T*T*C*C*T*G*C*T*G*C*T
```

T, thymine; A, adenine; G, guanine; C, cytosine; (*) indicates phosphorothioation. Oligonucleotides (200-300 nmol) were reduced by a 30-molar excess of TCEP (400 μL, 5 mM TEAA, pH 6.8) for 2 hours at room temperature (RT) under argon and purified by reverse phase chromatography (PRP1, linear gradient from 5 mM TEAA to 95% MeOH over 30 min). Removal of the thiol protecting group was confirmed by mass-spectrometry (LTQ FT, Thermo) followed by lyophilization. The reduced oligonucleotide was redissolved in 0.5 mL water/DMSO (4:1), a 25-fold excess of vinyl sulfone was added, the pH was adjusted to 8.5, reacted for 3 hours at RT under argon, purified by reverse phase HPLC (as above), the correct product confirmed by mass-spectrometry and the sample lyophilized (VS-oligonucleotides). Alternatively, oligonucleotides were not subjected to removal of the thiol protecting group and were further processed as follows (SSR-oligonucleotide). Polyclonal IgG (1.6 mg, dialyzed in PBS for 48 h) was reduced with a 30-molar excess of TCEP in PBS for 2 h at 37° C. under argon. After removal of the excess TCEP (Zeba spin column, Thermo; 2,000 rpm for 2 min), the reduced antibodies were reacted with a 20-molar excess of VS-oligonucleotide or SSR-oligonucleotide at pH 7.5 under argon overnight. Successful oligo-to-antibody-conjugation was confirmed by IEF gel electrophoresis (pH 3-9, GE Health Sciences) comparing unconjugated to conjugated antibody.

Results and Discussion

Figure 23A:
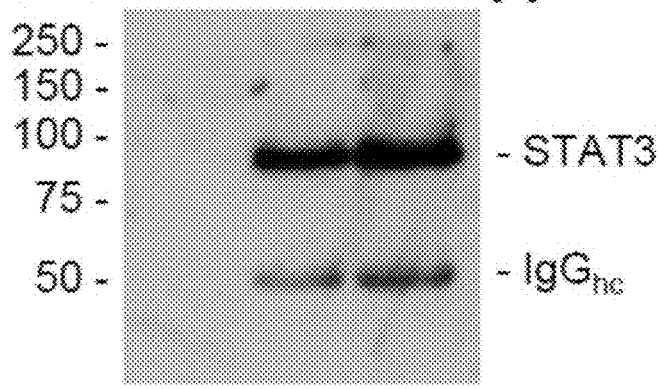
FIGS. 23A, 23B, 23C, 23D, 23E, 23F, and 23G show phosphorothioated-oligo-modified antibodies internalize and recognize intracellular targets.
Figure 23B:
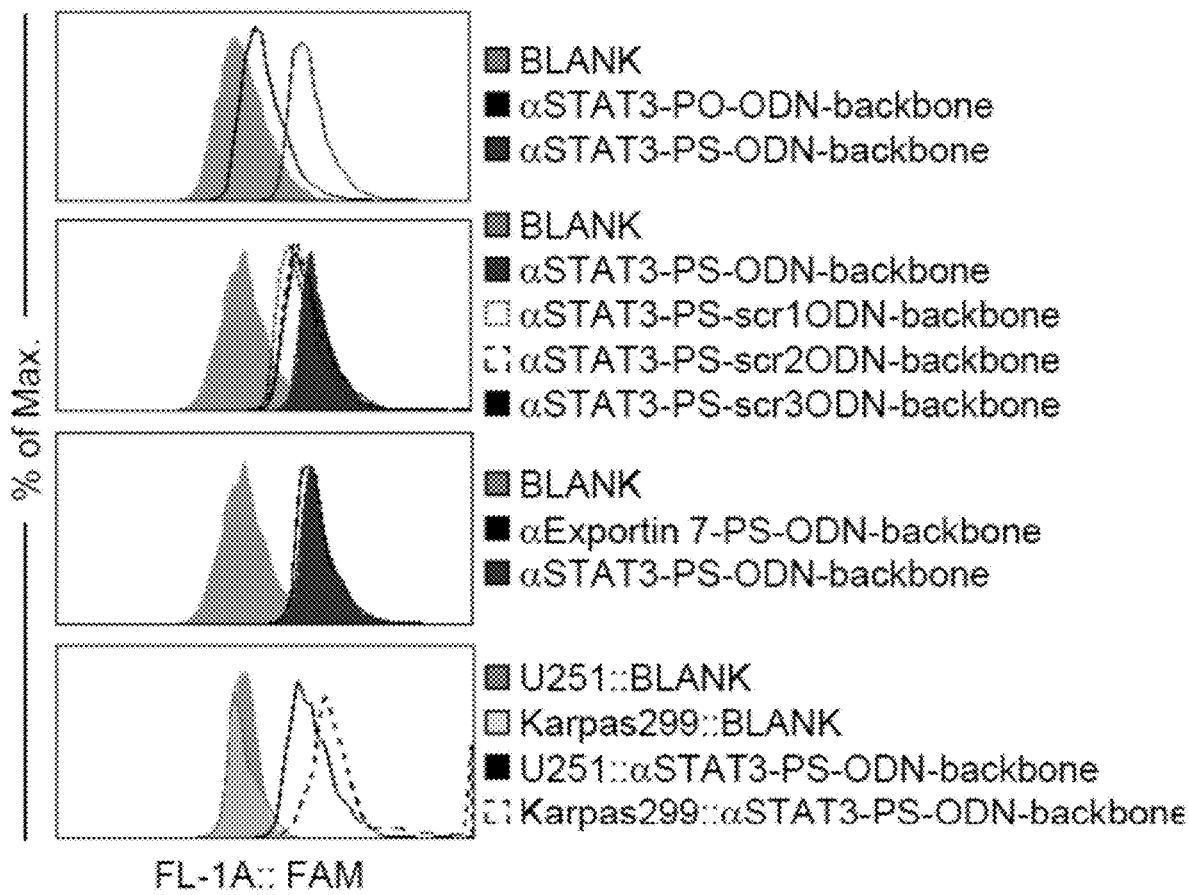
Figure 23C:
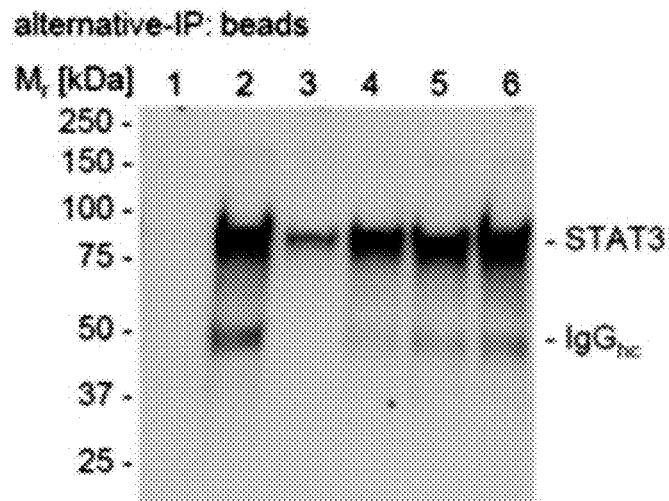
Figure 23D:
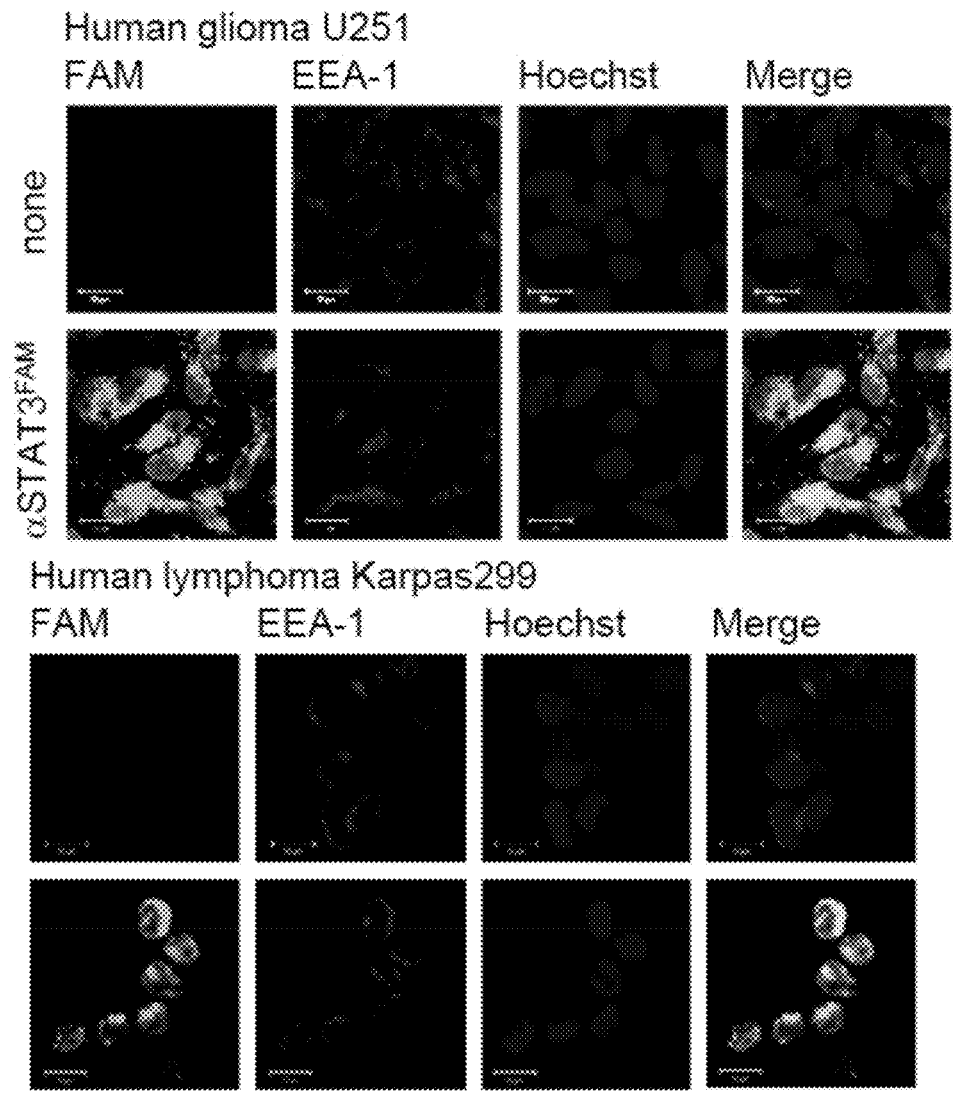
Figure 28:
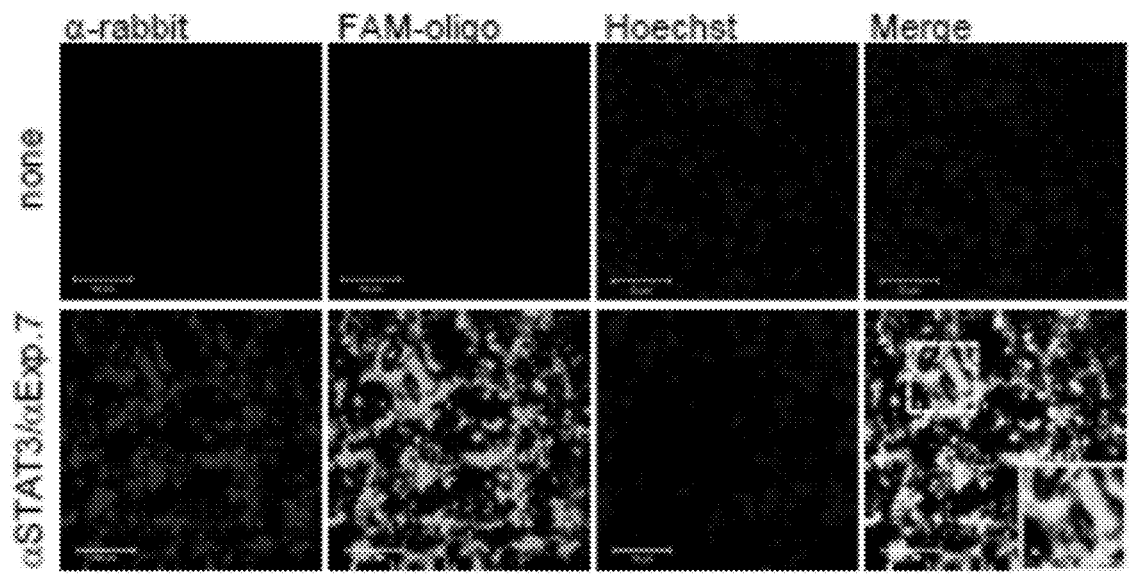
FIG. 28 are images showing co-localization of the phosphorothioated oligos (FAM-positive) and delivered antibodies in vivo. Human U251 glioma were treated locally every other day for three times before tumors were dissected. Tumor sections were stained with labeled antibodies against IgG rabbit species. Stained sections were analyzed by confocal microscopy. Inset shows magnification of indicated area (white box, dashed). Scale bar, 50 μm.

Cell penetration and target recognition of the modified antibodies. Modifying STAT3 IgG antibodies with phosphorothioated oligo-nucleotides led to cellular internalization of the antibodies and intended target/antigen recognition in living cells in vitro (FIG. 23A). This is evidenced by detection of antibody-target complex using an alternative immunoprecipitation: adding modified antibodies to living cells to allow their binding to the target in its native form, followed by lysing the cells and precipitation with agarose beads prior to electrophoresis. It was confirmed that the antibody and the phosphorothioated oligos are co-localized in vivo (FIG. 28). It was further shown that DNA backbone phosphorothioation of different oligo-nucleotides is able to achieve antibodies' cellular uptake and subsequent target/antigen recognition, as evidenced by both flow cytometric analysis and Western blotting (FIG. 23B, 23C). In addition, it was shown that phosphorothioation modification of exportin 7 antibodies facilitated the antibodies internalization (FIG. 23B) and that the internalization of the modified antibodies was not limited to a particular cell type (FIG. 23B). It was also demonstrated by confocal imaging that the modified STAT3 antibodies could penetrate cell membrane and that they could be present outside the EEA-1+ endosomal compartment. In addition, the modified STAT3 antibodies could also enter nuclear compartment (FIG. 23D).

Figure 23E:
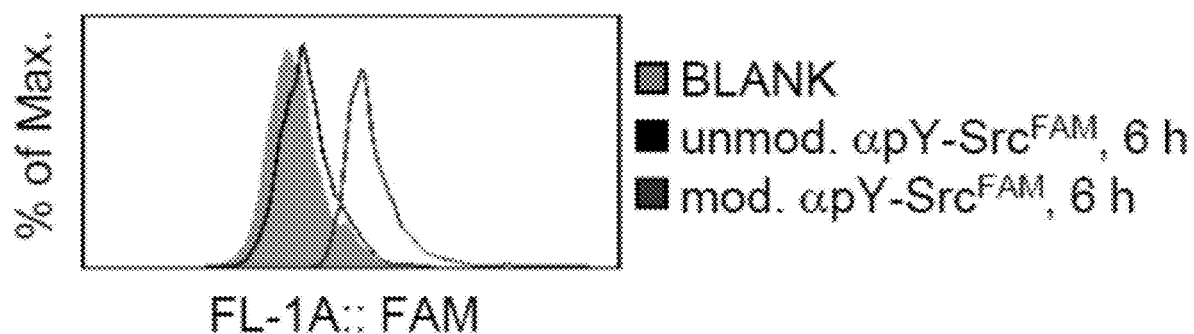
Figure 23F:
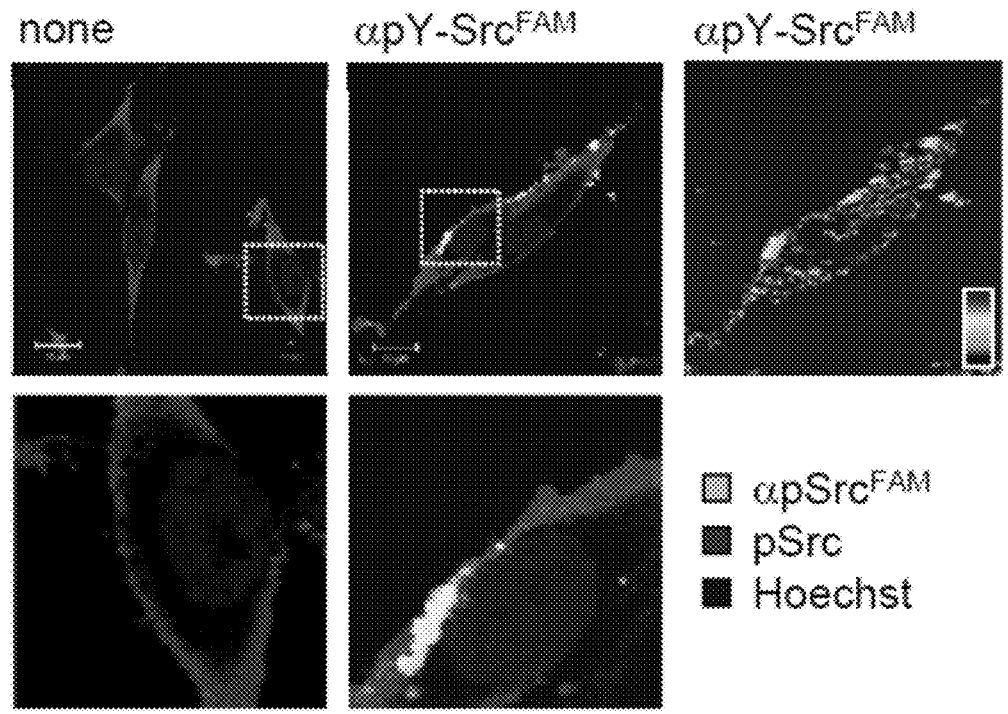
Figure 23G:
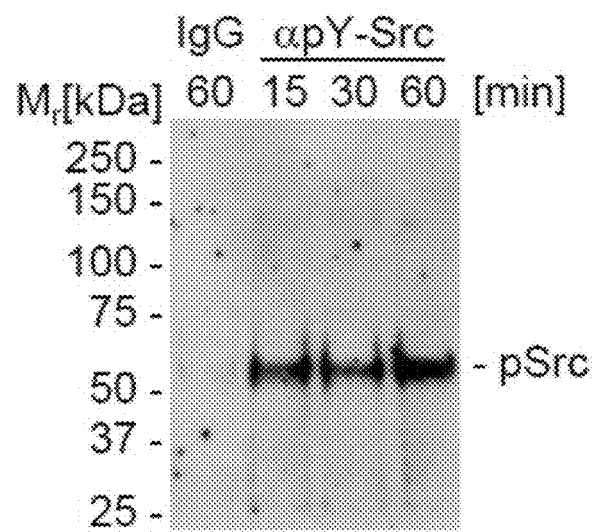

Further characterized in detail were phospho-Src (p-Src) antibodies modified with phosphorothioated oligos. The cell penetration ability of modified and unmodified p-Src antibodies was compared using flow cytometric analysis (FIG. 23E). In addition, confocal imaging, of cells with less fluorescent signals, indicated that the modified p-Src antibodies co-localized with p-Src (FIG. 23F). Moreover, the unique immuneprecipitation followed by Western blotting, in which antibodies were added to live cells before preparing cell lysates, confirmed that the modified p-Src antibodies were able to internalize into cells and bind to their intended target (FIG. 23G).

Figure 24:
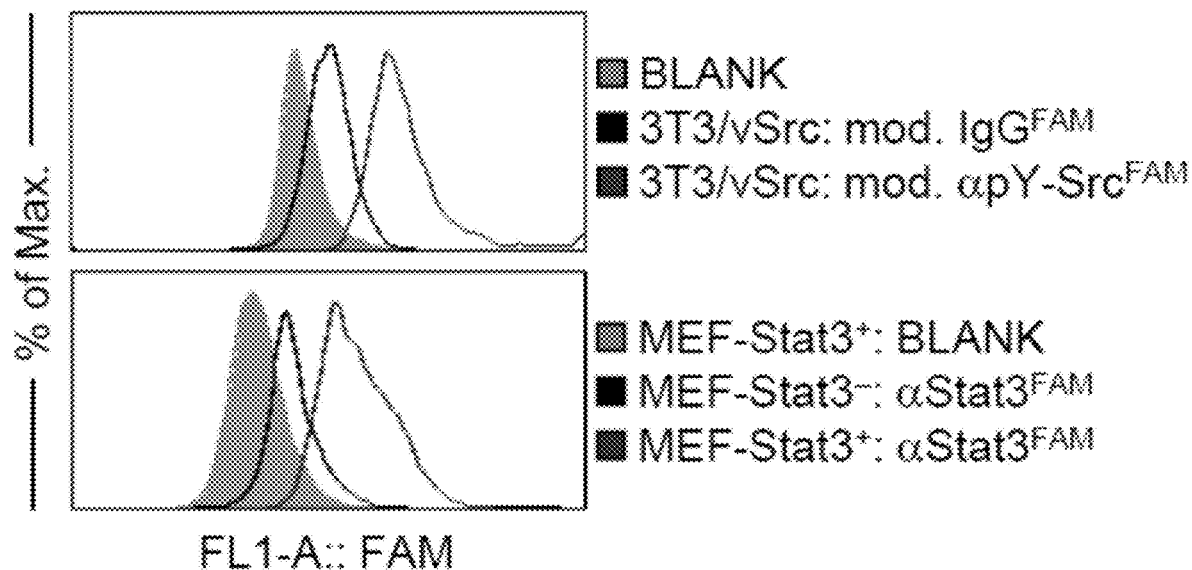
FIG. 24 are graphs of flow cytometry analyses showing modified antibody intracellular activities. Flow cytometric analyses indicate a requirement of target protein for intracellular retention of modified antibodies. Murine 3T3/vSrc cells were incubated with modified p-Src antibody or modified IgG antibody (upper panel). Modified Stat3 antibody (1 µg/ml) was incubated with either Stat3+ or Stat3− murine MEF cells for 2 hours before flow cytomtric analysis (lower panel). Oligos and antibodies attached to oligos through vinylsulfone were used in the experiments for these figures.

Target is required for cell-penetrating antibody intracellular retention. The data so far demonstrate that phosphorothioated oligos modified antibodies can penetrate into cells. It was shown that fluorescently labeled, modified p-Src antibodies but not the labeled modified IgG control antibodies were easily detectable by flow cytometric analysis in 3T3 fibroblasts transfected with v-Src (FIG. 24, top panel). Using mouse embryonic fibroblasts (MEFs) with or without Stat3, it was shown by flow cytometric analysis that Stat3 protein was required for retention of the phosphorothioated oligonucleotide modified Stat3 antibodies (FIG. 24, lower panel).

Figure 25A:
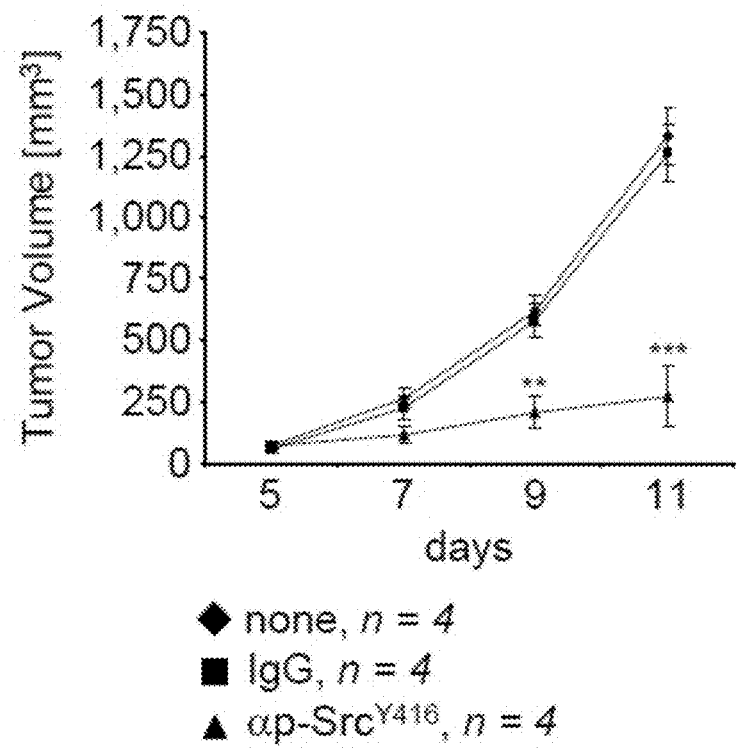
FIGS. 25A, 25B, 25C, 25D, 25E, and 25F, show antitumor effects by cell-penetrating p-Src antibodies.
Figure 25B:
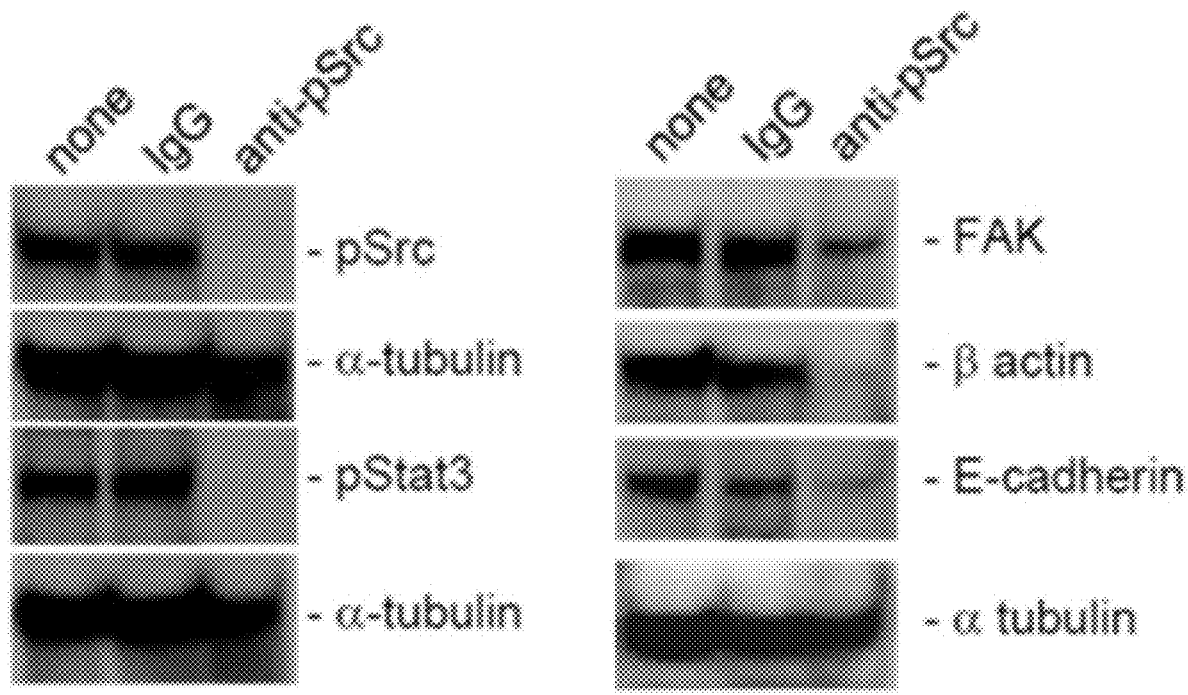
Figure 29:
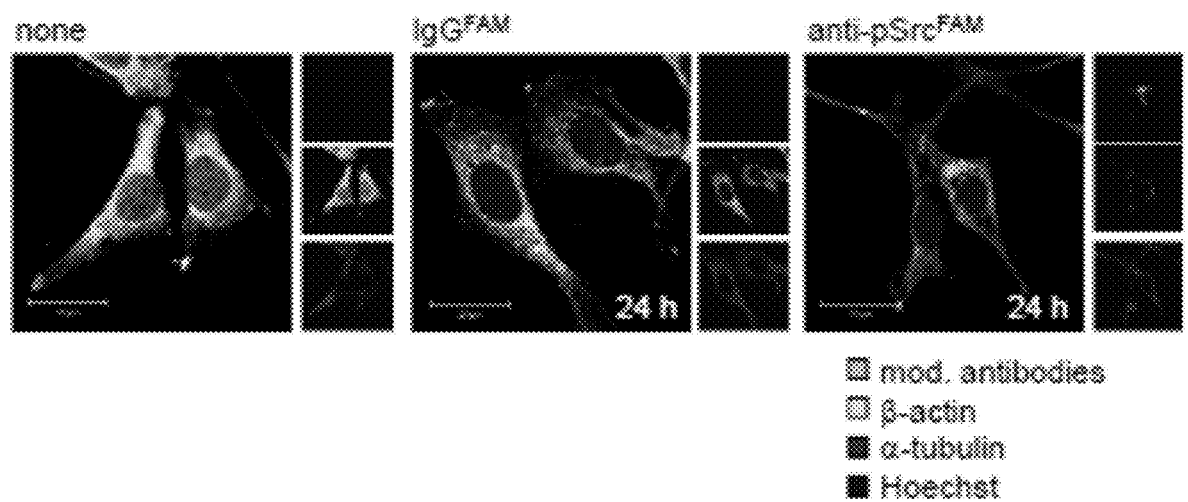
FIG. 29 are images showing mouse 3T3/vSrc cells were with modified antibodies as indicated at 10 μg/ml for 24 hours. Fixed cells were stained for β-tubulin and β-actin and analyzed by confocal microscopy. Emission for each channel shown separately on the right. Scale bar, 50 μm.

Potent antitumor effects by modified anti-phosphoSrc antibodies. The antitumor effects in vivo were next assessed for the various antibodies modified by phosphorothioated oligos. 3T3 cells transformed by v-Src were implanted into immune competent, syngeneic mice. Equal amounts of modified IgG or anti-p-Src antibodies (10 μg per mouse) were injected into tumors. While the growth curve of tumors was similar between those without any treatments and those treated with modified IgG antibodies, it was significantly slower for those tumors which received modified p-Src antibodies (FIG. 25A). Then prepared were homogenates from tumors received no treatment, or modified control or p-Src antibodies, followed by Western blotting analyses to assess the in vivo effects of the modified antibodies on its target and target downstream genes. The results from such analyses indicated that in vivo the modified p-Src antibodies could effectively inhibit phosphorylated Src and its downstream target, phosphorylated Stat3 (FIG. 25B, left panel), as well as other known p-Src downstream targets, FAK, β-actin and E-cadherin (FIG. 25B, right panel). A role of activated Src in cell actin filament structures is known. The modified p-Src antibodies could also inhibit tumor cell actin filament structures (FIG. 29), which play a role in cell migration and tumor invasion.

Figure 25C:
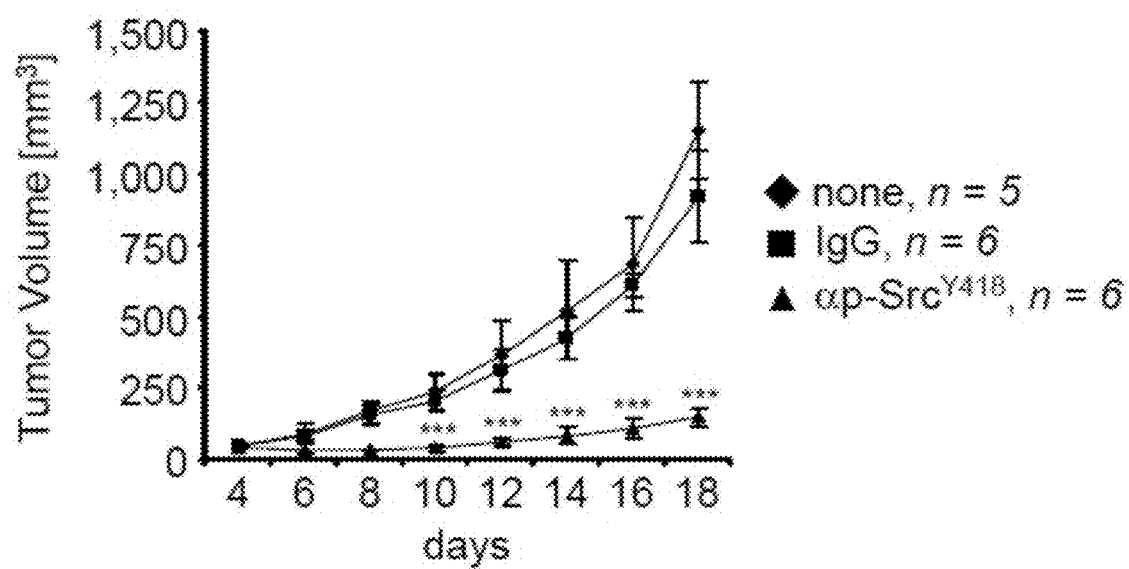
Figure 25D:
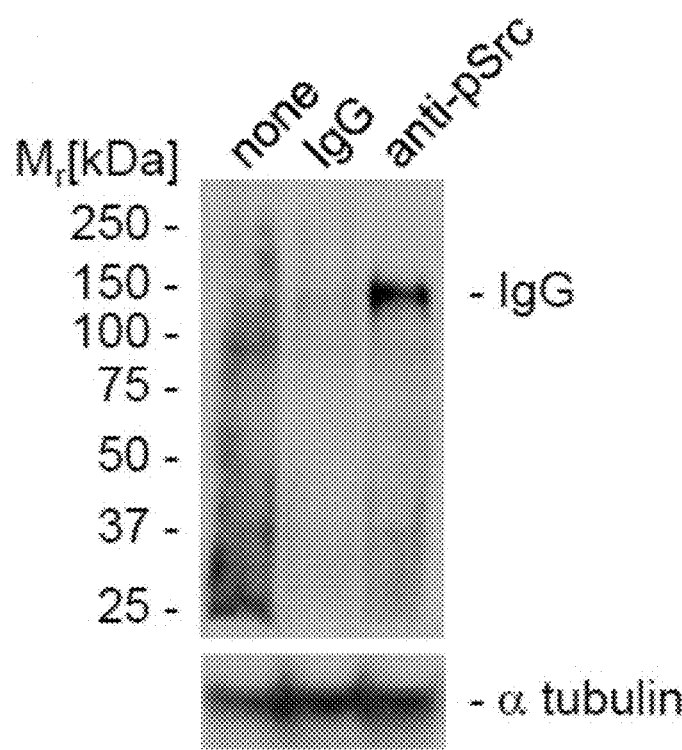
Figure 25E:
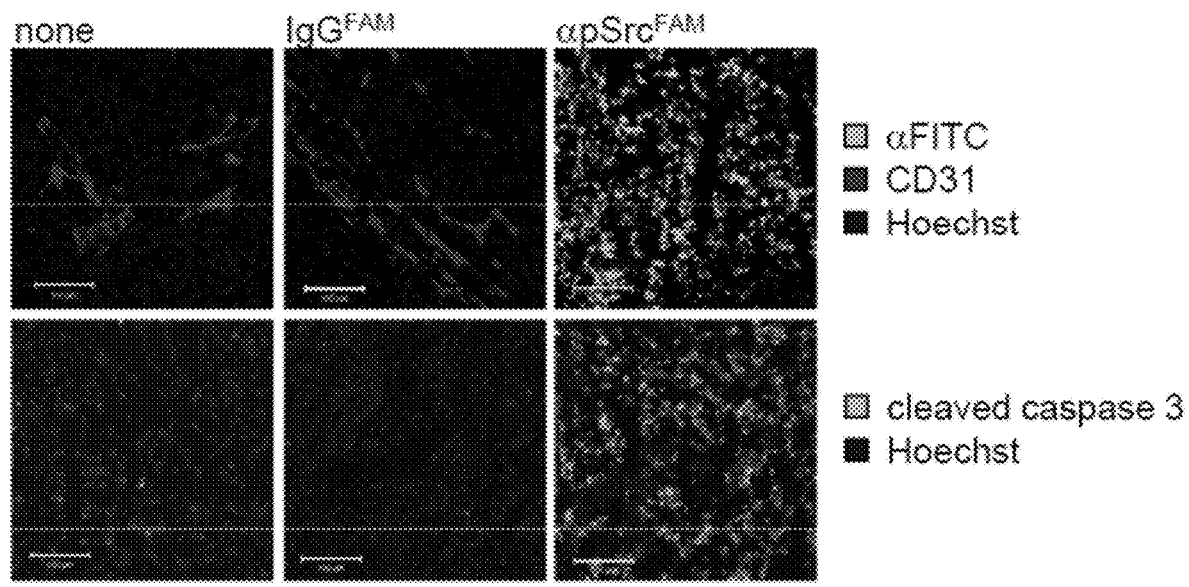
Figure 25F:
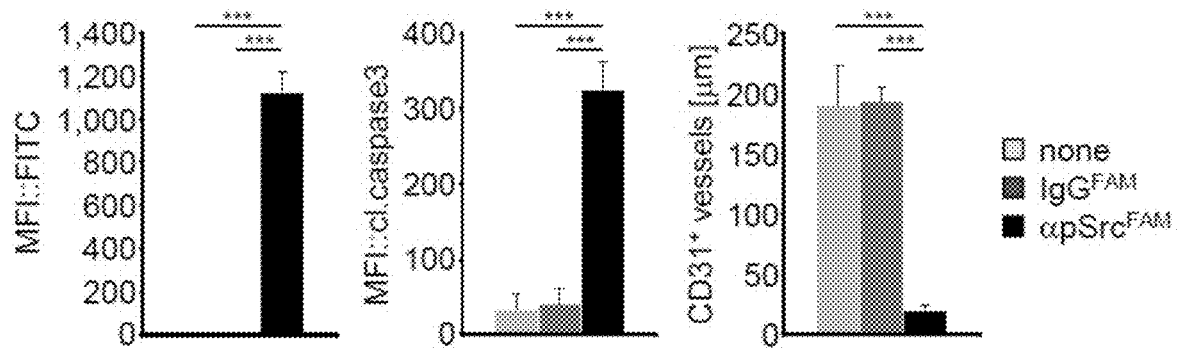

Since the survival and growth of human melanoma A2058 tumor cells are p-Src-dependent, the in vivo effects of the modified p-Src antibodies were further evaluated in A2058 xenograft tumor model. As seen in the 3T3 v-Src mouse tumor model, treating the human melanoma tumors with the modified p-Src antibodies significantly inhibited tumor growth in mice (FIG. 25C). Western blotting using homogenates prepared from the tumors from both control and testing groups showed that the modified p-Src antibodies, but not the modified IgG antibodies, which do not have target protein to bind, were retained in the tumors in vivo (FIG. 25D). Moreover, microscopic analyses of the tumor sections showed that only modified p-Src antibodies, but not modified IgG antibodies, were retained in tumors (FIG. 25E top panels). The retention of the target antibodies was associated with loss of tumor vasculature (FIG. 25E top panels), as well as an increase in tumor apoptosis (FIG. 25E lower panels). The differences in antibody tumor retention, tumor cell apoptosis and loss of tumor vasculature between control and target antibodies treated tumors were significant (FIG. 25F).

Figure 26A:
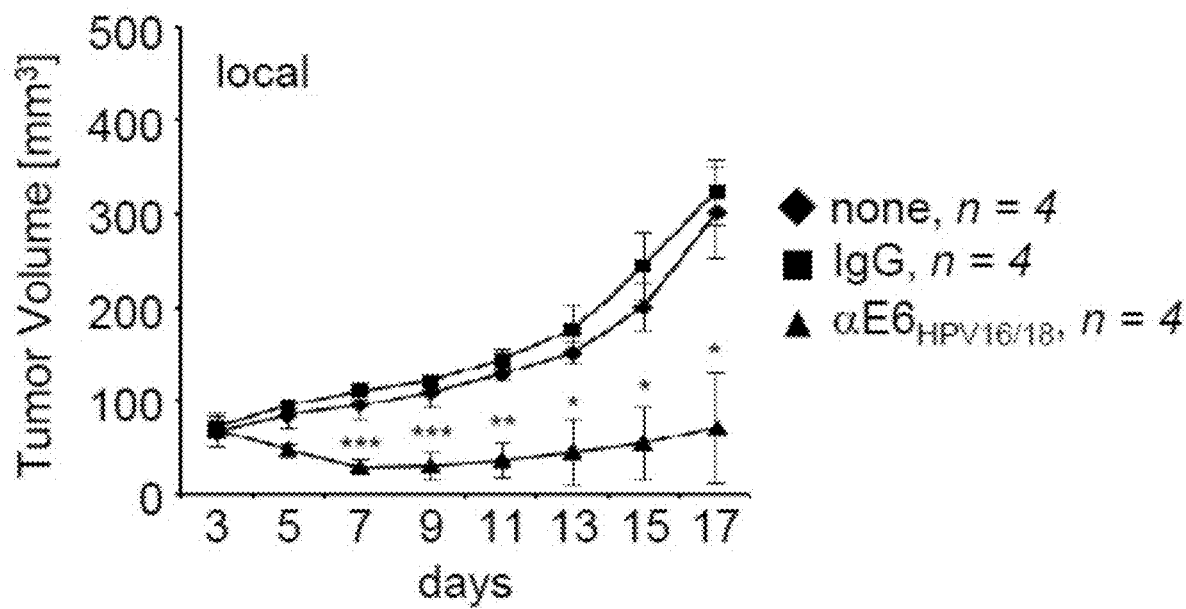
FIGS. 26A, 26B, 26C, 26D, 26E, 26F, and 26G, show antitumor efficacy of the modified antibodies targeting E6 oncoprotein in cervical cancer.
Figure 26B:
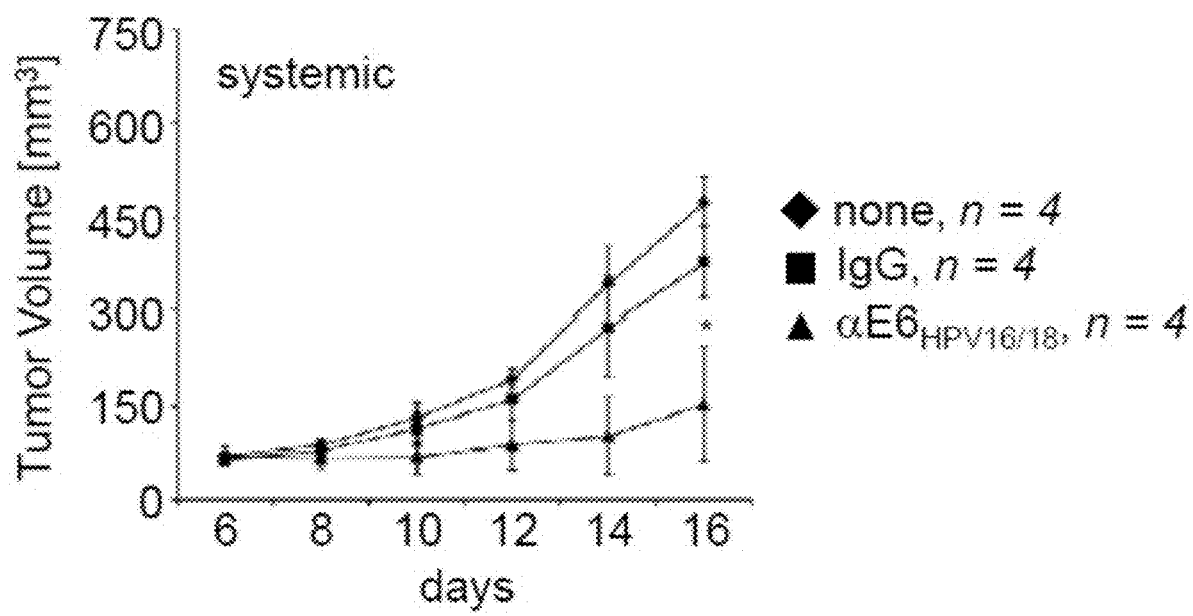
Figure 26C:
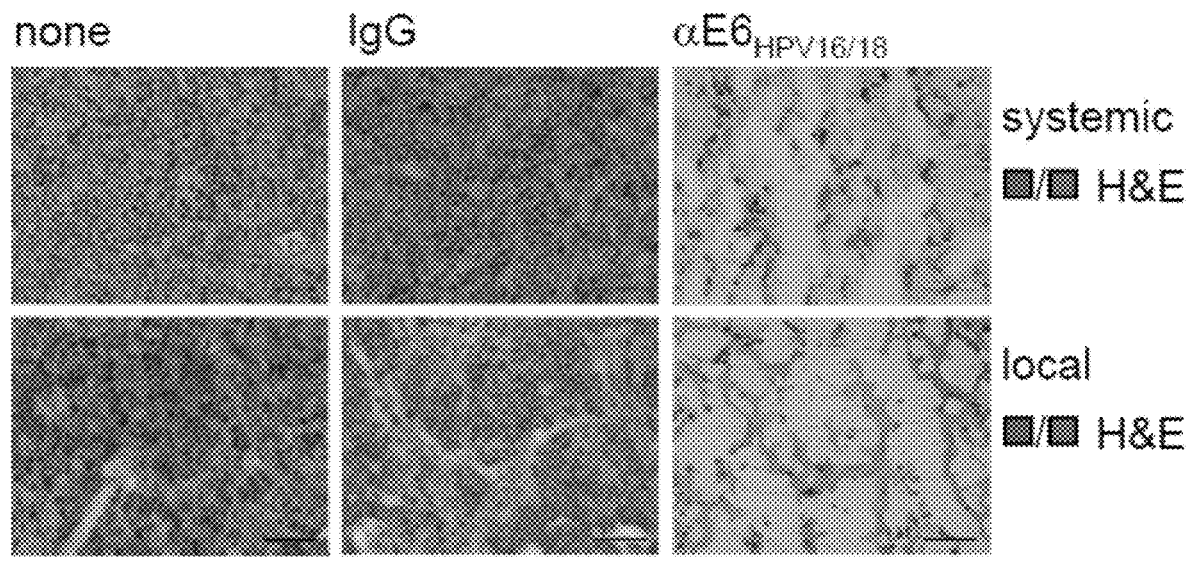
Figure 26D:
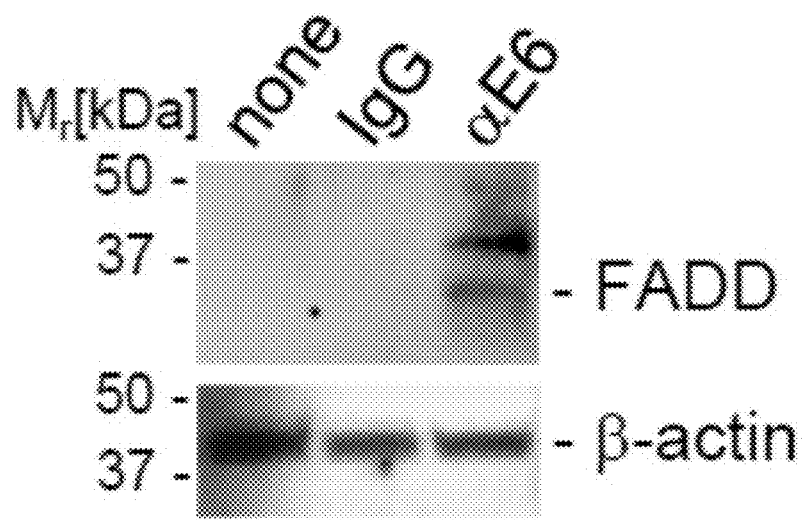
Figure 26E:
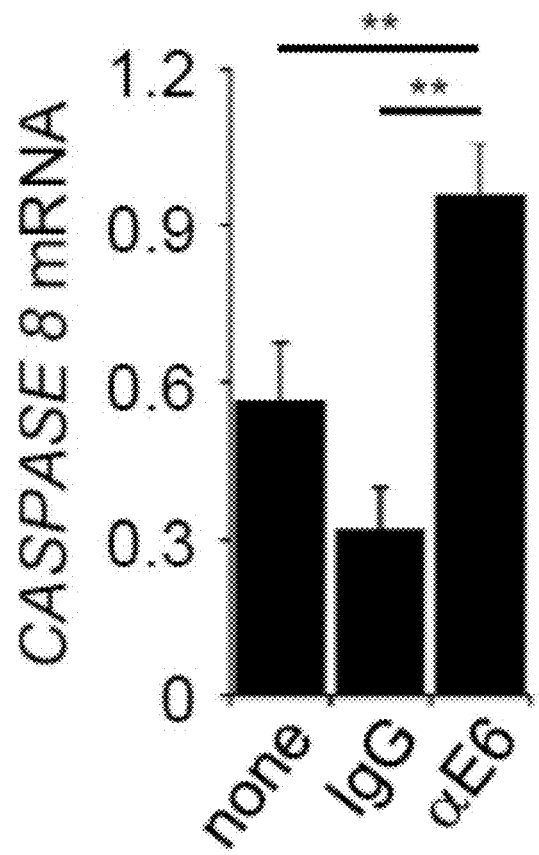
Figure 26F:
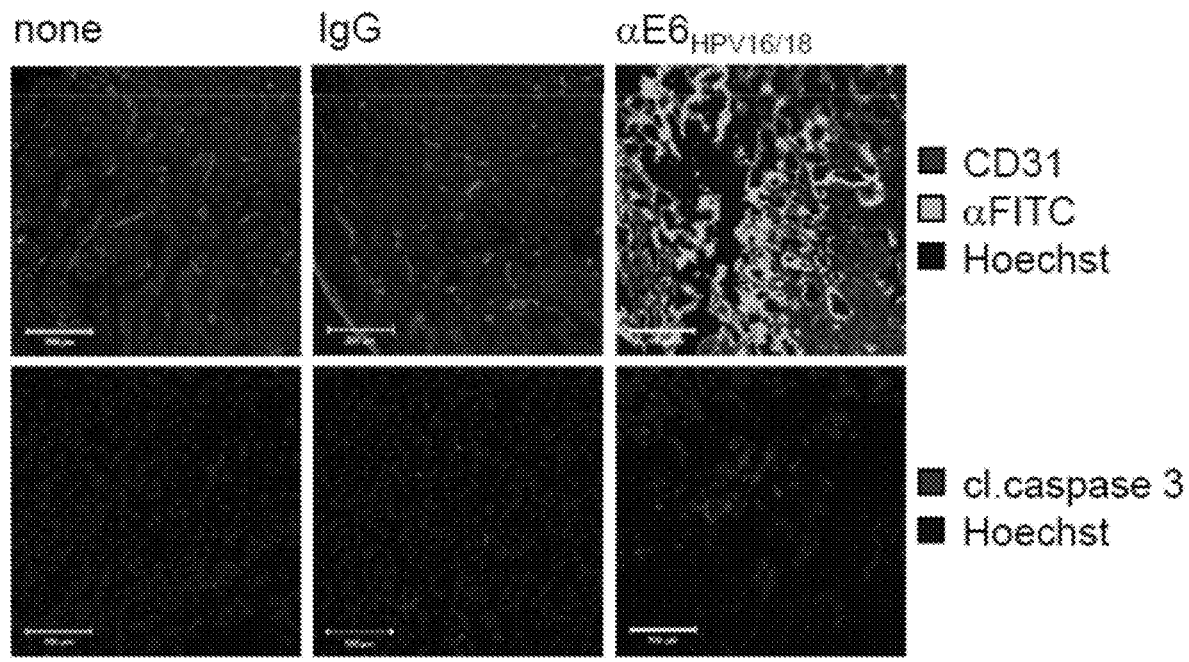
Figure 26G:
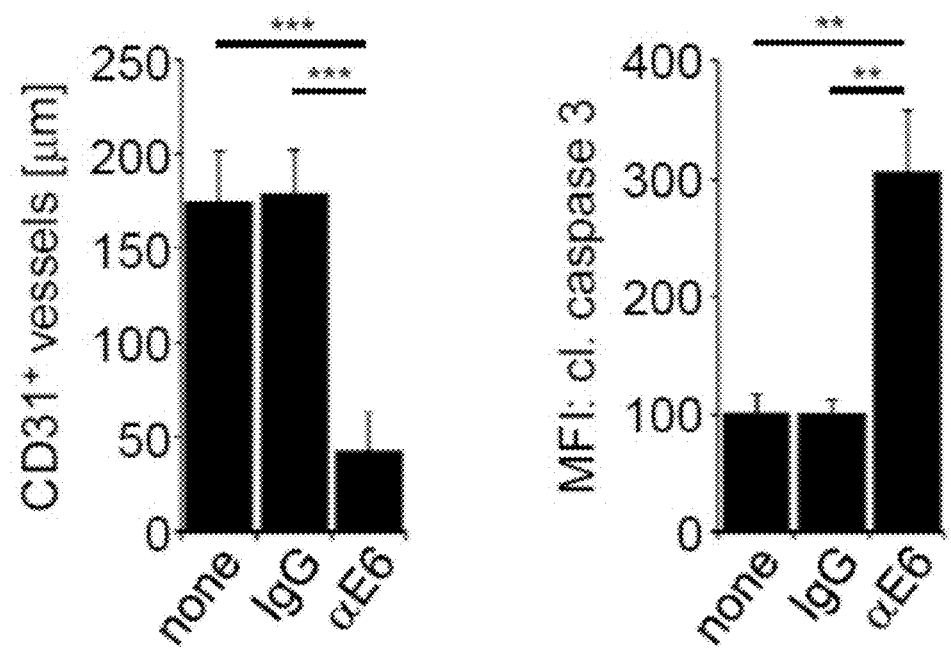

Modified anti-HPV E6 antibodies inhibit tumor growth. Several intracellular viral proteins are good targets for treating diseases such as cancer. HPV16/18 E6 and E7 proteins, for example, are well known oncoproteins crucial for transformation and malignancy of cells in majority cervical cancer and head and neck cancer. However, there are no effective drugs to block their oncogenic activities. Therefore, it was tested whether modifying a monoclonal antibody against HPV16/18 E6 would generate an effective inhibitor to block E6 function and tumor growth. Because E6 (E7 also) protein is very small, it was reasoned that an antibody could "engulf" the entire protein thereby blocking its function. Human CaSki cervical cancer cells were injected subcutaneously to form tumors in nude mice. When tumors reached approximately an average of 5 mm in diameter, equal amounts of modified IgG or anti-E6 antibodies (10 μg per mouse) were injected into tumors. While the tumors treated with the modified IgG antibodies grew similarly as the non-treated tumors, those injected with the modified E6 antibodies had significant growth retardation compared to the two control groups (FIG. 26A). The antitumor effects were also tested of systemically administered modified E6 monoclonal antibodies. The inhibitory effects were observed of systemically delivered modified E6 antibodies on the CaSki tumor growth (FIG. 26B). H&E staining indicated that both systemic and local treatments with the modified E6 antibodies had destructive effects on the tumor tissues (FIG. 26C). Western blotting analysis and real-time RT-PCR using the tumors from in vivo experiments (FIGS. 26A and 26B) showed upregulating expression of the FADD gene, which bridges members of the Fas-receptor to pro-caspases to form complexes for inducing cell death, as well as the caspase 8 gene (FIGS. 26D and 26E). Confocal microscopic analysis of the CaSki tumor sections (same tumors in FIG. 26A) indicated that only the modified E6 antibodies but not the modified IgG antibodies were readily detectable in the treated tumors (FIG. 26F, top panels). Treating tumors with the modified anti-E6 antibodies also resulted in destruction of tumor vasculature as indicated by the reduction of CD31-positively (FIG. 26F, top panels). Using the same tumor tissues it was further shown that cleaved caspase 3 protein level was elevated (FIG. 26F, lower panels).

Figure 27A:
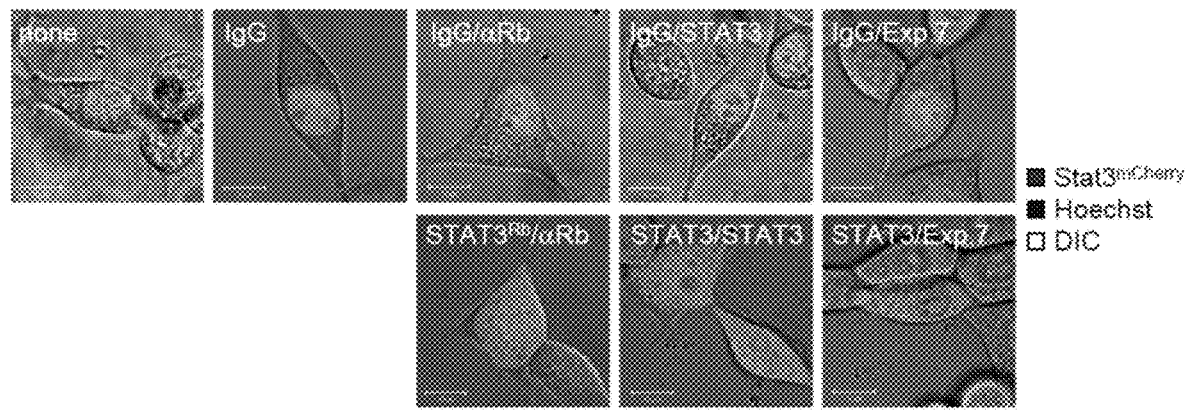
FIGS. 27A, 27B, 27C, 27D, 27E, 27F, and 27G show targeting STAT3 with modified antibodies.

Targeting STAT3 in vivo by cell-penetrating antibodies. STAT3 activity blocking by antibodies was assessed. However, unlike phosphorylated site of Src, which is exposed on Src tyrosine kinase molecule surface, the major tyrosine phosphorylated and acetylated sites of STAT3 are difficult to access due to their positions within the folded STAT3 molecule. Although activated STAT3 is largely confined in the nucleus, STAT3 shuttles to the cytoplasm to be reactivated. According to diffusion properties of spherical particles, an increase in molecular weight can unbalance compartmental accumulation of proteins. It was thus postulated that using two antibodies to recognize two discrete parts of a STAT3 or another interacting protein could form a large stable complex, thereby tipping the balance in favor of cytoplasmic compartmental accumulation of activated STAT3. Confocal microscopic analyses indicated that two modified STAT3 antibodies that recognizing discrete sites of STAT3 facilitated increased cytoplasmic accumulation of STAT3 protein in 3T3v-Src cells transiently transfected with STAT3-mCherry, which allowed a fraction of the cells with STAT3-mCherry in nucleus (FIG. 27A). Treating the same cells with rabbit anti-STAT3 antibodies and anti-rabbit antibodies also resulted in an increase in cytoplasmic accumulation of STAT3 protein (FIG. 27A). However, the most effective combination of dual antibodies to trap STAT3 protein in the cytoplasm was STAT3 and exportin 7 (FIG. 27A). Exportin 7 has been shown to be critical for STAT3 nucleocytoplasmic shuttling (Herrmann et al., *Cancer Res.* 70:7455-7464 (2010)).

Figure 27B:
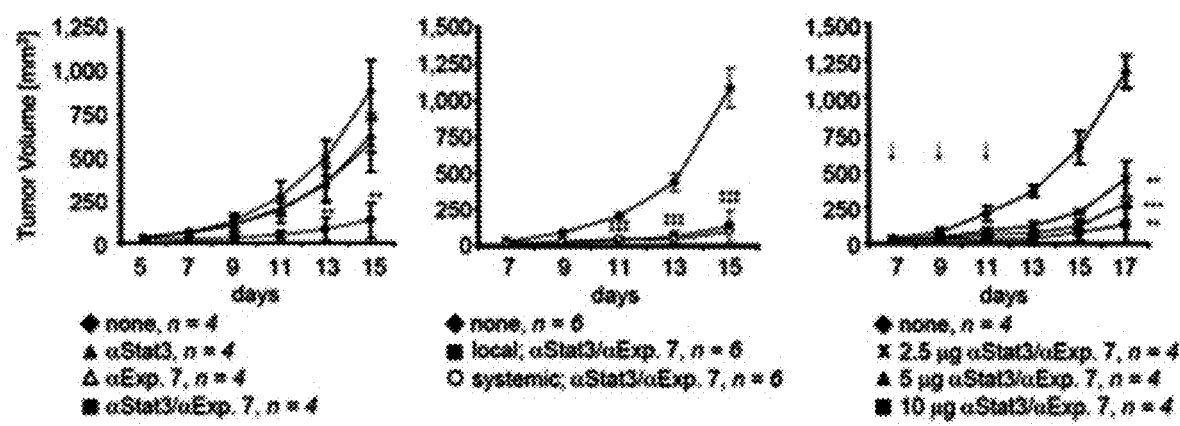
Figure 27C:
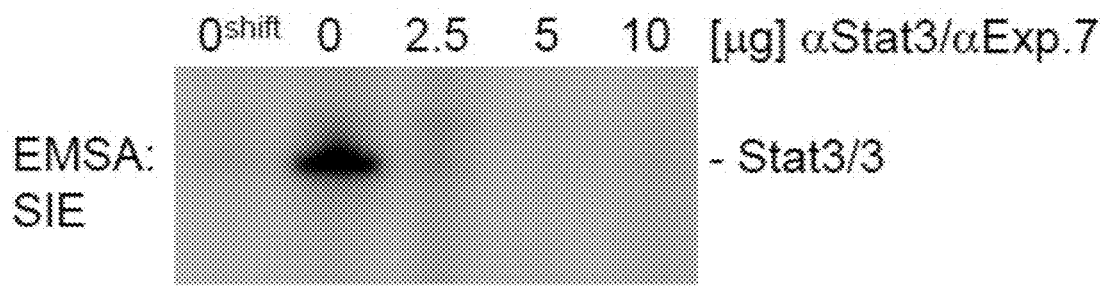
Figure 27D:
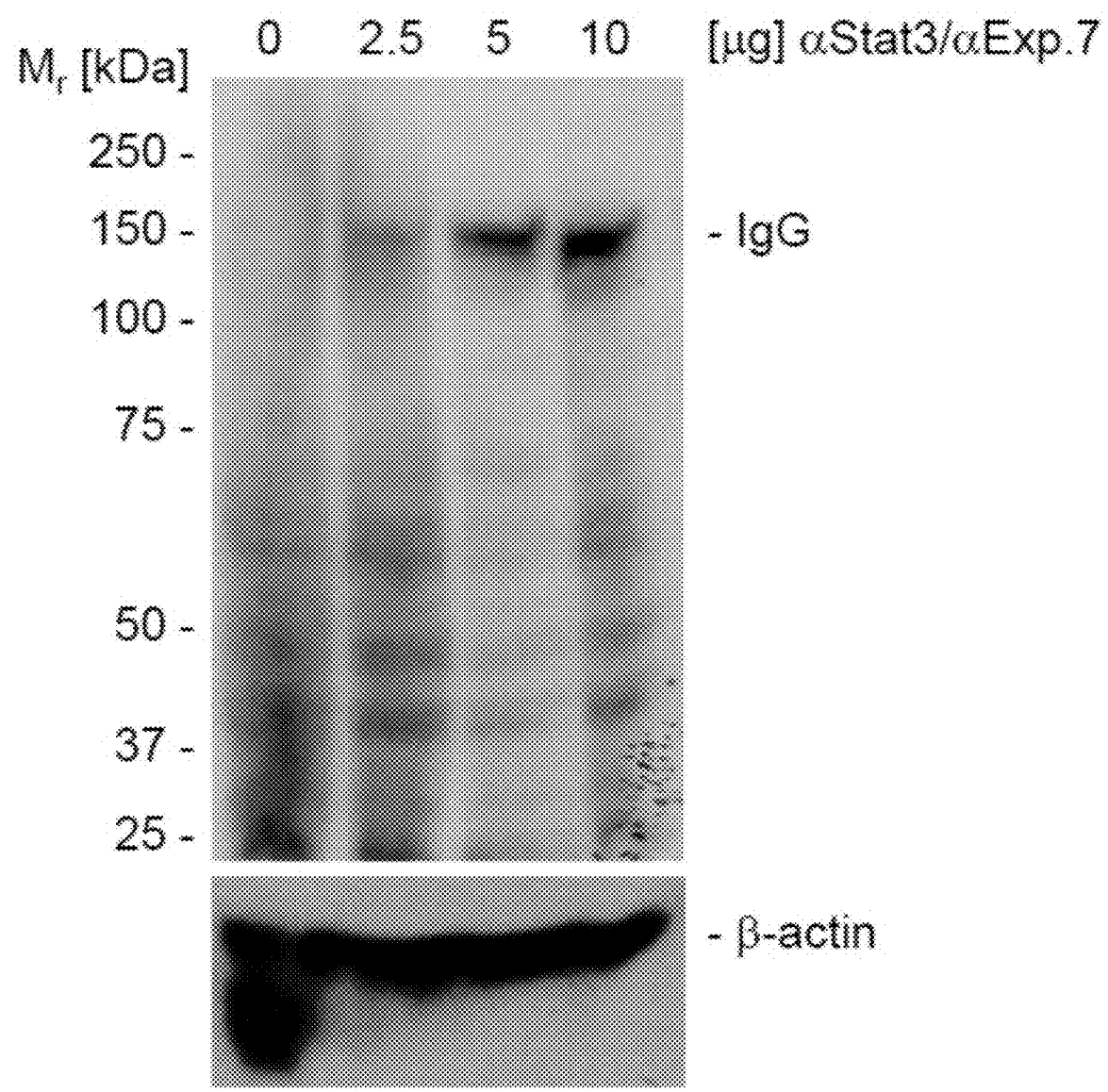

Because STAT3/exportin 7 dual antibody was the most effective in keeping STAT3 in the cytoplasm (FIG. 27A), and because it was found STAT3 and exportin 7 interaction requires STAT3685 acetylation, and acetylation of STAT3 is prevalent in tumors and tumorigenic, modified STAT3 and exportin 7 antibodies were used for in vivo tumor treatment. Indeed, treating established B16 mouse melanoma with both modified STAT3 and exportin 7 led to significant tumor growth retardation, while either modified antibody alone did not (FIG. 27B, left panel). Both local and systemic injections of modified STAT3/exportin 7 antibodies effectively inhibited B16 melanoma tumor growth (FIG. 27B, middle panel). It was further shown that systemic injections of the modified STAT3/exportin 7 antibodies, even at a low dose of 2.5 μg per treatment effectively inhibited tumor growth, and potent antitumor effects remained when systemic treatment was discontinued after only three treatments (FIG. 27B right panel). The systemic antibody treatment also inhibited tumor STAT3 activity as assessed by measuring STAT3-DNA binding (FIG. 27C). In addition, the systemically delivered modified STAT3/exportin 7 antibodies were retained in the tumors even 8 days after last treatment (FIG. 27D).

Figure 27E:
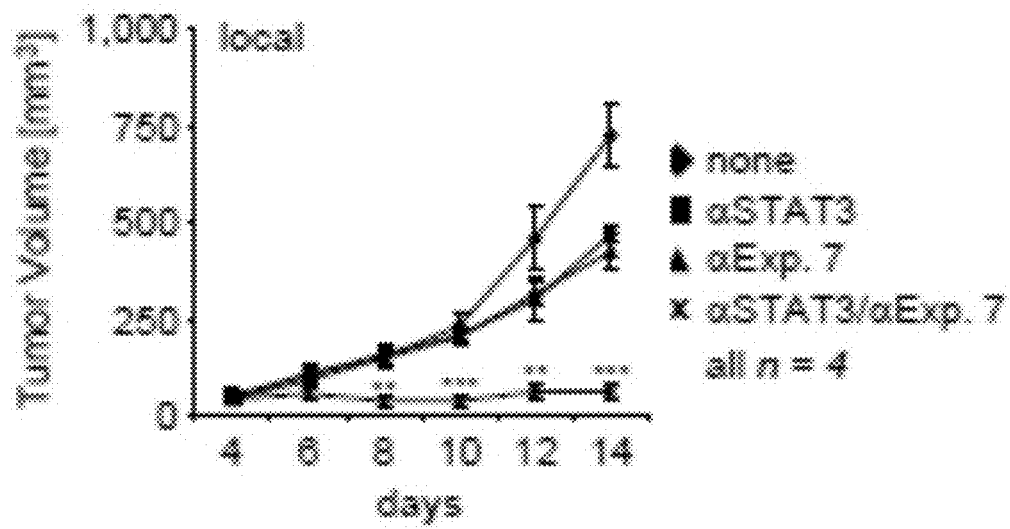
Figure 27F:
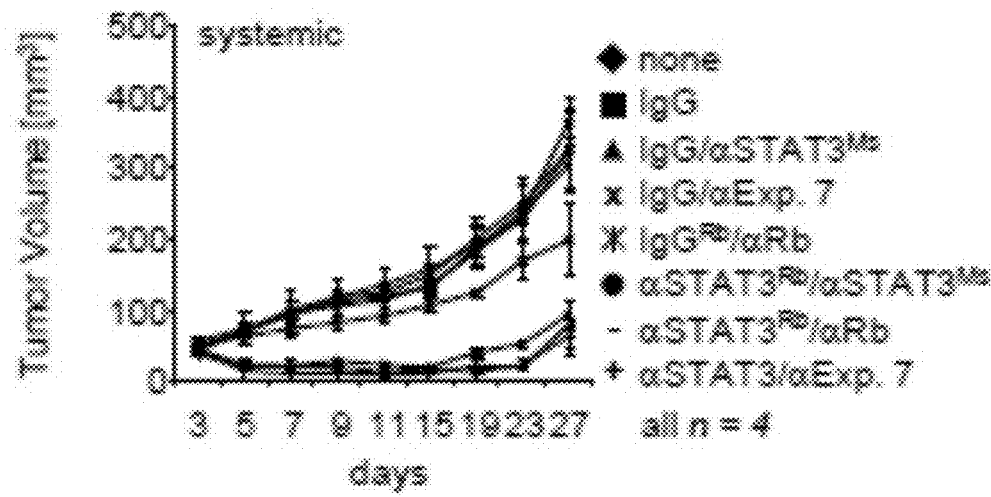
Figure 27G:
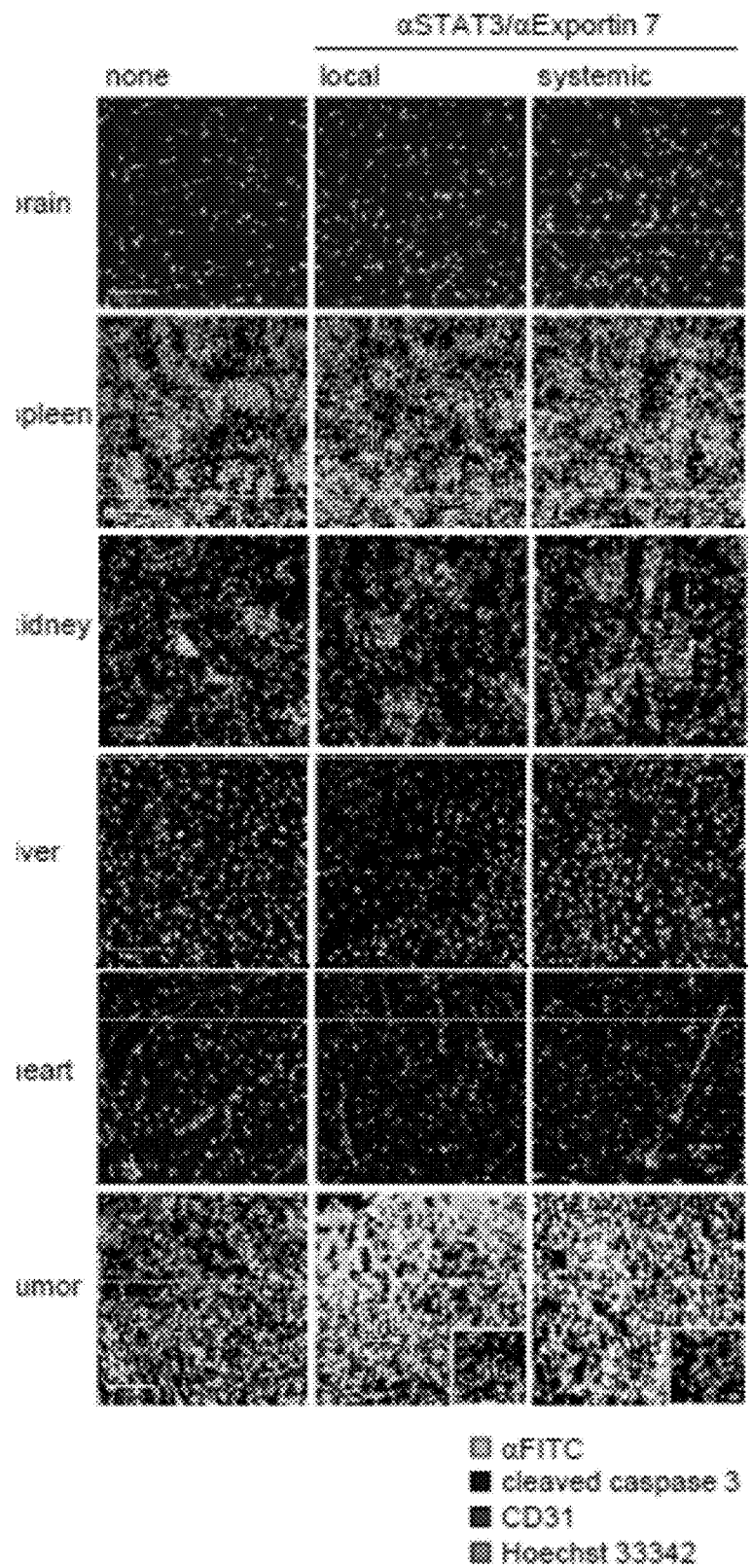
Figure 30A:
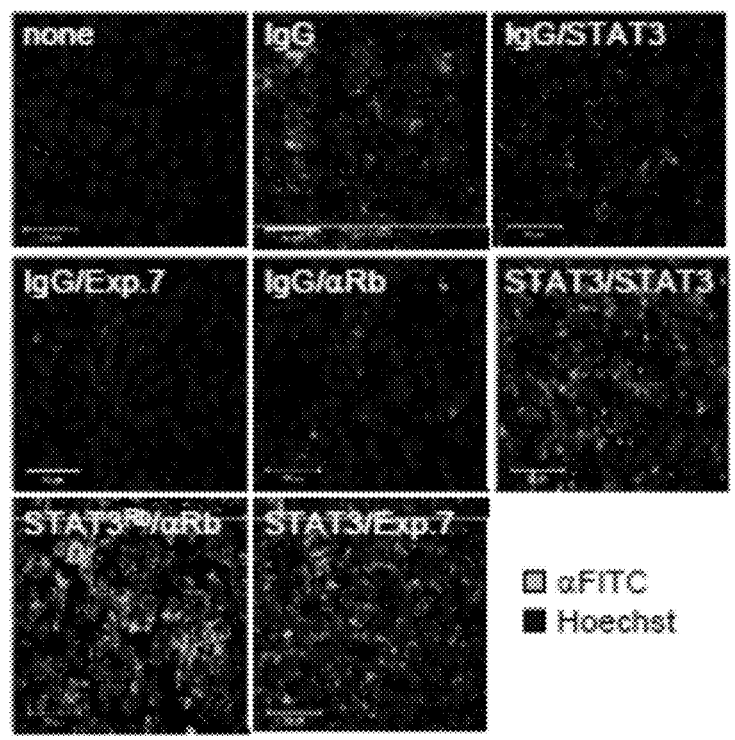
FIGS. 30A and 30B show human U87 glioma were treated systemically every other day. Tumor sections were stained for fluorescein. Stained sections were analyzed by confocal microscopy. Scale bar, 50 μm (FIG. 30A). Fluorescein emission signals were quantified. SD shown (FIG. 30B).
Figure 30B:
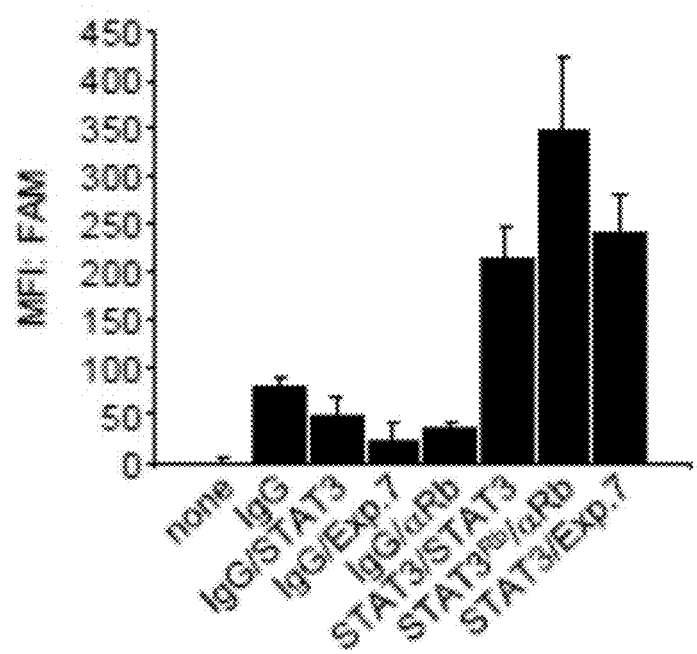
Figure 31A:
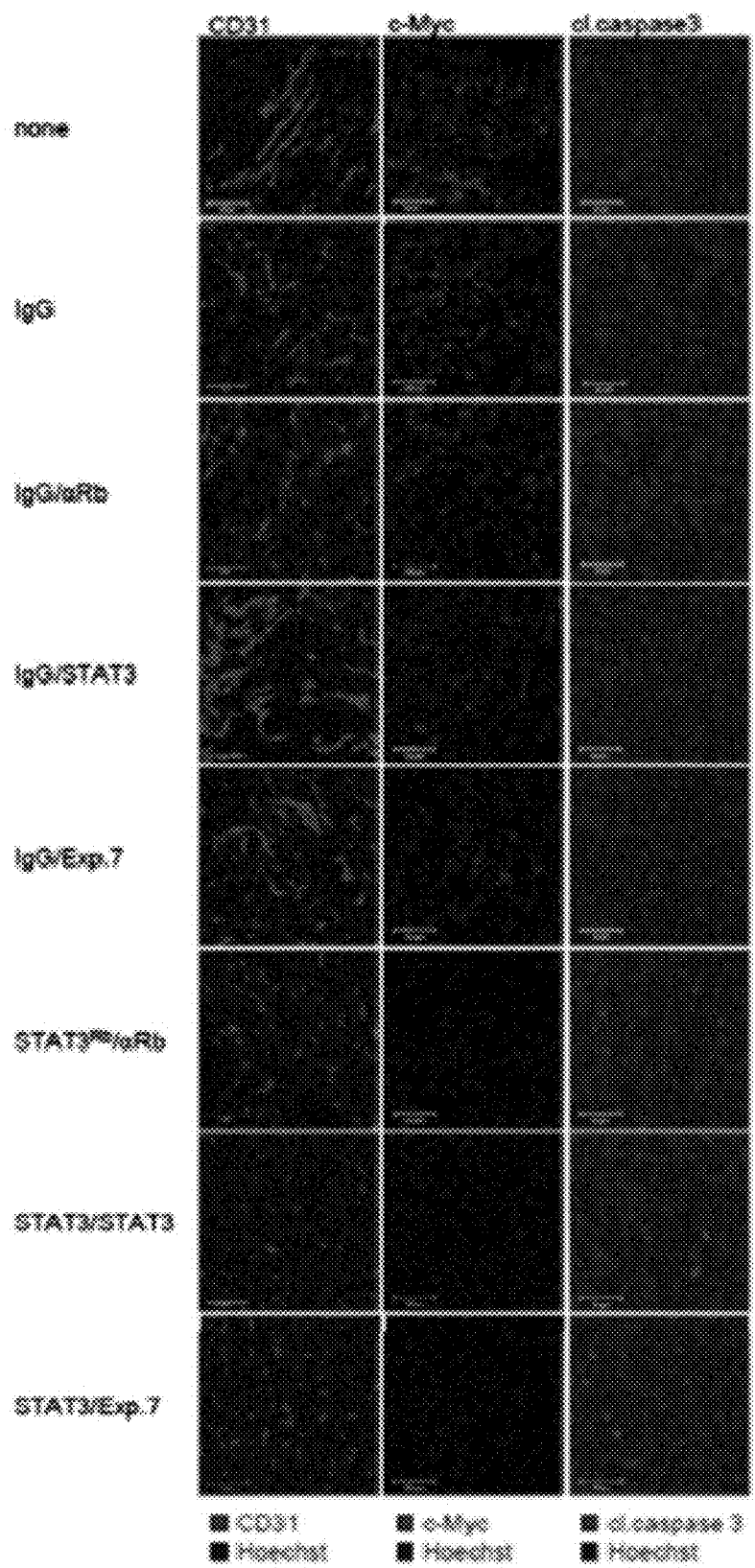
FIGS. 31A and 31B show human U87 glioma were treated systemically every other Tumor sections were stained for CD31+ tumor vasculature (left panels), c-Myc expression (middle panels), and tumor cell apoptosis indicated by cleaved caspase 3 (right panels). Stained sections were analyzed by confocal microscopy. Scale bar, 100 μm and 50 μm, respectively (FIG. 31A). Emission signals were quantified. SD shown; significance: *) P<0.05, ) P<0.01, *) P<0.001, (FIG. 31B).
Figure 31B:
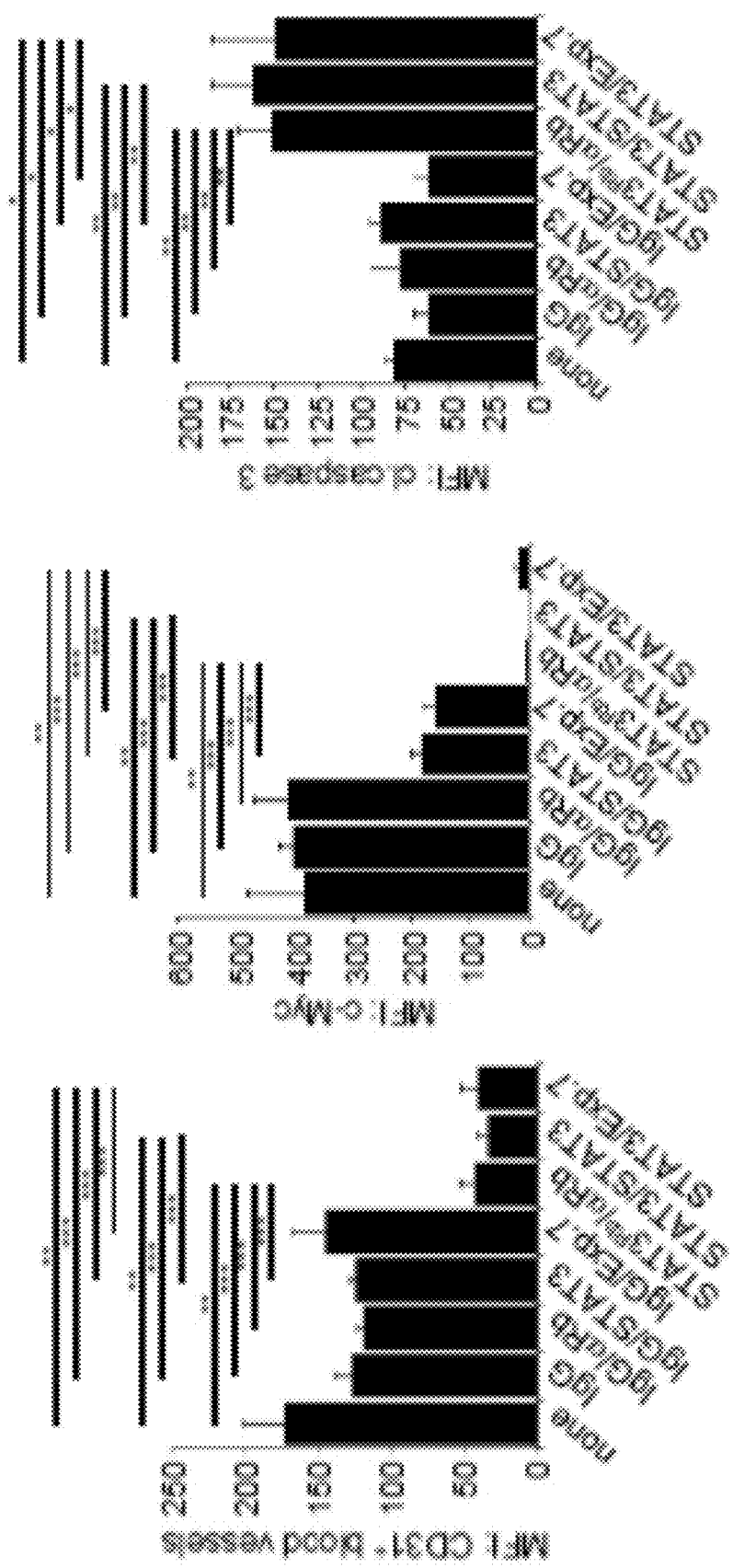

The antitumor efficacy was tested of the modified STAT3/exportin 7 antibodies in a human glioma xenograft model. Both local treatment and systemic administration of the modified STAT3/exportin 7 antibodies to mice bearing established human U87 glioma led to effective antitumor effects (FIG. 27E, upper panel). Moreover, the antitumor effects of systemically administrating two modified STAT3 antibodies that recognizing discrete sites of STAT3, and that of modified anti-STAT3 antibodies (rabbit) and anti-rabbit antibodies were assessed along with STAT3/exportin 7 and other control antibodies (FIG. 27E lower panel). The antitumor effects of this set of experiments were associated with detection of antibodies in tumors (FIG. 30A, 30B) and disruption of the tumor vasculature, inhibition of STAT3 downstream oncogenic gene c-Myc and an increase in apoptotic cleaved caspase 3 (FIG. 31A, 31B). To assess the tissue distribution of the modified antibodies in mice bearing human U251 glioma tumors, STAT3/exportin 7 antibodies were administered, both through local peritumoral and systemic injections. 24 hour post antibody injections, tissues from several organs in addition to tumors were prepared for confocal microscopic analyses to detect the presence of fluorescence-labeled antibodies as well as CD31 and cleaved caspase 3 to evaluate the effects of the antibodies on vasculature and tumor cell apoptosis. Data generated from this set of experiments indicated that at 24 hours post last injection (both local and systemic) the modified antibodies were most prominent in the tumor, destroying tumor vasculature and inducing apoptosis (FIG. 27F).

The studies demonstrate that modifying antibodies with phosphorothioated-oligos enable the antibodies to penetrate cell membranes. It also appears that binding to target protein facilitates intracellular retention of targeting antibodies, disallowing their leaving cells efficiently. Although the results presented here only show the effectiveness in intracellular delivery of antibodies, the technology platform should be applicable for enabling cell penetration of various proteins/enzymes.

The in vitro and in vivo results include the use of both polyclonal and monoclonal antibodies. While monoclonal antibodies are the only ones used in the clinic today and have the advantage of being pure, polyclonal antibodies could potentially have better efficacies due to their ability to recognize multiple epitopes of the antigen/target. Whether polyclonal antibodies are also suitable for clinical use awaits further considerations and warrants more investigations. Currently, two different approaches have been used to attach phosphorothioated oligos with antibodies. Nevertheless, the current studies have demonstrated the proof of principle that macromolecules such as antibodies can now be used to target intracellular molecules including those that are considered intractable.

Example 3

Phosphorothioated-Oligo Modified Antibodies Enter Cells and Recognize Intracellular Targets Nucleic acids can be attached to proteins such as antibodies in a variety of ways. To investigate the effects of attachment on activity, cells were incubated with antibodies attached to phosphorothioated nucleic acids via a vinyl sulfone reactive moiety or through a S—S-hexanol reactive moiety. The antibodies were prepared as outlined in the methods for Example 2. For the αSTAT3-VS-oligo P, this antibody was prepared by purifying by HPLC the antibodies reacted with the VS-oligo (αSTAT3-VS-oligo UP). P stands for purified and UP stands for unpurified.

Figure 32:
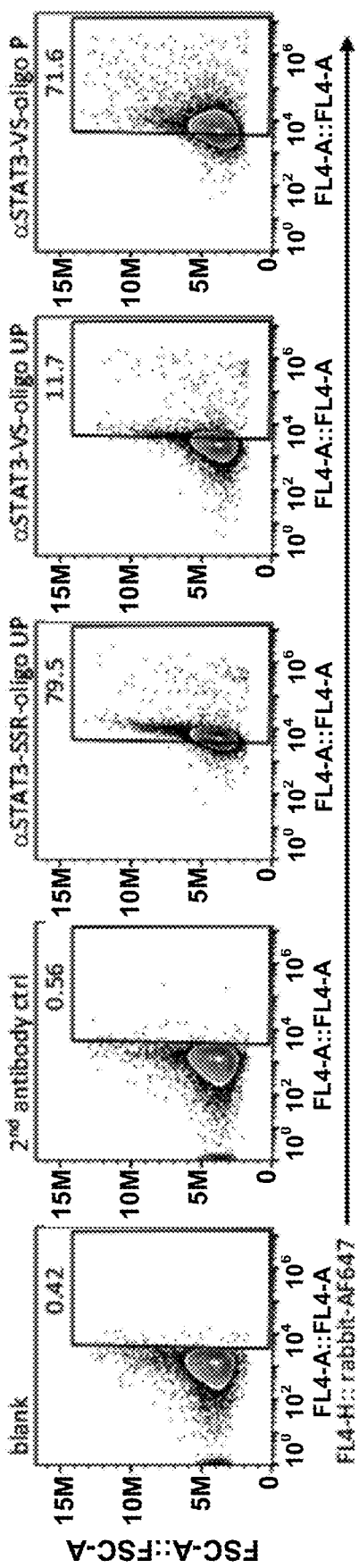
FIG. 32 are graphs of flow cell analyses of human Karpas299 lymphoma cells incubated for with 10 mg/ml of purified (P) or unpurified (UP) anti-STAT3 rabbit-antibody modified via vinylsulfone (VS) mediated attachment of phosphorothioated DNA-20meric-oligos or unpurified SSR-oligo-antibody conjugate/complex.

Human Karpas299 lymphoma cells were incubated for 2 hours with 10 µg/ml of purified (P) or unpurified (UP) aSTAT3 rabbit-antibody modified via vinylsulfone (VS) mediated attachment of phosphorothioated DNA-20meric-oligos or unpurified SSR-oligo-antibody conjugate/complex. After cells were fixed and permeabilized, rabbit IgG species were stained intracellularly and cells were analzyed for rabbit IgG contents via flow cytomtry as indicated by gating. The results are shown in FIG. 32. Specifically, the results show that antibodies attached to phosphorothioated nucleic acids through different chemical means can achieve intracellular delivery.

To confirm delivery and recognition, human U251 glioma cells were incubated for 2 hrs with 10 µg/ml of purified (P) aSTAT3 antibody either modified via vinylsulfone (VS) mediated attachment of phosphorothioated DNA-20meric-oligos (lane 1) or unmodified aSTAT3 alone (lane 3) or aSTAT3 and 500 pmol/ml phosphorothioated GpC1668, same as attached via VS (lane 4; lane 2 empty). After preparing whole cell lysates cleared from cell debris, protein G coupled agarose beads were added and incubated at 4° C. overnight before Western blot procedure. The results are shown in FIG. 33A.

Human U251 cells were incubated for 2 hrs with 10 µg/ml of unpurified (UP) aSTAT3 antibody modified via SSR (lane 2), unpurified (UP) aSTAT3 antibody modified via vinylsulfone (VS) mediated attachment of phosphorothioated oligos (lane 3) or purified (P) aSTAT3 antibody modified via vinylsulfone (VS) mediated attachment of phosphorothioated (lane 4); no antibody IgG added (lane 1). After preparing whole cell lysates cleared from cell debris, protein G coupled agarose beads were added and incubated at 4° C. overnight before Western blot procedure. The results are shown in FIG. 33B.

Figure 33A:
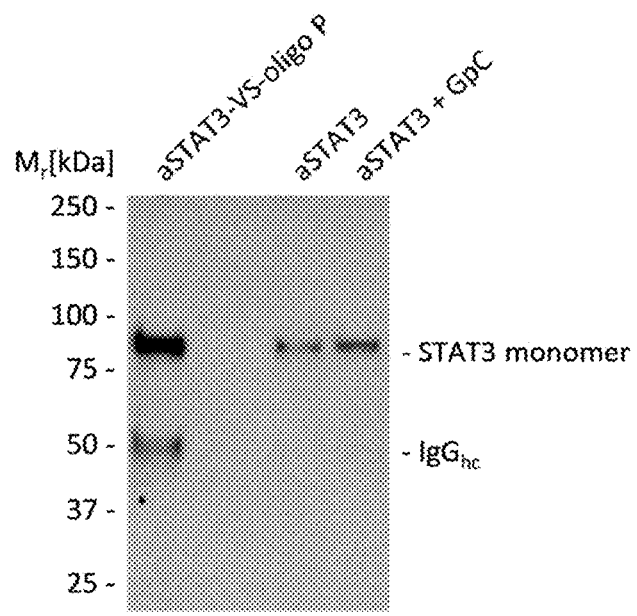
FIGS. 33A and 33B are images of Western blots showing phosphorothioated-oligo modified antibodies enter cells and recognize intracellular targets such as STAT3.
Figure 33B:
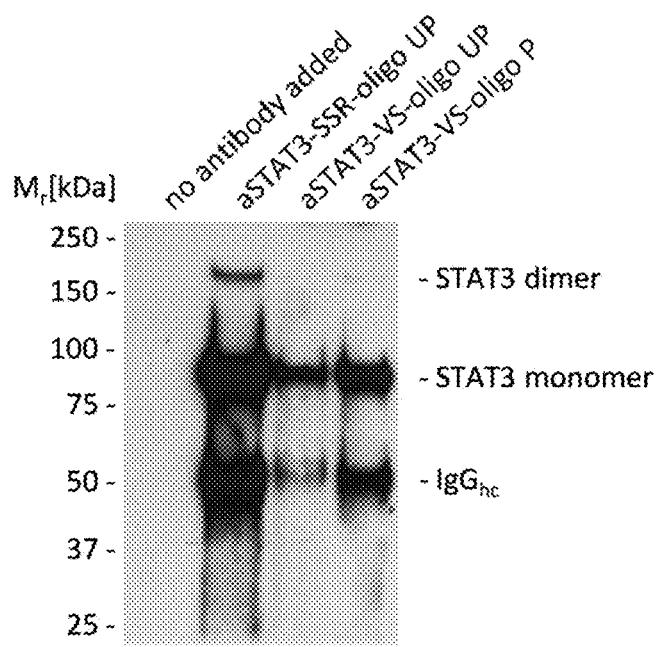

FIGS. 33A and 33B shows that a population of antibodies with phosphorothioated nucleic acids attached via a vinyl sulfone reactive moiety can enter cells and recognize intracellular targets. Further, the figures show that a population of antibodies with phsophorothioated nucleic acids attached via a different chemical attachment, e.g., through a S—S-hexanol also results in intracellular delivery and target recognition.

EMBODIMENTS

Embodiment P1

A cell penetrating conjugate comprising a non-cell penetrating protein attached to a phosphorothioate nucleic acid, wherein the phosphorothioate nucleic acid enhances intracellular delivery of the non-cell penetrating protein.

Embodiment P2

The cell penetrating conjugate of embodiment 1, wherein a plurality of phosphorothioate nucleic acids are attached to the non-cell penetrating protein.

Embodiment P3

The cell penetrating conjugate of embodiment 2, wherein 1, 2, 3, 4, 5, 6, 7, 8, 9, 10, 15, 20, 25, or more phosphorothioate nucleic acids are attached to the protein.

Embodiment P4

The cell penetrating conjugate of any one of embodiments 1 to 3, wherein each phosphorothioate nucleic acid is independently attached to a lysine, arginine, cysteine, or histidine of the non-cell penetrating protein.

Embodiment P5

The cell penetrating conjugate of embodiment 4, wherein each phosphorothioate nucleic acid is attached to a lysine of the protein.

Embodiment P6

The cell penetrating conjugate of embodiment 4, wherein the protein comprises phosphorothioate nucleic acids attached to 10%, 25%, 50%, 75%, 90%, 95%, or 100% of the lysines, arginines, cysteines, histidines, or combinations thereof of the protein.

Embodiment P7

The cell penetrating conjugate of any one of embodiments 1 to 6, wherein each phosphorothioate nucleic acid is independently 10, 20, 30, 40, 50, 60, 70, 80, 90, 100 or more nucleic acid residues in length.

Embodiment P8

The cell penetrating conjugate of embodiment 7, wherein each phosphorothioate nucleic acid is independently from 10 to 30 residues in length.

Embodiment P9

The cell penetrating conjugate of any one of embodiments 1 to 8, wherein each phosphorothioate nucleic acid is covalently attached to the protein.

Embodiment P10

The cell penetrating conjugate of any one of embodiments 1 to 9, wherein each phosphorothioate nucleic acid comprises a nonspecific sequence.

Embodiment P11

The cell penetrating conjugate of any one of embodiments 1 to 10, wherein the non-cell penetrating protein is a high molecular weight protein.

Embodiment P12

The cell penetrating conjugate of any one of embodiments 1 to 10, wherein the non-cell penetrating protein has a molecular weight of greater than 25 kD.

Embodiment P13

The cell penetrating conjugate of any one of embodiments 1 to 10, wherein the non-cell penetrating protein has a molecular weight of 25 to 750 kD.

Embodiment P14

The cell penetrating conjugate of any one of embodiments 1 to 13, wherein the non-cell penetrating protein is an antibody.

Embodiment P15

The cell penetrating conjugate of embodiment 14, wherein the antibody is an IgG antibody.

Embodiment P16

The cell penetrating conjugate of embodiment 14, wherein the antibody is an IgA, IgM, IgD or IgE antibody.

Embodiment P17

The cell penetrating conjugate of embodiment 14, wherein the antibody is an Fv fragment.

Embodiment P18

The cell penetrating conjugate of any one of embodiments 14 to 17, wherein the antibody is a humanized antibody.

Embodiment P19

The cell penetrating conjugate of any one of embodiments 1 to 18, wherein the non-cell penetrating protein binds an intracellular target.

Embodiment P20

The cell penetrating conjugate of embodiment 19, wherein the intracellular target is a target of a disease selected from the group consisting of autoimmune disease, inflammatory disease, metabolic disorder, developmental disorder, cardiovascular disease, liver disease, intestinal disease, infectious disease, endocrine disease, neurological disorder, and cancer.

Embodiment P21

The cell penetrating conjugate of embodiment 19 or 20, wherein the intracellular target is a signaling molecule or transcription factor.

Embodiment P22

The cell penetrating conjugate of embodiment 21, wherein the signaling molecule is a phosphatase or kinase.

Embodiment P23

The cell penetrating conjugate of embodiment 20, wherein the intracellular target is a cancer target.

Embodiment P24

The cell penetrating conjugate of embodiment 19, wherein the intracellular target is STAT3.

Embodiment P25

The cell penetrating conjugate of embodiment 19, wherein the intracellular target is exportin 7.

Embodiment P26

The cell penetrating conjugate of any one of embodiments 1 to 25, wherein the non-cell penetrating protein further comprises a label, a small molecule or a functional nucleic acid attached to the protein.

Embodiment P27

The cell penetrating conjugate of any one of embodiments 1 to 26 bound to an intracellular target.

Embodiment P28

A cell comprising the cell penetrating conjugate of any one of embodiments 1 to 26.

Embodiment P29

A pharmaceutical composition comprising the cell penetrating conjugate of any one of embodiments 1 to 26 and a pharmaceutically acceptable carrier.

Embodiment P30

The composition of embodiment 29, further comprising a second non-cell penetrating protein attached to one or more phosphorothioate nucleic acids.

Embodiment P31

The composition of embodiment 30, wherein the second non-cell penetrating protein binds an intracellular target.

Embodiment P32

The composition of embodiment 31, wherein the second non-cell penetrating protein binds a different epitope on the intracellular target relative to the non-cell penetrating protein of any one of embodiments 19 to 25.

Embodiment P33

The composition of embodiment 31, wherein the second non-cell penetrating protein binds a second intracellular target.

Embodiment P34

The composition of any one of embodiments 30 to 33, wherein the second non-cell penetrating protein is an antibody.

Embodiment P35

A kit comprising the cell penetrating conjugate of any one of embodiments 1 to 26 or the pharmaceutical composition of embodiment 29 and instructions for use.

Embodiment P36

The kit of embodiment 35, further comprising a second non-cell penetrating protein attached to one or more phosphorothioate nucleic acids.

Embodiment P37

The kit of embodiment 36, wherein the conjugate of any one of embodiments 1 to 26 and the second non-cell penetrating protein are in separate containers.

Embodiment P38

The kit of embodiment 36, wherein the pharmaceutical composition of embodiment 29 and the second non-cell penetrating protein are in separate containers.

Embodiment P39

The kit of any one of embodiments 36 to 38, wherein the second non-cell penetrating protein binds a different epitope on the intracellular target relative to the non-cell penetrating protein of any one of embodiments 19 to 25.

Embodiment P40

The kit of any one of embodiments 36 to 38, wherein the second non-cell penetrating protein binds a second intracellular target.

Embodiment P41

The kit of any one of embodiments 36 to 40, wherein the second non-cell penetrating protein is formulated as a pharmaceutical composition comprising the second non-cell penetrating protein and a pharmaceutically acceptable carrier.

Embodiment P42

The kit of any one of embodiments 35 to 41, wherein the second non-cell penetrating protein is an antibody.

Embodiment P43

A method of delivering a non-cell penetrating protein into a cell comprising contacting the cell with the cell penetrating conjugate of any one of embodiments 1 to 26.

Embodiment P44

The method of embodiment 43, wherein the non-cell penetrating protein binds the nuclear protein in the cytoplasm thereby forming a non-cell penetrating protein-nuclear protein complex.

Embodiment P45

The method of embodiment 44, wherein the non-cell penetrating protein-nuclear protein complex in not capable of entering the nucleus of the cell.

Embodiment P46

A method of treating a disease in a subject comprising administering to the subject an effective amount of the cell penetrating conjugate of any one of embodiments 1 to 26 wherein administration of the conjugate treats the disease in the subject.

Embodiment P47

The method of embodiment 46, further comprising administering to the subject a second non-cell penetrating protein attached to one or more phosphorothioate nucleic acids.

Embodiment P48

The method of embodiment 47, wherein the second non-cell penetrating protein binds a different epitope on the intracellular target relative to the conjugate of any one of embodiments 19 to 26.

Embodiment P49

The method of embodiment 47, wherein the second non-cell penetrating protein binds a second intracellular target.

Embodiment P50

The method of any one of embodiments 47 to 49, wherein the conjugate of any one of embodiments 1 to 26 and the second non-cell penetrating protein are administered simultaneously.

Embodiment P51

The method of any one of embodiments 47 to 49, wherein the conjugate of any one of embodiments 1 to 26 and the second non-cell penetrating protein are administered sequentially.

Embodiment P52

The method of any one of embodiments 47 to 51, wherein the second non-cell penetrating protein is an antibody.

Embodiment P53

The method of any one of embodiments 46 to 52, further comprising administering a second therapeutic agent to the subject.

Embodiment P54

The method of any one of embodiments 46 to 53, wherein the disease is selected from the group consisting of autoimmune disease, developmental disorder, inflammatory disease, metabolic disorder, cardiovascular disease, liver disease, intestinal disease, infectious disease, endocrine disease, neurological disorder, and cancer.

Embodiment P55

The method of embodiment 54, wherein the disease is cancer.

Embodiment P56

The method of embodiment 55, wherein the non-cell penetrating protein of the conjugate binds an intracellular target and the intracellular target is STAT3.

Embodiment P57

The method of embodiment 55, wherein the non-cell penetrating protein of the conjugate binds an intracellular target and the intracellular target is exportin 7.

Embodiment P58

The method of embodiment 52, wherein the non-cell penetrating protein of the conjugate is an antibody that specifically binds STAT3 and the second non-cell penetrating protein is an antibody that specifically binds exportin 7.

Embodiment P59

The method of embodiment 52, wherein the non-cell penetrating protein of the conjugate is an antibody that specifically binds STAT3 and the second non-cell penetrating protein is an antibody that specifically binds another epitope of STAT3.

Embodiment P2 1

A cell penetrating conjugate comprising a non-cell penetrating protein attached to a phosphorothioate nucleic acid, wherein the phosphorothioate nucleic acid enhances intracellular delivery of the non-cell penetrating protein.

Embodiment P2 2

The cell penetrating conjugate of embodiment 1, wherein a plurality of phosphorothioate nucleic acids are attached to the non-cell penetrating protein.

Embodiment P2 3

The cell penetrating conjugate of embodiment 2, wherein 1, 2, 3, 4, 5, 6, 7, 8, 9, 10, 15, 20, 25, or more phosphorothioate nucleic acids are attached to the protein.

Embodiment P2 4

The cell penetrating conjugate of any one of embodiments 1 to 3, wherein each phosphorothioate nucleic acid is independently attached to a lysine, arginine, cysteine, or histidine of the non-cell penetrating protein.

Embodiment P2 5

The cell penetrating conjugate of embodiment 4, wherein each phosphorothioate nucleic acid is attached to a lysine of the protein.

Embodiment P2 6

The cell penetrating conjugate of embodiment 4, wherein the protein comprises phosphorothioate nucleic acids attached to 10%, 25%, 50%, 75%, 90%, 95%, or 100% of the lysines, arginines, cysteines, histidines, or combinations thereof of the protein.

Embodiment P2 7

The cell penetrating conjugate of any one of embodiments 1 to 6, wherein each phosphorothioate nucleic acid is independently 10, 20, 30, 40, 50, 60, 70, 80, 90, 100 or more nucleic acid residues in length.

Embodiment P2 8

The cell penetrating conjugate of embodiment 7, wherein each phosphorothioate nucleic acid is independently from 10 to 30 residues in length.

Embodiment P2 9

The cell penetrating conjugate of any one of embodiments 1 to 8, wherein each phosphorothioate nucleic acid is covalently attached to the protein.

Embodiment P2 10

The cell penetrating conjugate of any one of embodiments 1 to 9, wherein each phosphorothioate nucleic acid comprises a nonspecific sequence.

Embodiment P2 11

The cell penetrating conjugate of any one of embodiments 1 to 10, wherein the non-cell penetrating protein is a high molecular weight protein.

Embodiment P2 12

The cell penetrating conjugate of any one of embodiments 1 to 10, wherein the non-cell penetrating protein has a molecular weight of greater than 25 kD.

Embodiment P2 13

The cell penetrating conjugate of any one of embodiments 1 to 10, wherein the non-cell penetrating protein has a molecular weight of 25 to 750 kD.

Embodiment P2 14

The cell penetrating conjugate of any one of embodiments 1 to 13, wherein the non-cell penetrating protein is an antibody.

Embodiment P2 15

The cell penetrating conjugate of embodiment 14, wherein the antibody is an IgG antibody.

Embodiment P2 16

The cell penetrating conjugate of embodiment 14, wherein the antibody is an IgA, IgM, IgD or IgE antibody.

Embodiment P2 17

The cell penetrating conjugate of embodiment 14, wherein the antibody is an Fv fragment.

Embodiment P2 18

The cell penetrating conjugate of any one of embodiments 14 to 17, wherein the antibody is a humanized antibody.

Embodiment P2 19

The cell penetrating conjugate of any one of embodiments 1 to 18, wherein the non-cell penetrating protein binds an intracellular target.

Embodiment P2 20

The cell penetrating conjugate of embodiment 19, wherein the intracellular target is a target of a disease selected from the group consisting of autoimmune disease, inflammatory disease, metabolic disorder, developmental disorder, cardiovascular disease, liver disease, intestinal disease, infectious disease, endocrine disease, neurological disorder, and cancer.

Embodiment P2 21

The cell penetrating conjugate of embodiment 19 or 20, wherein the intracellular target is a signaling molecule or transcription factor.

Embodiment P2 22

The cell penetrating conjugate of embodiment 21, wherein the signaling molecule is a phosphatase or kinase.

Embodiment P2 23

The cell penetrating conjugate of embodiment 20, wherein the intracellular target is a cancer target.

Embodiment P2 24

The cell penetrating conjugate of embodiment 19, wherein the intracellular target is selected from the group consisting of STAT3, exportin 7, Her2, and Src.

Embodiment P2 25

The cell penetrating conjugate of embodiment 19, wherein the intracellular target is phosphorylated Src.

Embodiment P2 26

The cell penetrating conjugate of any one of embodiments 1 to 25, wherein the non-cell penetrating protein further comprises a label, a small molecule or a functional nucleic acid attached to the protein.

Embodiment P2 27

The cell penetrating conjugate of any one of embodiments 1 to 26 bound to an intracellular target.

Embodiment P2 28

A cell comprising the cell penetrating conjugate of any one of embodiments 1 to 26.

Embodiment P2 29

A pharmaceutical composition comprising the cell penetrating conjugate of any one of embodiments 1 to 26 and a pharmaceutically acceptable carrier.

Embodiment P2 30

The composition of embodiment 29, further comprising a second non-cell penetrating protein attached to one or more phosphorothioate nucleic acids.

Embodiment P2 31

The composition of embodiment 30, wherein the second non-cell penetrating protein binds an intracellular target.

Embodiment P2 32

The composition of embodiment 31, wherein the second non-cell penetrating protein binds a different epitope on the intracellular target relative to the non-cell penetrating protein of any one of embodiments 19 to 25.

Embodiment P2 33

The composition of embodiment 31, wherein the second non-cell penetrating protein binds a second intracellular target.

Embodiment P2 34

The composition of any one of embodiments 30 to 33, wherein the second non-cell penetrating protein is an antibody.

Embodiment P2 35

A kit comprising the cell penetrating conjugate of any one of embodiments 1 to 26 or the pharmaceutical composition of embodiment 29 and instructions for use.

Embodiment P2 36

The kit of embodiment 35, further comprising a second non-cell penetrating protein attached to one or more phosphorothioate nucleic acids.

Embodiment P2 37

The kit of embodiment 36, wherein the conjugate of any one of embodiments 1 to 26 and the second non-cell penetrating protein are in separate containers.

Embodiment P2 38

The kit of embodiment 36, wherein the pharmaceutical composition of embodiment 29 and the second non-cell penetrating protein are in separate containers.

Embodiment P2 39

The kit of any one of embodiments 36 to 38, wherein the second non-cell penetrating protein binds a different epitope on the intracellular target relative to the non-cell penetrating protein of any one of embodiments 19 to 25.

Embodiment P2 40

The kit of any one of embodiments 36 to 38, wherein the second non-cell penetrating protein binds a second intracellular target.

Embodiment P2 41

The kit of any one of embodiments 36 to 40, wherein the second non-cell penetrating protein is formulated as a pharmaceutical composition comprising the second non-cell penetrating protein and a pharmaceutically acceptable carrier.

Embodiment P2 42

The kit of any one of embodiments 35 to 41, wherein the second non-cell penetrating protein is an antibody.

Embodiment P2 43

A method of delivering a non-cell penetrating protein into a cell comprising contacting the cell with the cell penetrating conjugate of any one of embodiments 1 to 26.

Embodiment P2 44

The method of embodiment 43, wherein the non-cell penetrating protein binds the nuclear protein in the cytoplasm thereby forming a non-cell penetrating protein-nuclear protein complex.

Embodiment P2 45

The method of embodiment 44, wherein the non-cell penetrating protein-nuclear protein complex in not capable of entering the nucleus of the cell.

Embodiment P2 46

A method of treating a disease in a subject comprising administering to the subject an effective amount of the cell penetrating conjugate of any one of embodiments 1 to 26 wherein administration of the conjugate treats the disease in the subject.

Embodiment P2 47

The method of embodiment 46, further comprising administering to the subject a second non-cell penetrating protein attached to one or more phosphorothioate nucleic acids.

Embodiment P2 48

The method of embodiment 47, wherein the second non-cell penetrating protein binds a different epitope on the intracellular target relative to the conjugate of any one of embodiments 19 to 26.

Embodiment P2 49

The method of embodiment 47, wherein the second non-cell penetrating protein binds a second intracellular target.

Embodiment P2 50

The method of any one of embodiments 47 to 49, wherein the conjugate of any one of embodiments 1 to 26 and the second non-cell penetrating protein are administered simultaneously.

Embodiment P2 51

The method of any one of embodiments 47 to 49, wherein the conjugate of any one of embodiments 1 to 26 and the second non-cell penetrating protein are administered sequentially.

Embodiment P2 52

The method of any one of embodiments 47 to 51, wherein the second non-cell penetrating protein is an antibody.

Embodiment P2 53

The method of any one of embodiments 46 to 52, further comprising administering a second therapeutic agent to the subject.

Embodiment P2 54

The method of any one of embodiments 46 to 53, wherein the disease is selected from the group consisting of autoimmune disease, developmental disorder, inflammatory disease, metabolic disorder, cardiovascular disease, liver disease, intestinal disease, infectious disease, endocrine disease, neurological disorder, and cancer.

Embodiment P2 55

The method of embodiment 54, wherein the disease is cancer.

Embodiment P2 56

The method of embodiment 55, wherein the non-cell penetrating protein of the conjugate binds an intracellular target and the intracellular target is STAT3, exportin 7, Her2 or Src.

Embodiment P2 57

The method of embodiment 55, wherein the non-cell penetrating protein of the conjugate binds an intracellular target and the intracellular target is phosphorylated Src.

Embodiment P2 58

The method of embodiment 52, wherein the non-cell penetrating protein of the conjugate is an antibody that specifically binds STAT3 and the second non-cell penetrating protein is an antibody that specifically binds exportin 7.

Embodiment P2 59

The method of embodiment 52, wherein the non-cell penetrating protein of the conjugate is an antibody that specifically binds STAT3 and the second non-cell penetrating protein is an antibody that specifically binds another epitope of STAT3.

Embodiment 1

A cell penetrating conjugate comprising a non-cell penetrating protein attached to a phosphorothioate nucleic acid, wherein the phosphorothioate nucleic acid enhances intracellular delivery of the non-cell penetrating protein.

Embodiment 2

The cell penetrating conjugate of embodiment 1, wherein the phosphorothioate nucleic acid is covalently attached to the non-cell penetrating protein.

Embodiment 3

The cell penetrating conjugate of embodiment 1, wherein the phosphorothioate nucleic acid is non-covalently attached to the non-cell penetrating protein.

Embodiment 4

The cell penetrating conjugate of embodiment 1, wherein a plurality of phosphorothioate nucleic acids are attached to the non-cell penetrating protein.

Embodiment 5

The cell penetrating conjugate of embodiment 4, wherein each of the plurality of phosphorothioate nucleic acids are covalently attached to the protein.

Embodiment 6

The cell penetrating conjugate of embodiment 4, wherein each of the plurality of phosphorothioate nucleic acids are non-covalently attached to the protein.

Embodiment 7

The cell penetrating conjugate of embodiment 4, wherein the protein comprises covalently and non-covalently attached phosphorothioate nucleic acids.

Embodiment 8

The cell penetrating conjugate of any one of embodiments 1 to 7, wherein each phosphorothioate nucleic acid is independently attached to a lysine, arginine, cysteine, or histidine of the non-cell penetrating protein.

Embodiment 9

The cell penetrating conjugate of embodiment 8, wherein each phosphorothioate nucleic acid is attached to a cysteine of the protein.

Embodiment 10

The cell penetrating conjugate of any one of embodiments 1 to 9, wherein each phosphorothioate nucleic acid is independently 10, 20, 30, 40, 50, 60, 70, 80, 90, 100 or more nucleic acid residues in length.

Embodiment 11

The cell penetrating conjugate of embodiment 10, wherein each phosphorothioate nucleic acid is independently from 10 to 30 residues in length.

Embodiment 12

The cell penetrating conjugate of any one of embodiments 1 to 11, wherein the non-cell penetrating protein has a molecular weight of greater than 25 kD.

Embodiment 13

The cell penetrating conjugate of any one of embodiments 1 to 12, wherein the non-cell penetrating protein has a molecular weight of 25 to 750 kD.

Embodiment 14

The cell penetrating conjugate of any one of embodiments 1 to 13, wherein the non-cell penetrating protein is an antibody.

Embodiment 15

The cell penetrating conjugate of embodiment 14, wherein the antibody is an IgG antibody.

Embodiment 16

The cell penetrating conjugate of embodiment 14, wherein the antibody is an IgA, IgM, IgD or IgE antibody.

Embodiment 17

The cell penetrating conjugate of embodiment 14, wherein the antibody is an Fv fragment.

Embodiment 18

The cell penetrating conjugate of any one of embodiments 14 to 17, wherein the antibody is a humanized antibody.

Embodiment 19

The cell penetrating conjugate of any one of embodiments 1 to 18, wherein the non-cell penetrating protein binds an intracellular target.

Embodiment 20

The cell penetrating conjugate of embodiment 19, wherein the intracellular target is a target of a disease selected from the group consisting of autoimmune disease, inflammatory disease, metabolic disorder, developmental disorder, cardiovascular disease, liver disease, intestinal disease, infectious disease, endocrine disease, neurological disorder, and cancer.

Embodiment 21

The cell penetrating conjugate of embodiment 19 or 20, wherein the intracellular target is a signaling molecule or transcription factor.

Embodiment 22

The cell penetrating conjugate of embodiment 21, wherein the signaling molecule is a phosphatase or kinase.

Embodiment 23

The cell penetrating conjugate of embodiment 20, wherein the intracellular target is a cancer target.

Embodiment 24

The cell penetrating conjugate of embodiment 19, wherein the intracellular target is selected from the group consisting of STAT3, exportin 7, Her2, and Src.

Embodiment 25

The cell penetrating conjugate of embodiment 19, wherein the intracellular target is phosphorylated Src.

Embodiment 26

The cell penetrating conjugate of any one of embodiments 1 to 25, wherein the non-cell penetrating protein further comprises a label, a small molecule or a functional nucleic acid attached to the protein.

Embodiment 27

The cell penetrating conjugate of any one of embodiments 1 to 26 bound to an intracellular target.

Embodiment 28

The cell penetrating conjugate of embodiment 1, made by contacting an unattached non-cell penetrating protein with an unattached phosphorothioate nucleic acid and allowing the unattached phosphorothioate nucleic acid to covalently bind to an amino acid of the unattached non-cell penetrating protein thereby attaching and forming the cell penetrating conjugate.

Embodiment 29

The cell penetrating conjugated of embodiment 28, wherein the phosphorothioate nucleic acid comprises a covalent reactive moiety.

Embodiment 30

The cell penetrating conjugate of embodiment 29, wherein the covalent reactive moiety is reactive with a lysine, arginine, cysteine or histidine of the protein.

Embodiment 31

The cell penetrating conjugate of embodiment 29, wherein the covalent reactive moiety is reactive with a cysteine.

Embodiment 32

The cell penetrating conjugate of any one of embodiments 28 to 31, wherein the covalent reactive moiety is a vinyl sulfone.

Embodiment 33

The cell penetrating conjugate of embodiment 1, made by contacting an unattached non-cell penetrating protein with an unattached phosphorothioate nucleic acid and allowing the unattached phosphorothioate nucleic acid to bind to the unattached non-cell penetrating protein thereby attaching and forming the cell penetrating conjugate, wherein the unattached phosphorothioate nucleic acid comprises a substituent having the formula —S—S—(CH2)z-OH, wherein z is an integer from 1 to 10.

Embodiment 34

The cell penetrating conjugated of any one of embodiments 28 to 33, wherein the contacting is performed under reducing conditions.

Embodiment 35

The cell penetrating conjugate of any one of embodiments 28 to 33, wherein the unattached phosphorothioate nucleic acid is present in molar excess of the unattached non-cell penetrating protein.

Embodiment 36

A cell comprising the cell penetrating conjugate of any one of embodiments 1 to 35.

Embodiment 37

A pharmaceutical composition comprising the cell penetrating conjugate of any one of embodiments 1 to 35 and a pharmaceutically acceptable carrier.

Embodiment 38

The pharmaceutical composition of embodiment 37, further comprising a second non-cell penetrating protein attached to one or more phosphorothioate nucleic acids.

Embodiment 39

The pharmaceutical composition of embodiment 38, wherein the second non-cell penetrating protein binds an intracellular target.

Embodiment 40

The pharmaceutical composition of embodiment 39, wherein the second non-cell penetrating protein binds a different epitope on the intracellular target relative to the non-cell penetrating protein of any one of embodiments 19 to 25.

Embodiment 41

The pharmaceutical composition of embodiment 39, wherein the second non-cell penetrating protein binds a second intracellular target.

Embodiment 42

The pharmaceutical composition of any one of embodiments 38 to 41, wherein the second non-cell penetrating protein is an antibody.

Embodiment 43

A kit comprising the cell penetrating conjugate of any one of embodiments 1 to 35 or the pharmaceutical composition of embodiment 37 and instructions for use.

Embodiment 44

The kit of embodiment 43, further comprising a second non-cell penetrating protein attached to one or more phosphorothioate nucleic acids.

Embodiment 45

The kit of embodiment 44, wherein the conjugate of any one of embodiments 1 to 27 and the second non-cell penetrating protein are in separate containers.

Embodiment 46

The kit of embodiment 44, wherein the pharmaceutical composition of embodiment 37 and the second non-cell penetrating protein are in separate containers.

Embodiment 47

The kit of any one of embodiments 44 to 46, wherein the second non-cell penetrating protein binds a different epitope on the intracellular target relative to the non-cell penetrating protein of any one of embodiments 19 to 25.

Embodiment 48

The kit of any one of embodiments 44 to 46, wherein the second non-cell penetrating protein binds a second intracellular target.

Embodiment 49

The kit of any one of embodiments 44 to 48, wherein the second non-cell penetrating protein is formulated as a pharmaceutical composition comprising the second non-cell penetrating protein and a pharmaceutically acceptable carrier.

Embodiment 50

The kit of any one of embodiments 43 to 49, wherein the second non-cell penetrating protein is an antibody.

Embodiment 51

A method of delivering a non-cell penetrating protein into a cell comprising contacting the cell with the cell penetrating conjugate of any one of embodiments 1 to 35.

Embodiment 52

The method of embodiment 51, wherein the non-cell penetrating protein binds the nuclear protein in the cytoplasm thereby forming a non-cell penetrating protein-nuclear protein complex.

Embodiment 53

The method of embodiment 52, wherein the non-cell penetrating protein-nuclear protein complex in not capable of entering the nucleus of the cell.

Embodiment 54

A method of treating a disease in a subject comprising administering to the subject an effective amount of the cell penetrating conjugate of any one of embodiments 1 to 35 wherein administration of the conjugate treats the disease in the subject.

Embodiment 55

The method of embodiment 54, further comprising administering to the subject a second non-cell penetrating protein attached to one or more phosphorothioate nucleic acids.

Embodiment 56

The method of embodiment 55, wherein the second non-cell penetrating protein binds a different epitope on the intracellular target relative to the conjugate of any one of embodiments 19 to 26.

Embodiment 57

The method of embodiment 55, wherein the second non-cell penetrating protein binds a second intracellular target.

Embodiment 58

The method of any one of embodiments 55 to 57, wherein the conjugate of any one of embodiments 1 to 26 and the second non-cell penetrating protein are administered simultaneously.

Embodiment 59

The method of any one of embodiments 55 to 57, wherein the conjugate of any one of embodiments 1 to 26 and the second non-cell penetrating protein are administered sequentially.

Embodiment 60

The method of any one of embodiments 55 to 59, wherein the second non-cell penetrating protein is an antibody.

Embodiment 61

The method of any one of embodiments 54 to 60, further comprising administering a second therapeutic agent to the subject.

Embodiment 62

The method of any one of embodiments 54 to 61, wherein the disease is selected from the group consisting of autoimmune disease, developmental disorder, inflammatory disease, metabolic disorder, cardiovascular disease, liver disease, intestinal disease, infectious disease, endocrine disease, neurological disorder, and cancer.

Embodiment 63

The method of embodiment 62, wherein the disease is cancer.

Embodiment 64

The method of embodiment 63, wherein the non-cell penetrating protein of the conjugate binds an intracellular target and the intracellular target is STAT3, exportin 7, Her2 or Src.

Embodiment 65

The method of embodiment 63, wherein the non-cell penetrating protein of the conjugate binds an intracellular target and the intracellular target is phosphorylated Src.

Embodiment 66

The method of embodiment 60, wherein the non-cell penetrating protein of the conjugate is an antibody that specifically binds STAT3 and the second non-cell penetrating protein is an antibody that specifically binds exportin 7.

Embodiment 67

The method of embodiment 60, wherein the non-cell penetrating protein of the conjugate is an antibody that specifically binds STAT3 and the second non-cell penetrating protein is an antibody that specifically binds another epitope of STAT3.

---

What is claimed is:

1. An antibody covalently attached to one or more phosphorothioate nucleic acids, wherein the one or more phosphorothioate nucleic acids are independently from 10 to 30 residues in length, wherein the antibody binds an intracellular target and wherein the antibody is non-cell penetrating in the absence of said one or more phosphorothioate nucleic acids.

2. The antibody of claim 1, wherein each phosphorothioate nucleic acid is independently attached to a lysine, arginine, cysteine, or histidine of the antibody.

3. The antibody of claim 1, wherein the intracellular target is a target of a disease selected from the group consisting of autoimmune disease, inflammatory disease, metabolic disorder, developmental disorder, cardiovascular disease, liver disease, intestinal disease, infectious disease, endocrine disease, neurological disorder, and cancer.

4. The antibody of claim 1, wherein the intracellular target is a cancer target.

5. The antibody of claim 1, wherein the intracellular target is selected from the group consisting of STAT3, exportin 7, and Src.

6. A cell comprising the antibody of claim 1.

7. A pharmaceutical composition comprising the antibody of claim 1 and a pharmaceutically acceptable carrier.

8. A kit comprising the antibody of claim 1 or the pharmaceutical composition of claim 7 and instructions for use.

* * * * *